United States Patent
Shafi et al.

(10) Patent No.: US 11,923,880 B2
(45) Date of Patent: Mar. 5, 2024

(54) NON-INVASIVE ELECTROMAGNETIC SYSTEM FOR THE DIAGNOSIS AND MONITORING OF IN-VIVO AND EX-VIVO SKIN ANOMALIES USING LESION-OPTIMIZED SENSOR SYSTEM DESIGN AND TOPOLOGY

(71) Applicant: American University of Beirut, Beirut (LB)

(72) Inventors: Nader Shafi, Beirut (LB); Joseph Costantine, Albuquerque, NM (US); Rouwaida Kanj, Portland, OR (US); Youssef Tawk, Albuquerque, NM (US); Assaad Eid, Paris (FR); Mazen Kurban, Beirut (LB); Jihane Abou Rahal, Beirut (LB); Ali H. Ramadan, Beirut (LB)

(73) Assignee: American University of Beirut, Beirut (LB)

( * ) Notice: Subject to any disclaimer, the term of this patent is extended or adjusted under 35 U.S.C. 154(b) by 143 days.

(21) Appl. No.: 17/824,395

(22) Filed: May 25, 2022

(65) Prior Publication Data
US 2022/0385315 A1    Dec. 1, 2022

Related U.S. Application Data

(60) Provisional application No. 63/192,612, filed on May 25, 2021.

(51) Int. Cl.
*H04B 1/04* (2006.01)
*H03H 7/38* (2006.01)
*H01P 5/18* (2006.01)

(52) U.S. Cl.
CPC ............. *H04B 1/0458* (2013.01); *H03H 7/38* (2013.01); *H01P 5/18* (2013.01)

(58) Field of Classification Search
CPC ........... H04B 1/0458; H03H 7/38; H01P 5/18; A61B 2560/0238; A61B 2560/0431; A61B 5/0507; A61B 5/0531; A61B 5/444; A61B 5/7225; A61B 5/7267
See application file for complete search history.

(56) References Cited

U.S. PATENT DOCUMENTS

| | | | |
|---|---|---|---|
| 6,061,589 | A | 5/2000 | Bridges et al. |
| 8,089,417 | B2 | 1/2012 | Popovic et al. |
| 10,213,128 | B2 | 2/2019 | Mahfouz |

(Continued)

FOREIGN PATENT DOCUMENTS

WO    2020/176857 A1    9/2020

OTHER PUBLICATIONS

Abdoh, S.F. et al. "Cervical Cancer Diagnosis Using Random Forest Classifier With SMOTE and Feature Reduction Techniques," IEEE Access, 2018, 6: 59475-59485.

(Continued)

*Primary Examiner* — David E Lotter
(74) *Attorney, Agent, or Firm* — J. Peter Paredes; Amin Talati Wasserman LLP

(57) ABSTRACT

An electromagnetic (EM)-based diagnostics and monitoring system and method for the non-Invasive diagnosis and monitoring of in-vivo and ex-vivo Skin Anomalies Using Lesion-Optimized Sensor System Design and Topology is disclosed herein.

20 Claims, 27 Drawing Sheets

(56) References Cited

U.S. PATENT DOCUMENTS

| | | | |
|---|---|---|---|
| 10,493,296 B2 | 12/2019 | Vo-Dinh et al. | |
| 2004/0127780 A1* | 7/2004 | Ollmar | A61B 5/444 600/365 |
| 2004/0152997 A1* | 8/2004 | Davies | A61B 5/4381 600/547 |
| 2005/0107718 A1 | 5/2005 | Hashimshony | |
| 2005/0203436 A1 | 9/2005 | Davies | |
| 2008/0009764 A1* | 1/2008 | Davies | A61B 5/6834 600/547 |
| 2008/0226151 A1 | 9/2008 | Zouridakis et al. | |
| 2008/0262376 A1 | 10/2008 | Price | |
| 2009/0326384 A1 | 12/2009 | Bigio et al. | |
| 2012/0323135 A1* | 12/2012 | Davies | G16H 50/20 600/547 |
| 2016/0058364 A1 | 3/2016 | Ionescu et al. | |
| 2019/0179008 A1 | 6/2019 | Tavassolian et al. | |
| 2022/0369965 A1* | 11/2022 | Liu | A61B 5/14507 |
| 2023/0200725 A1* | 6/2023 | Liu | A61B 5/7267 600/306 |

OTHER PUBLICATIONS

Aberg, P. et al. "Skin cancer identification using multifrequency electrical impedance—a potential screening tool," IEEE Trans. Biomed. Eng., 2004, 51(12): 2097-2102.

Abhishek, K. and Khunger, N. "Complications of skin biopsy," J. Cutan. Aesthetic Surg., 2015, 8(4): 239-241.

Alekseev, S. I. et al. "Millimeter wave reflectivity used for measurement of skin hydration with different moisturizers," Skin Res. Technol., 2008, 14(4): 390-396.

Alghamdi, M. et al. "Predicting diabetes mellitus using SMOTE and ensemble machine learning approach: The Henry Ford Exercise Testing (FIT) project," PLoS One, 2017, 12(7) 1-15.

Andrew, T.W. et al. "Reduction in skin cancer diagnoses in the UK during the COVID-19 pandemic," Clin. Exp. Dermatol., 2021, 46(1): 145-146, 2021.

Brind'Amour, K. "All About Common Skin Disorders," Healthline. https://www.healthline.com/health/skin-disorders (accessed Jan. 3, 2021) (30 pages).

Brinker, T.J. et al. "Skin Cancer Classification Using Convolutional Neural Networks: Systematic Review," J. Med. Internet Res., 2018, 20(10): e11936 (14 pages).

Cervantes, J. et al. "A comprehensive survey on support vector machine classification: Applications, challenges and trends," Neurocomputing, 2020, 408: 189-215.

Changpuak A. C. F. "Arduino Shield SUPERMOD," Arduino, 2021. https://www.changpuak.ch/electronics/Arduino-Shield-SUPERMOD.php (accessed Jan. 8, 2021) (16 pages).

Chiu, H. et al. "Breast Cancer-Detection System Using PCA, Multilayer Perceptron, Transfer Learning, and Support Vector Machine," IEEE Access, 2020, 8: 204309-204324.

Corbo, M.D. and Wismer, J. "Agreement between dermatologists and primary care practitioners in the diagnosis of malignant melanoma: review of the literature," J. Cutan. Med. Surg., 2012, 16(5): 306-310.

Demartino, C. "Brushing Up on Network Analyzer Fundamentals," Microwaves & RF, Jun. 27, 2018. https://www.mwrf.com/technologies/test-measurement/article/21849241/brushing-up-on-network-analyzer-fundamentals (accessed Feb. 17, 2021) (13 pages).

Earnshaw, C.H. et al. "Reduction in skin cancer diagnosis, and overall cancer referrals, during the COVID-19 pandemic," Br. J. Dermatol., 2020, 183(4): 792-794.

Töpfer, F. et al. "Millimeter-Wave Near-Field Probe Designed for High-Resolution Skin Cancer Diagnosis," IEEE Trans. Microw. Theory Tech., 2015, 63(6) 2050-2059.

Farrugia, L. et al. "Accurate in vivo dielectric properties of liver from 500 MHz to 40 GHz and their correlation to ex vivo measurements," Electromagn. Biol. Med., 2016, 35(4): 365-373.

Fernandez, A. et al. "SMOTE for Learning from Imbalanced Data: Progress and Challenges, Marking the 15-year Anniversary," J. Artif. Intell. Res., 2018, 61: 863-905.

Fotouhi, S. et al. "A comprehensive data level analysis for cancer diagnosis on imbalanced data," J. Biomed. Inform., 2019, 90: 103089 (30 pages).

Gabriel, C. et al. "The dielectric properties of biological tissues: I. Literature survey," Phys. Med. Biol., 1996, 41(11): 2231-2249.

Gabriel, S. et al. "The dielectric properties of biological tissues: II. Measurements in the frequency range 10 Hz to 20 GHz," Phys. Med. Biol., 1996, 41(11): 2251-2269.

Gabriel, S. et al. "The dielectric properties of biological tissues: III. Parametric models for the dielectric spectrum of tissues," Phys. Med. Biol., 1996, 41(11): 2271-2293.

Gorin, S. N. S. et al. "The future of cancer screening after COVID-19 may be at home," Cancer, 2021, 127(4): 498-503.

Halter, R.J. et al. "The correlation of in vivo and ex vivo tissue dielectric properties to validate electromagnetic breast imaging: initial clinical experience," Physiol. Meas., 2009, 30(6): S121-S136.

Hanna, J. et al. "Noninvasive, wearable, and tunable electromagnetic multisensing system for continuous glucose monitoring, mimicking vasculature anatomy" Sci Adv., 2020, 6(24): 1-11.

Huang, S. et al. "Applications of Support Vector Machine (SVM) Learning in Cancer Genomics," Cancer Genomics Proteomics, 2017, 15(1): 41-51.

Huang, Z. et al. "Adaptive over-sampling method for classification with application to imbalanced datasets in aluminum electrolysis," Neural Comput. Appl., 2020, 32(11): 7183-7199.

Huber, D et al. "The compensation of perturbing temperature fluctuation in glucose monitoring technologies based on impedance spectroscopy," Med. Biol. Eng. Comput., 2007, 45(9): 863-876.

Kalter, L. "Doctors Warn of Skin Cancer Screening Crisis," Medscape. 2021. http://www.medscape.com/viewarticle/944885 (accessed Feb. 4, 2021) (3 pages).

Kazemi, F. et al. "Detection of biological abnormalities using a near-field microwave microscope," Int. J. Microw. Wirel. Technol., 2018, 10(8): 933-941.

Kazemi, F. et al. "Nondestructive high-resolution microwave imaging of biomaterials and biological tissues," AEU—Int. J. Electron. Commun., 2018, 84: 177-185.

Kittler, H. et al. "Diagnostic accuracy of dermoscopy," Lancet Oncology, 2002, 3(3): 159-65.

"ZHDC-10-63+ Mini Circuits | Directional Coupler," Everything RF, 2021. https://www.everythingrf.com/products/directional-couplers/mini-circuits/45-12-zhdc-10-63 (accessed Jan. 3, 2021) (3 pages).

Lazebnik, M. et al. "A large-scale study of the ultrawideband microwave dielectric properties of normal, benign and malignant breast tissues obtained from cancer surgeries," Phys. Med. Biol., 2007, 57(20): 6093-6115.

Lindelöf, B. and Hedblad, M.A. "Accuracy in the clinical diagnosis and pattern of malignant melanoma at a dermatological clinic," J. Dermatol., 1994, 21(7): 461-464.

Liu, Y. et al. "Using Deep Learning to Inform Differential Diagnoses of Skin Diseases," Google AI Blog, 2019. http://ai.googleblog.com/2019/09/using-deep-learning-to-inform.html (accessed Feb. 4, 2021) (6 pages).

Martinsen, G. et al. "Interface Phenomena and Dielectric Properties of Biological Tissue.," Encyclopedia of Surface and Colloid Sci., 2002: 2643-2652.

Mirbeik-Sabzevari, A. et al. "High-Contrast, Low-Cost, 3-D Visualization of Skin Cancer Using Ultra-High- Resolution Millimeter-Wave Imaging," IEEE Trans. Med. Imaging, 2019, 38(9): 2188-2197.

Mirbeik-Sabzevari, A. et al. "Ultra-wideband millimeter-wave dielectric characteristics of freshly excised normal and malignant human skin tissues," IEEE Trans. Biomed. Eng., 2018, 65(6): 1320-1329.

Morton, C. A. and Mackie, R. M. "Clinical accuracy of the diagnosis of cutaneous malignant melanoma," Br. J. Dermatol., 1998, 138(2): 283-287.

Patt, D. et al. "Impact of COVID-19 on Cancer Care: How the Pandemic Is Delaying Cancer Diagnosis and Treatment for American Seniors," JCO Clin. Cancer Inform., 2020, 4: 1059-1071.

(56) References Cited

OTHER PUBLICATIONS

Pollacco, D.A. et al. "Characterization of the dielectric properties of biological tissues and their correlation to tissue hydration," IEEE Trans. Dielectr. Electr. Insul., 2018, 25(6): 2191-2197.
Rahman, A. et al. "Early detection of skin cancer via terahertz spectral profiling and 3D imaging," Biosens. Bioelectron., 2016, 82: 64-70.
Salahuddin, S. "Comparison of in-vivo and ex-vivo dielectric properties of biological tissues," in 2017 International Conference on Electromagnetics in Advanced Applications (ICEAA), Sep. 2017, 582-585.
Schepps, J.L. and Foster, K.R. "The UHF and microwave dielectric properties of normal and tumour tissues: variation in dielectric properties with tissue water content," Phys. Med. Biol., 1980, 25(6): 1149-1159.
Schwan, H.P. "Electrical Properties of Tissue and Cell Suspensions" Advances in Biological and Medical Physics, 1957, 5: 147-209.
Shen, Y. et al. "Oriented Feature Selection SVM Applied to Cancer Prediction in Precision Medicine," IEEE Access, 2018, 6: 48510-48521.
Tabib-Azar, M. et al. "Evanescent microwaves: a novel super-resolution noncontact nondestructive imaging technique for biological applications," IEEE Trans. Instrum. Meas., 1999, 48(6): 1111-1116.
Taeb, A. et al. "Millimetre-wave waveguide reflectometers for early detection of skin cancer," IET Microw. Antennas Propag., 2013, 7(14): 1182-1186.
"Early Detection," The Skin Cancer Foundation. https://www.skincancer.org/early-detection/ (accessed Jan. 3, 2021) (3 pages).
"What is a Vector Network Analyzer, VNA," Electronics Notes, https://www.electronics-notes.com/articles/test-methods.rf-vector-network-analyzer-vna/what-is-a-vna.php (accessed Feb. 17, 2021) (6 pages).
WIPO ISA/US, International Search Report and Written Opinion issued in corresponding application, PCT/US2022/030868, dated Aug. 30, 2022 (8 pages).
Wetterlin, S. "Use of Phase Shift to Resolve Sign Ambiguity and Improve Accuracy in the AD8302 Phase Detector," 2017: 9 (9 pages).
Wiharto, W. et al. "Intelligence System for Diagnosis Level of Coronary Heart Disease with K-Star Algorithm," Healthc. Inform. Res., 2016, 22(1): 30-38.
Zafiropoulos, E. et al. "A Support Vector Machine Approach to Breast Cancer Diagnosis and Prognosis," in Artificial Intelligence Applications and Innovations, Boston, MA, 2006: 500-507.
Zamani, A. et al. "Lung cancer detection using frequency-domain microwave imaging," Electron. Lett., 2015, 51(10): 740-741.
Analog Devices, "AD8302 Datasheet and Product Info | Analog Devices." 2022. https://www.analog.com/en/products/ad8302.html#/product-overview (accessed Jan. 3, 2021) (8 pages).
Ansys, Inc. "Ansys HFSS: High Frequency Electromagnetic Field Simulation Software" 2022. https://www.ansys.com/products/electronics/ansys-hfss (accessed Jan. 3, 2021) (9 pages).
Arduino, "Arduino IDE 1.8.19", 2022. https://www.arduino.cc/en/software (accessed Jan. 8, 2021) (4 pages).
Arduino, "Arduino Nano 33 IoT", 2021. https://store-usa.arduino.cc/collections/most-popular/products/arduino-nano-33-iot (accessed Jan. 3, 2021) (7 pages).
American Cancer Society, "Basal and Squamous Cell Skin Cancer Tests | Skin Cancer Biopsy." https://www.cancer.org/cancer/basal-and-squamous-cell-skin-cancer/detection-diagnosis-staging/how-diagnosed.html (accessed Jan. 3, 2021) (3 pages).

Barris Laser & Skin Care, "Considering Laser Hair Removal? Get to Know Your Fitzpatrick Skin Type" Barris Laser & Skin Care. https://barrislaser.com/considering-laser-hair-removal-get-to-know-your-fitzpatrick-skin-type/ (accessed Jan. 10, 2021) (6 pages).
National Cancer Institute, "Definition of Mohs surgery—NCI Dictionary of Cancer Terms—National Cancer Institute," Feb. 2, 2011. https://www.cancer.gov/publications/dictionaries/cancer-terms/def/mohs-surgery (accessed Feb. 16, 2021) (1 page).
American University of Beirut, "Federalwide Assurance." 2021. https://www.aub.edu.lb/irb/Pages/federalwideassurance.aspx (accessed Feb. 5, 2021) (1 page).
Mathworks, "Matlab (R2018b)", 2021. https://www.mathworks.com/products/matlab.html. (accessed Jan. 3, 2021) (4 pages).
Maxim Integrated, "MAX2871 23.5MHz to 6000MHz Fractional/Integer-N Synthesizer/VCO" 2022. https://www.maximintegrated.com/en/products/comms/wireless-rf/MAX2871.html (accessed Jan. 3, 2021) (4 pages).
The Skin Cancer Foundation, "Melanoma Warning Signs and Images," https://www.skincancer.org/skin-cancer-information/melanoma/melanoma-warning-signs-and-images/ (accessed Feb. 3, 2021) (4 pages).
Mayo Clinic, "Mohs surgery—Mayo Clinic" 2020. https://www.mayoclinic.org/tests-procedures/mohs-surgery/about/pac-20385222 (accessed Feb. 16, 2021) (7 pages).
Keysight Technologies, "N9923A FieldFox Handheld RF Vector Network Analyzer, 4 GHZ and 6 GHz" Keysight, 2022. https://www.keysight.com/en/pdx-x201782-pn-N9923A/fieldfox-handheld-rf-vector-network-analyzer-4-ghz-and-6-ghz?cc=LB&lc=eng (accessed Jan. 3, 2021) (5 pages).
The Skin Cancer Foundation, "Not My Face!," Nov. 1, 2017. https://www.skincancer.org/blog/not-my-face/ (accessed Feb. 4, 2021) (7 pages).
Keysight Technologies, "PathWave Advanced Design System (ADS)," 2021. https://www.keysight.com/zz/en/products/software/pathwave-design-software/pathwave-advanced-design-system.html (accessed Jan. 3, 2021) (5 pages).
JLCPCB, "Pcb Prototype—JLCPCB" 2022. https://jlcpcb.com/quote/pcbOrderFaq/PCB%20Stackup (accessed Jan. 3, 2021) (1 page).
World Health Organization, "Radiation: Ultraviolet (UV) radiation and skin cancer.," Oct. 16, 2017. https://www.who.int/news-room/q-a-detail/radiation-ultraviolet-(uv)-radiation-and-skin-cancer (accessed Jan. 3, 2021) (4 pages).
Federal Communications Commission, "Radio Frequency Safety," Mar. 2, 2011. https://www.fcc.gov/general/radio-frequency-safety-0 (accessed Jan. 8, 2021) (5 pages).
American Cancer Society, "Radiofrequency (RF) Radiation." American Cancer Society, 2020. https://www.cancer.org/cancer/cancer-causes/radiation-exposure/radiofrequency-radiation.html (accessed Feb. 5, 2021) (6 pages).
Rogers Corporation, "RT/duroid@ 5880 Laminates" 2022. https://rogerscorp.com/advanced-electronics-solutions/rt-duroid-laminates/rt-duroid-5880-laminates (accessed Feb. 15, 2021) (3 pages).
Mini-Circuits, "SIM-762H+" 2021. https://www.minicircuits.com/WebStore/dashboard.html?model=SIM-762H%2B (accessed Jan. 3, 2021) (6 pages).
Mayo Clinic, "Skin cancer—Diagnosis and treatment," https://www.mayoclinic.org/diseases-conditions/skin-cancer/diagnosis-treatment/drc-20377608 (accessed Feb. 4, 2021) (7 pages).
Mayo Clinic, "Skin cancer—Symptoms and causes," https://www.mayoclinic.org/diseases-conditions/skin-cancer/symptoms-causes/syc-20377605 (accessed Jan. 3, 2021) (10 pages).
cancer.net, "Skin Cancer (Non-Melanoma)—Introduction," Jun. 25, 2012. https://www.cancer.net/cancer-types/skin-cancer-non-melanoma/introduction (accessed Feb. 4, 2021) (2 pages).

\* cited by examiner

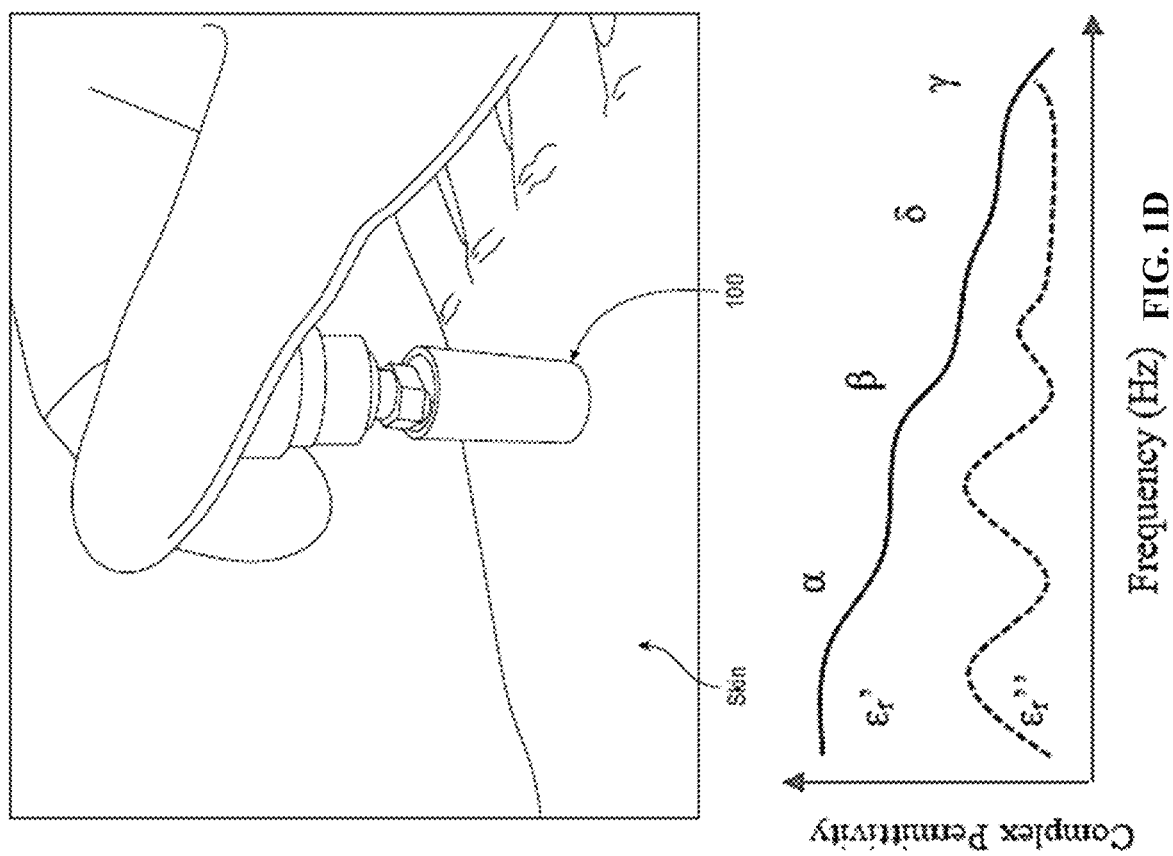
FIG. 1C
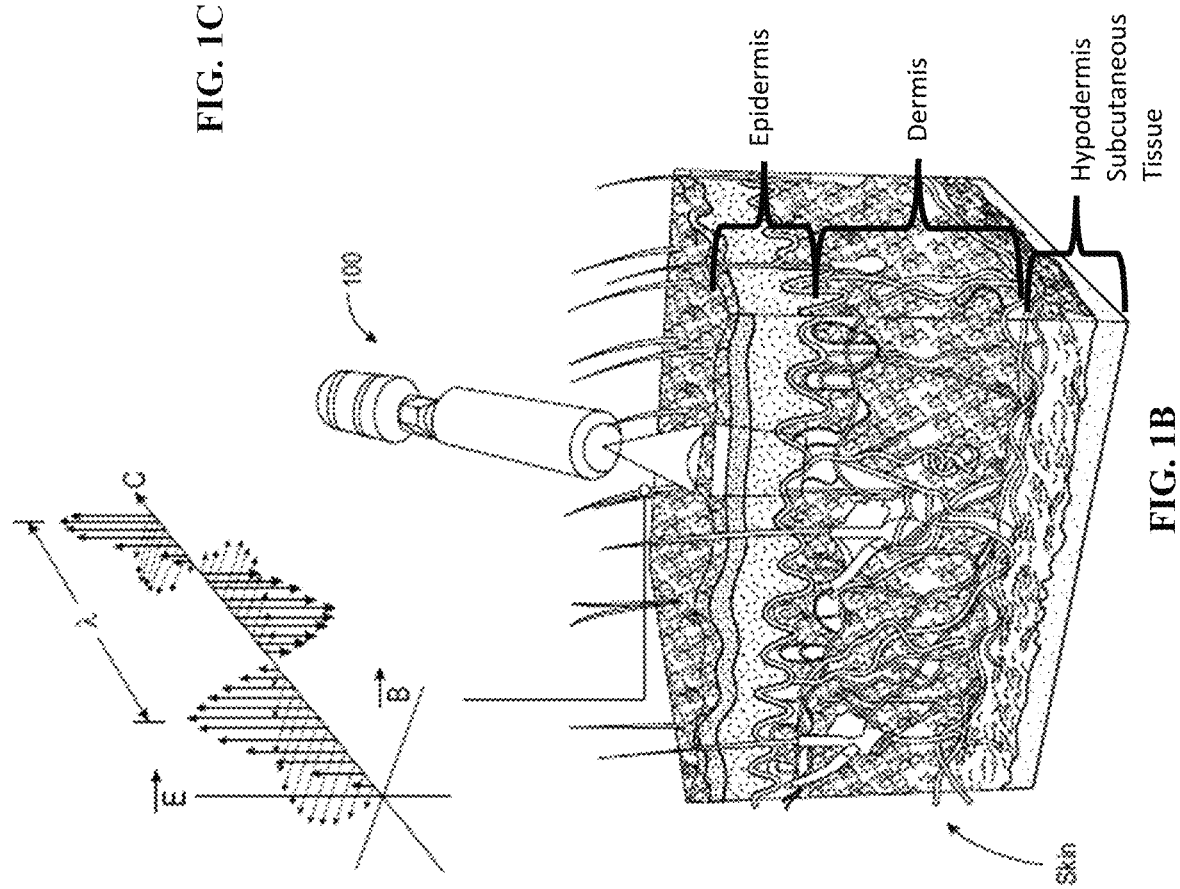
FIG. 1B
FIG. 1D

Focused EM Field.

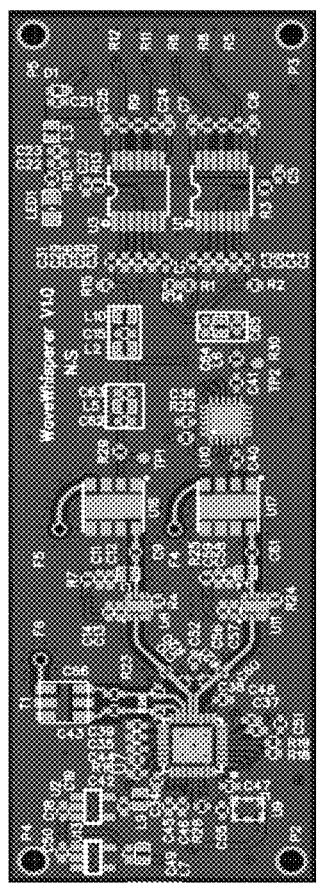
FIG. 16A
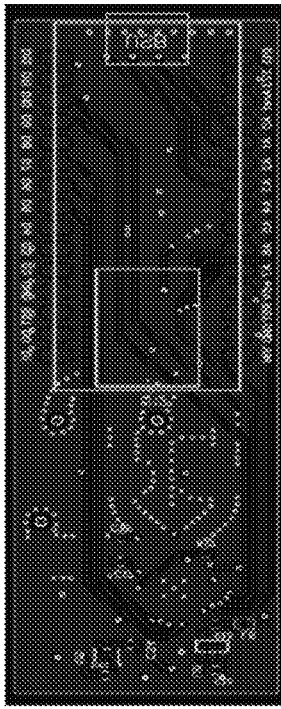
FIG. 16C
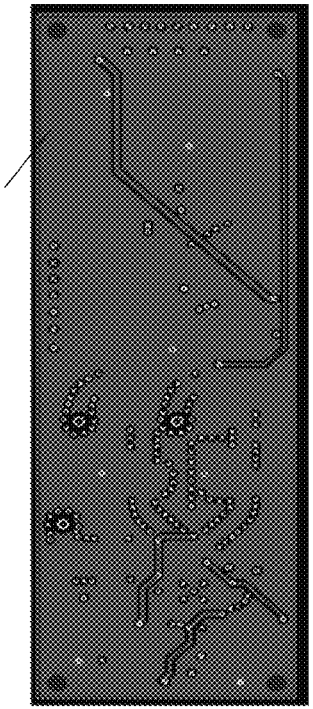
FIG. 16B
Layer 1: another view
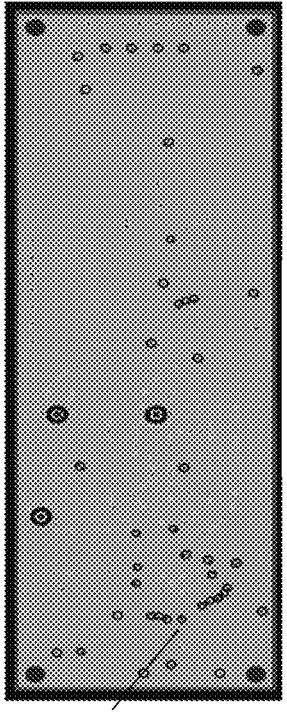
FIG. 16E
FIG. 16D

NON-INVASIVE ELECTROMAGNETIC SYSTEM FOR THE DIAGNOSIS AND MONITORING OF IN-VIVO AND EX-VIVO SKIN ANOMALIES USING LESION-OPTIMIZED SENSOR SYSTEM DESIGN AND TOPOLOGY

CROSS-REFERENCE TO RELATED APPLICATIONS

The present application claims priority to U.S. provisional application Ser. No. 63/192,612, filed May 25, 2021, herein incorporated by reference in its entirety.

BACKGROUND

The present application generally relates to sensors and more particularly to sensors to detect skin anomalies.

Skin cancers are amongst the most prevalent types of cancer, while also counting as some of the most dangerous forms of a skin anomaly [1]. Skin cancer can be divided into two categories, non-melanoma and melanoma. Non-melanoma skin cancers (NMSC) are mainly Basal Cell Carcinoma (BCC) and Squamous Cell Carcinoma (SCC) which are often non-lethal and comprise the largest portion of skin cancers [2]. Screening for skin cancer often includes surgical interventions to confirm the diagnosis, which can be uncomfortable and potentially disfiguring [3]. Non-melanoma skin cancer is often a byproduct of excessive exposure to UV radiation and is usually present in areas of the body that are regularly uncovered, such as the arms, legs, and neck, whereas melanoma can be a result of genetic predisposition as well as UV exposure [4]. Notably, the world health organization estimates that 2-3 million non-melanoma and more than 130,000 melanoma cancers occur globally each year [5]. It is needless to emphasize that early diagnosis of skin cancer and the timely intervention increase the chances of successful treatment and enhance the rate of survival [6].

Typically, medical professionals such as dermatologists, practitioners, and physicians follow systematic procedures in order to diagnose skin anomalies, including visual inspection (Dermoscopy) and skin biopsies [7]. Dermoscopy is the initial step in diagnosing a skin anomaly, and it makes use of a dermatoscope, essentially a tool composed of a magnifying lens and a powerful light source to enhance the medical professional's observation of the lesion's characteristics. In Dermoscopy, a medical professional evaluates the pigmentation and morphologic characteristics of the lesion and associates the observed characteristics with diseases of similar qualitative attributes. In the particular case of Melanoma, the investigated characteristics are the Asymmetry, Border, Color, Diameter of the lesion, and whether the suspected lesion is Evolving, which is also known as the ABCDE method [8]. If the lesion is deemed suspicious, a surgical procedure known as the biopsy is required. The biopsy is an invasive procedure in which the suspected lesion is removed for histopathological examination to determine if the lesion is cancerous or not. This procedure is invasive, discomforting, scarring, and may result in other complications to the patient [9], [10]. Furthermore, several studies have shown that the diagnostic accuracy of dermatologists and practitioners varied greatly depending on years of experience, highlighting the subjective nature of the screening procedures [11]-[14].

Due to the inconvenient, subjective, invasive, and time-consuming nature of skin cancer diagnosis, many researchers have explored the potential of relying on non-invasive means for the characterization of healthy and anomalous skin. As a result, several publications have verified the ability of technologies such as bio-electrical impedance [15], machine learning image classification [16], [17], and electromagnetic-based (EM-based) techniques to diagnose a variety of skin anomalies [18]-[20].

The work presented in [15] relies on a probe consisting of concentric ring electrodes to measure the bio-electric impedance of the lesion at low frequencies from 1 KHz to a few MHz. By measuring the variations in the magnitude and phase of the skin impedance, certain types of skin lesions can be identified. More recently, there has been significant interest in developing machine learning and artificial intelligence algorithms dedicated to classify and diagnose skin anomalies based on images of the suspected lesions [17]. Accuracies comparable to the visual inspection of dermatologists and general practitioners have been reported. On the other hand, EM-based techniques that employ waveguides, coaxial probes, radars, and multi-antenna systems operating within the microwave or millimeter wave (mm-wave) portion of the frequency spectrum have also been proposed for the detection of skin abnormalities. These techniques characterize human skin permittivity at different frequency spans and leverage EM principles to differentiate between healthy and anomalous skin lesions as detailed in [21]-[23]. Such detection is made possible due to the distinctive interaction between EM waves emanating from a sensor and the increased water content within skin anomalies the also bear different dielectric properties compared to their healthy counterparts [18], [23]. These studies, which concluded with statistically significant differences between the devices' physical responses to healthy and anomalous skin, highlight the ability of EM-based techniques to sense skin abnormalities safely and non-invasively. These techniques have also been demonstrated to have promising results when used for applications such lung cancer detection [24], skin hydration measurement [25], and blood glucose monitoring [26].

The present invention attempts to solve these problems as well as others.

SUMMARY OF THE INVENTION

Provided herein are systems, methods and apparatuses for a Non-Invasive Electromagnetic System for The Diagnosis and Monitoring of In-vivo and Ex-vivo Skin Anomalies Using Lesion-Optimized Sensor System Design and Topology.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

BRIEF DESCRIPTION OF THE DRAWINGS

In the accompanying figures, like elements are identified by like reference numerals among the several preferred embodiments of the present invention.

FIG. 1B is a schematic of a typical measurement scenario on top of anomalous skin; FIG. 1C is a perspective view of a photograph of the setup where the sensor is positioned on top of the skin; and FIG. 1D is a graph of the dispersion ranges of both the real and imaginary parts of the complex permittivity of tissues as a function of frequency.

FIGS. 16A-16E are schematics of the multiple layers of the printed circuit board of the wave analyzer, according to one embodiment.

DETAILED DESCRIPTION OF THE INVENTION

Figure 1A:
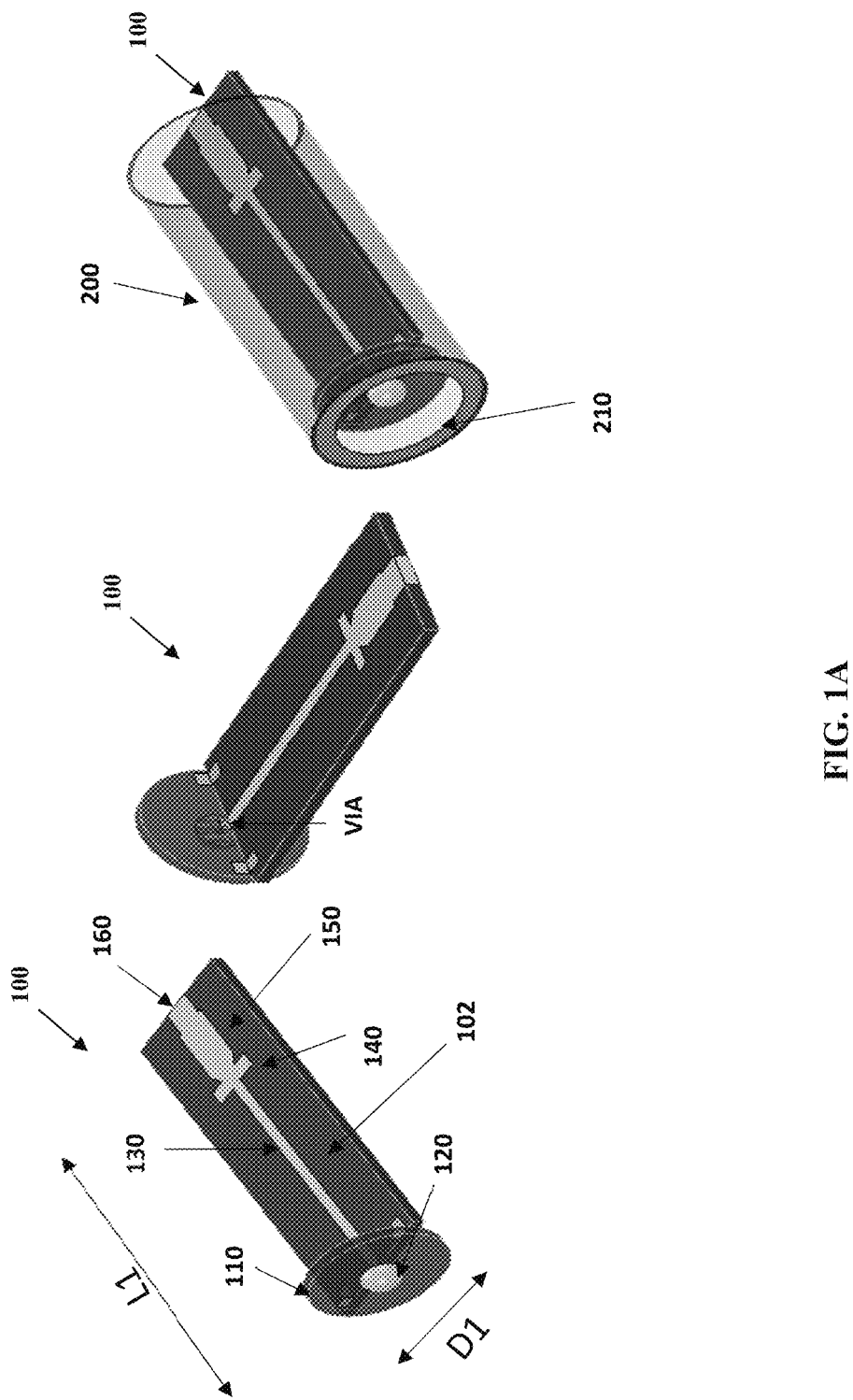
FIG. 1A is a schematic of an embodiment of the Lesion-Optimized EM Sensor.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Generally speaking, a novel, portable, real-time, and low-cost sensing system is disclosed and tailored for the accurate detection of skin cancer by relying on a highly sensitive electromagnetic sensor, a custom wave analyzer circuit, and machine learning algorithms that rely on the EM sensor's physical responses to assess the risk of the skin anomaly. In fact, the advent of the debilitating COVID-19 pandemic has resulted in a substantial decrease in cancer screenings, which is equivalent to delays in the timely identification of the disease [27]. This decrease is a result of multiple factors such as the quarantine orders, the disruption of medical care services, and the patients rescheduling their clinical visits during the critical months of the pandemic due to fear of COVID-19 exposure within medical facilities [27], [28]. Additionally, a recent anecdotal testimony has also demonstrated the reluctance and anxiety associated with attending to medical care for skin cancer screening over the fear of COVID-19 exposure, a case that proved to be indeed a skin cancer one [31]. More specifically, skin cancer has witnessed a significant reduction in diagnosis, screening, and referral procedures [29], [30]. These observations and the accompanied research studying the detrimental effects of the COVID-19 pandemic on skin cancer screening services profoundly highlight the need for a quick point-of-care device capable of diagnosing skin cancer both clinically and at households. This need is further amplified by the fact that delays in skin cancer screening cause the disease to evolve, potentially spreading into other tissues and resulting in dangerous health complications. Accordingly, the system described herein is characterized by several embodiments that underline its optimality for adoption in skin cancer diagnosis within clinical settings and regular households, while offering several advantages when compared to other traditional techniques and approaches.

The first embodiment of the system and method comprises the electromagnetic sensor's compact topology, which is distinguished by a sensing tip that is specifically optimized to adapt to the dimensions of skin lesions, as shown in FIG. 1A. The designed miniature sensing tip guarantees an accurate measurement of the suspected region without being influenced by the adjacent healthy skin. The latter can happen as a consequence to using relatively large sensing apertures in other electromagnetic structures, such as coaxial probes or waveguides. Additionally, the proposed sensor's topology ensures the high concentration of the EM fields around the optimized sensing tip, enabling elevated accuracy, sensitivity, and controllable penetration depth of the EM fields to reach tumors that have grown deeply beneath the surface of the skin, as illustrated in FIG. 1B.

The sensor (FIG. 1C) is shielded from electromagnetic interference in order to prevent measurement errors, as shown in FIG. 1C. In addition, FIG. 1C demonstrates the placement of the sensor on top of the skin in a real measurement scenario. Aside from enabling the detection of miniature skin cancers, the miniature sensing tip is particularly useful for surgeons removing skin cancers. In the traditional wide-margin excision method, "normal skin" surgical margins need to be drawn around the skin cancer and removed. They vary in size from about 3 mm to about 20 mm beyond the visible tumor size. This is done to make sure all the cancer is removed as cancer cells often extend beyond what the physician clinically sees. Due to its fine sensing tip, the proposed sensor can accurately determine the boundaries of the cancer both qualitatively and quantitatively.

This embodiment applies to patients undergoing Moh's Micrographic Surgery, where successive excisions from the suspected lesion are often required to ensure the complete removal of the cancer. The number of stages (or re-excisions) needed might be reduced to a minimum since the sensor would be able to detect the actual limit of the tumor more accurately than a visual assessment of the cancer, therefore allowing the surgeon to draw the cancer limit more precisely from the beginning. Such an embodiment reduces the duration of the procedure as well as the risk for potential disfigurement in sensitive regions and the risk of tumor recurrence.

In one embodiment, the system operates within the safe microwave region at about 4.75 GHz and utilizes the microstrip technology. The adoption of the microstrip design significantly reduces the cost of the system in comparison to other technologies that utilize waveguides, coaxial probes, and radars. In addition, the frequency of operation, being within the microwave range, results in a significantly reduced design cost of the RF components required for the wave analyzer system when compared to the design cost of components that operate at mm-wave frequencies and beyond.

Another embodiment relies on the fact that the proposed system is portable and operates in real-time. In addition to the miniature sensor size, the wave analyzer circuit that generates and analyzes the transmitted and reflected EM waves is extremely compact and permits instantaneous and accurate data processing. This wave analyzer is custom-made, and it overcomes the size, power, and cost constraints of a traditional vector network analyzer (VNA) that is typically used in providing such functionality in order to generate and analyze the transmitted and reflected signals. Hence, in addition to providing a highly sensitive EM sensor, an alternative wave analyzer is disclosed that achieves excellent performance characteristics suitable for integration within portable and compact medical devices.

Vector Network Analyzer (VNA) and Scattering Parameters (S-Parameters)

A VNA is one of the most essential instruments in any environment dealing with high-frequency devices. Primarily, VNAs are used to evaluate the performance of numerous RF devices, such as antennas, filters, amplifiers, among others. Within the numerous evaluation options offered by VNAs, they are most commonly used to measure the S-parameters of devices in order to understand their electrical response to high frequency stimuli. Notably, quantities such as the reflection coefficient, known as the $S_{11}$, and the transmission coefficient, known as the $S_{21}$ comprise a large portion of measurements done through a VNA. Since the application deals with a one-port device, being the sensor, the discussion of parameters other than the $S_{11}$ are beyond the scope here. Generally, a VNA includes circuitry with the purpose of generating high-frequency signals, devices that couple (sample) portions of incident and reflected waves, receiver chains, and embedded computers to process and display the required parameters. The $S_{11}$ is a measure of how much power is reflected off a device under test (DUT) at certain frequencies. In one embodiment, the frequency-response measurement capabilities of the VNA are concerned. As such, the VNA measures the $S_{11}$ by sweeping high frequency signals within a specified range and measuring the properties (frequency, amplitude, and phase) of the signal being reflected from a DUT. In the context of this embodiment, the DUT is the sensor, and the properties of the signal being reflected from the sensor—which are altered due to the presence of a specimen such as cancer—are measured by the VNA to form the basis of the analysis.

An electromagnetics (EM)-based diagnostics and monitoring system for the non-Invasive diagnosis and monitoring of in-vivo and ex-vivo Skin Anomalies Using Lesion-Optimized Sensor System Design and Topology is disclosed. Applications include but not limited to, skin cancer and other disease detection.

The EM-based system utilizes a plurality of components operating within a radio-frequency portion of the spectrum from about 30 MHz to about 300 GHz, applying a compact integrated circuit, a sensor, and a printed circuit board. The sensor includes a plurality of components that operate in one or more of the Ultra high frequency (UHF), microwave, mm-wave and THz regions of the spectrum.

The EM-based system comprises the synthesis of radio-frequency signals, energizes one or more EM sensors that interact with a specimen under test, captures incident and reflected waves through the EM sensor, performs signal processing operations at RadioFrequency (RF) and low frequencies (Filtering, Coupling, Amplification, Attenuation, and Down-conversion), processes and collects the obtained data and applies learning algorithms to extract deep insights into the constituency, characteristics and properties of the specimen under test.

In one embodiment, the specimen under test can be an in-vivo or ex-vivo skin anomaly including but not limited to skin cancer, benign tumors, or other skin diseases. The EM-based system provides diagnostic decisions based on the collected response through the EM sensor(s) in terms of measured incident, reflected and transmitted wave properties including but not limited to S-parameters response. The EM-based system comprises a plurality of features including magnitude and phase measurements of the S-parameters at multiple frequencies. The EM-based system comprises using subsequent measurements to monitor the state progression of skin condition.

In one embodiment, the EM-based system comprises one or more highly sensitive EM sensors, a compact custom-made novel wave analyzer device, a centralized database, and the accompanying data processing and machine learning algorithms. The EM sensors comprises an electromagnetic structure such as an antenna, a resonator, a filter or other passive or active RF devices to emanate, transmit or manipulate electromagnetic waves. The EM sensors are specifically designed to sense electromagnetic differences in in-vivo and ex-vivo skin conditions such as the specimens under test. The EM sensor can have one-port or a plurality of ports to sense the electromagnetic differences of the specimens under test.

In one embodiment, an EM sensor 100 is compact and is operably disposed on a microstrip 102, as shown in FIG. 1A. The EM sensor 100 comprises a dielectric substrate 110, a lesion optimized sensing tip on a cylindrical substrate 120, a $\lambda/2$ resonant element 130, at least two matching stubs 140, and a matching section 150, and a feeding line 160. The lesion optimized sensing tip 120 is operably coupled with the $\lambda/2$ resonant element, the $\lambda/2$ resonant element is operably coupled with the at least two matching stubs 140, the at least two matching stubs 140 is operably coupled with the matching section 150, the matching section 150 is operably coupled with the feeding line 160. The EM sensor comprises a metallic enclosure 200 surrounding the EM sensor 100 and a foam compartment 210 on the distal end of the metallic enclosure. The cylindrical substrate 110 includes a diameter D1 and the microstrip includes a length L1. In one embodiment, the chosen microstrip element's length L1 designates operation within the microwave frequency range, as shown FIG. 1A. In one embodiment, length L1 may be between about 1.0 cm and about 5.0 cm, alternatively, between about 3.0 cm and about 4.0 cm, alternatively, between about 3.2 cm and about 3.8 cm. In one embodiment, the length L1 is about 3.7 cm.

In one embodiment, the EM sensor 100 is characterized by the inclusion of one or more matching sections 150 that enable impedance matching between the source impedance and the sensor's input impedance, as shown FIG. 1A. In one embodiment, the one or more matching sections is between about 30 ohm and 60 ohm, alternatively, between about 40 ohm and 50 ohm, alternatively, between about 42 ohm and 48 ohm. In one embodiment, the one or more matching sections is about 45 ohm.

In one embodiment, the EM sensor 100 is a one-port device with a single opening along the foam compartment 210, as shown in FIG. 1A. The EM sensor 100 can utilize air substrates as well as other dielectric materials with varying dielectric properties. Dielectric materials can have a dielectric constant ranging from about 1 to about 10.

Figure 2:
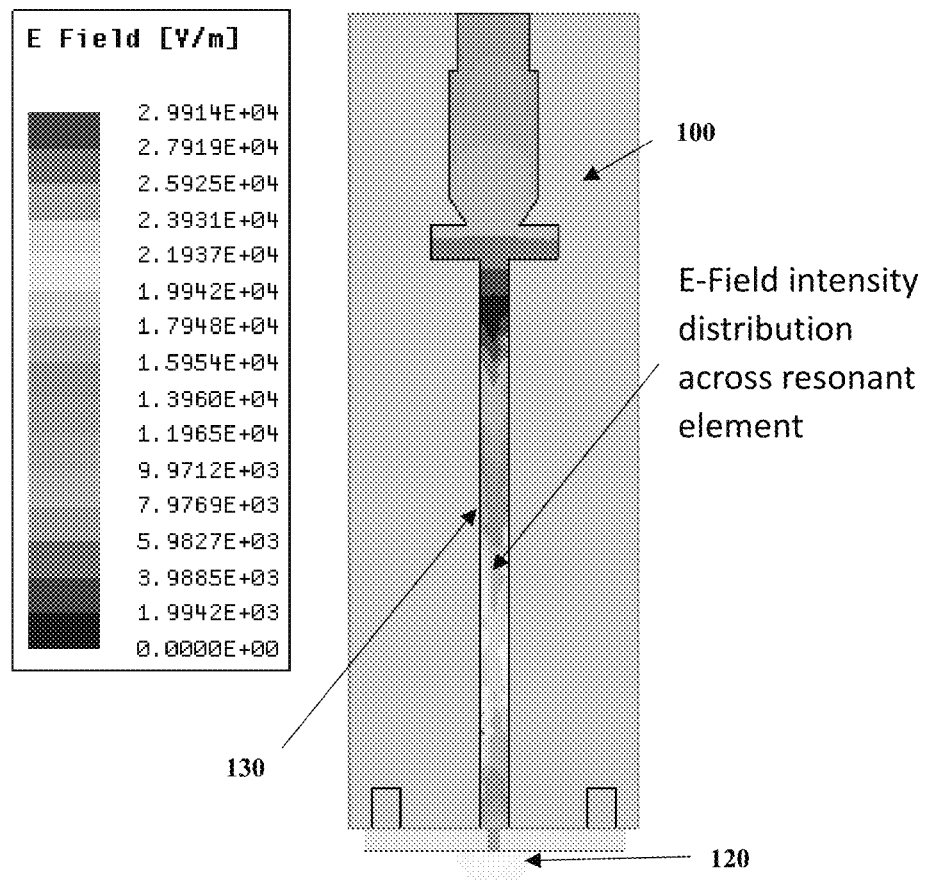
FIG. 2 is a graph of the E-Field intensity across the resonant element of the EM sensor.
Figure 3:
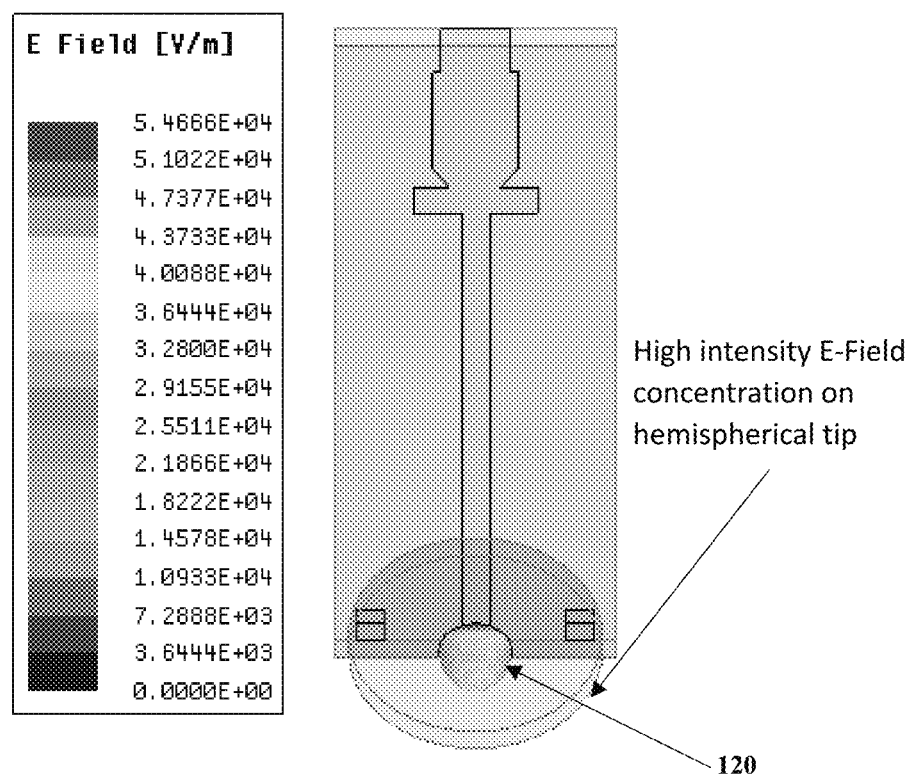
FIG. 3 is a graph of the E-Field intensity on the lesion-optimized hemispherical sensing tip of the EM sensor.

In one embodiment, the EM sensor 100 includes the lesion-optimized sensing tip 120 with a lesion optimized topology that can resemble any shape or form. In one embodiment, the lesion-optimized sensing tip 120 is characterized by a geometrical shape that heightens sensitivity to small lesions and minimizes interactions with undesired regions surrounding the lesion. In one embodiment, the lesion-optimized sensing tip comprises a hemisphere, and is a hemispherical sensing tip, as shown in FIG. 1A. The geometrical shape improves the overall sensitivity by enhancing the sensor's interaction with the specimen under test in terms of sensing field concentration and density, as shown in FIG. 2 and FIG. 3 and minimizing the interaction with undesired regions surrounding the lesion due its optimized topology. The E-Field intensity distribution across resonant element 130 is between about 9.9712E+03 V/m and about 1.9942E+04 V/m. The High intensity E-Field concentration on hemispherical tip is between about 3.6444E+04 V/m and about 4.3733E+04 V/m.

Figure 5:
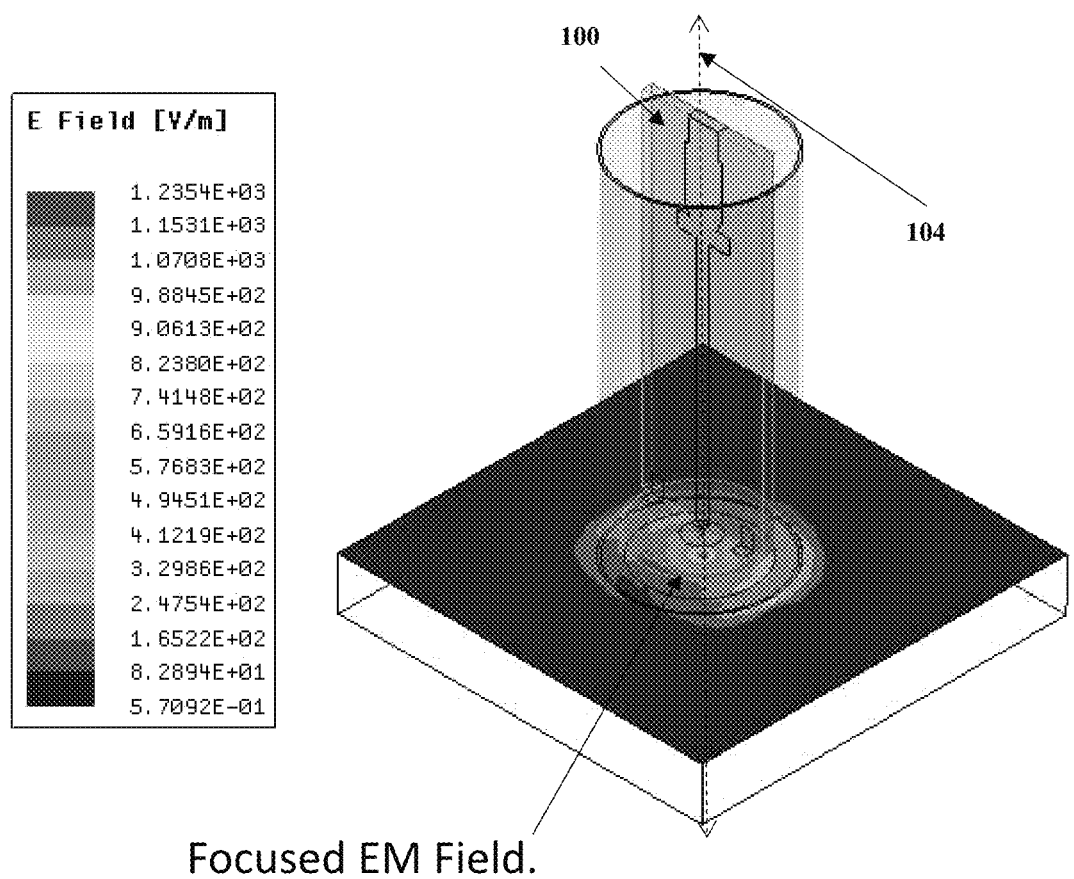
FIG. 5 is the focused E-Field emanating from the lesion-optimized hemispherical sensing tip onto the underlying specimen of skin within an electromagnetics simulator.
Figure 6:
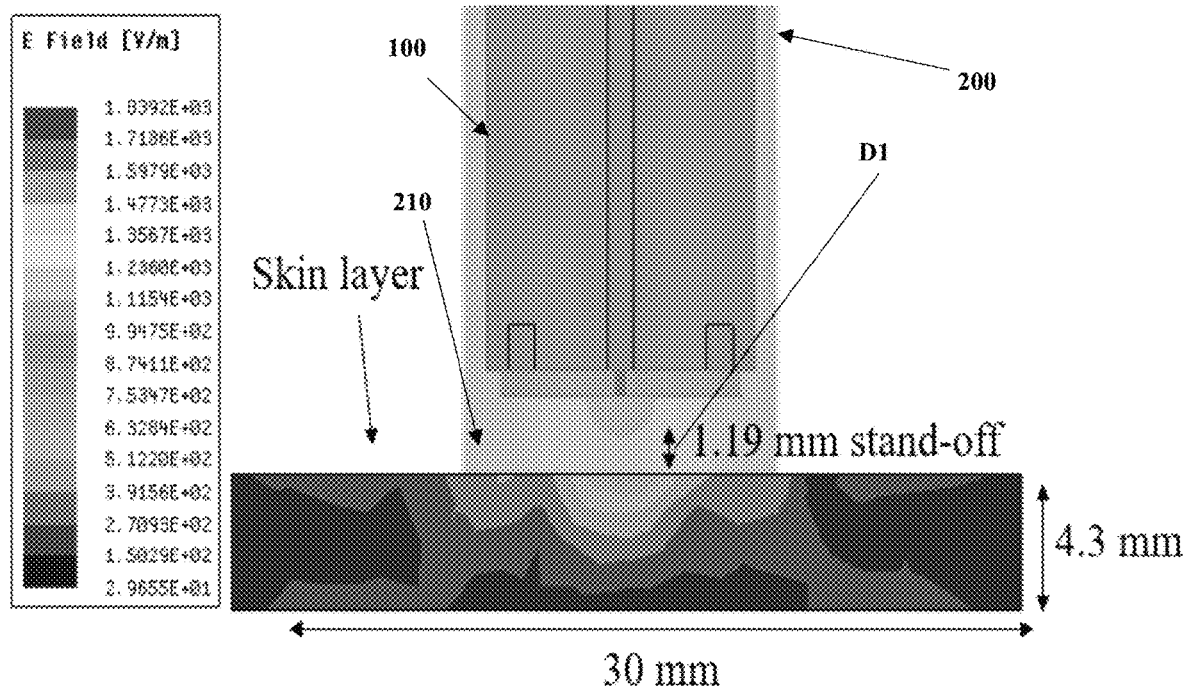
FIG. 6 is the E-Field intensity within a skin sample at a sensor stand-off distance of 1.9 mm.

The geometrical shape exhibits a small radius dimension for the hemispherical sensing tip 120 and this enables measurements of small specimen under test (tumors) with heightened resolution even for the smallest tumors or lesions of comparable dimensions as the sensing tip, as shown in FIG. 3. In one embodiment, the radius dimension is about 0.5 mm and alternatively, the radium dimension is between about 0.1 mm to about 1 mm, which caters for different lesion sizes. FIG. 2 illustrates the E-field intensity distribution along the sensor, and FIG. 3 demonstrates the concentration of the E-field at the hemispherical sensing tip. Moreover, FIG. 5 demonstrates the illumination region directly underneath the sensing tip, with the region of maximum sensitivity highlighted in red. This enhanced concentration of the EM field in a focused illumination region enables adjustable penetration depth into the SUT. For example, FIG. 6 illustrates the EM penetration depth within an about 4.3 mm sample at a separation distance of 1.19 mm and 0.6 mm respectively, where the smaller separation distance results in deeper EM fields penetration. Furthermore, the geometry of the hemispherical tip optimally adapts to the lesion topology, suiting the natural geometry of the anomaly by adopting a hemispherical sensing tip of about 1 mm diameter that enables a high sensing resolution for small cancerous lesions, which are typically larger than about 1.5 mm. When this sensor is positioned directly above a SUT, the interaction of the EM-fields emanating from the hemispherical tip with the SUT is maximized. This interaction between the EM-fields and the SUT manifests itself as a unique response from the sensor upon the perturbation of its concentrated fields by the nature and composition of the SUT. The sensor's frequency of operation, as well as the magnitude and phase of the reflection coefficient (Su) are uniquely altered, which echoes the distinct properties of the SUT (whether a cancerous or healthy one), also known as dielectric properties. The interaction between EM waves and a SUT of specific dielectric properties, as well as the definition of the measured quantity (Su), indicated below.

Interaction of Electromagnetic Waves with Skin of Varying Dielectric Properties

The fact that skin possesses electrical properties, such as the permittivity, this can alter the behavior of electromagnetic structures, such as sensors. Such sensors generate electromagnetic fields that are perturbed by the presence of a specimen under test of a characteristic permittivity, such as skin, which is represented by a change in the sensor's response. Hence, the nature of the specimen under test is studied by observing the change in the sensor's response since it is a direct indicator of the specimen's properties. Similarly, variations in the permittivity of skin due to several factors, such as disease, humidity, and dryness also cause the response of the sensor to shift from a baseline corresponding to healthy skin. Throughout the literature, it has been proven that alterations such as cancer change the dielectric properties of skin, and hence, cause the behavior of a sensing structure to shift accordingly. Through such shifts and the associated trends, one can ultimately conclude characteristics that are representative of a disease, such as cancer. A plethora of work in the literature has verified that, indeed, statistically significant dielectric differences are present between healthy, benign, and cancerous skin, allowing for the conception of methods that aim to diagnose skin cancer by means of electromagnetic technology. For one example, an ultra-wide-bandwidth study of the dielectric properties of freshly excised healthy skin as well as malignant tissues such as BCC and SCC cancers was executed. The experiment is carried out by means of a typical open-ended coaxial probe as the electromagnetic structure performing the measurement. Primarily, the cancer increased water content within malignant tissues. After analyzing the dielectric properties of these excisions, the existence of statistically significant differences in the dielectric properties of malignant and healthy tissues. Also, water content within BCC and SCC was the primary cause of variation in the dielectric properties. Furthermore, the embodiments disclosed herein illustrates the powerful ability of EM waves to differentiate between healthy and malignant tissues by relying on a ultra-wideband synethic imaging system. The system is tested on excised BCC and SCC cancers, and is able to differentiate between cancerous and healthy skin based on their electromagnetic reflectivity. A comprehensive list of dielectric properties and models can be readily obtained.

Electrically, biological materials such as skin, blood, among other tissues, possess a parameter known as the complex permittivity. This permittivity dictates how a material, on a particle level, behaves when exposed to an electric field. The permittivity is typically given by $\varepsilon_r = \varepsilon_r' - j\varepsilon_r''$, where the real part $\varepsilon_r'$ is defined as the dielectric constant, and the complex part $\varepsilon_r''$ is defined as the dielectric loss factor. Research within the literature has shown that the permittivity of tissues is altered depending on several factors, and particularly, whether the tissue is cancerous or not. Such differences are caused by the composition of the material under test.

In addition, this complex permittivity undergoes processes known as dispersion and relaxation. Dispersion is the change of the complex permittivity as a function of frequency, which occurs due to the interaction of the electric field with different constituents within the material under test. For example, three primary dispersion regions for biological tissues have been characterized in the literature, $\alpha$, $\beta$, and $\gamma$. The variation of the permittivity within each of these regions is governed by physiological and chemical phenomena within the tissue. At lower frequencies, the $\alpha$ and $\beta$ dispersions are dominant, where the permittivity is mostly affected by the cellular membrane, surface conductance, and the cellular structure. On the other hand, the change of permittivity within the gamma dispersion region is governed by the water and protein content of the material under test. Permittivity is typically approximated by the Debye model (1), where $\varepsilon_\infty$ defines the permittivity at the high frequency limit, $\varepsilon_s$ is the permittivity at low frequencies, $\tau$ is the relaxation time, and $\omega$ is the angular frequency.

$$\varepsilon_r = \varepsilon_\infty + \frac{\varepsilon_s - \varepsilon_\infty}{1 + jw\tau} \quad (1)$$

The plot in FIG. 1D also shows an abstract illustration of the behavior of both the real and imaginary parts of the complex permittivity of tissues as a function of frequency. Fundamentally, dispersion occurs due to the fact that particles within a material under test that is exposed to an electric field become polarized, causing a change in the total charge distribution. This polarization action necessitates that the particle orientation arrives at a new equilibrium, consuming an amount of time equivalent to the relaxation time τ. The different constituents within the material under test are characterized by different relaxation times, which equivalently affect their permittivity, which also affects the sensor's performance and therefore enables the differentiation between homogeneous (healthy) and heterogeneous skin (cancerous).

Additionally, a metallic shield is designed and fabricated to the dimensions of the sensor (FIG. 1A, FIG. 1C), which grants the sensor immunity to environmental RF noise such as WiFi signals among others, and it also provides a stable fixture that maintains the desired separation distance. The metallic shield is a conductive enclosure, which prevents interaction with the ambient electromagnetic waves while simultaneously thwarting sensing from undesired regions. This enclosure includes a cutout at the sensing tip's location, where desired sensing will be performed. Furthermore, the shield incorporates a region that fits a hard-foam spacer between the sensing tip and the SUT. Hence, a fixed separation distance is ensured, and the flatness of the underlying skin is preserved.

In one embodiment, the sensor's operation within the microwave region of the frequency spectrum (~4.75 GHz), a form of non-ionizing radiation, ensures the safety of the technique when compared to other forms of radiation such as X-rays[36], [37]. Accordingly, the sensor also adheres to the regulations adopted by the Federal Commissions Committee (FCC) to limit radiation emission levels ANSI/IEEE C95.1-1992 [38]. Specifically, the adopted standard sets an upper limit of about 1.6 W/Kg for the metric known as the Specific Absorption Ratio (SAR), which is the upper limit on how much EM radiation a volume of tissue can safely absorb. The sensor achieves a peak SAR of about 0.1 W/Kg at its operational input power of about −15 dBm, which is well below the critical SAR threshold.

Figure 4A:
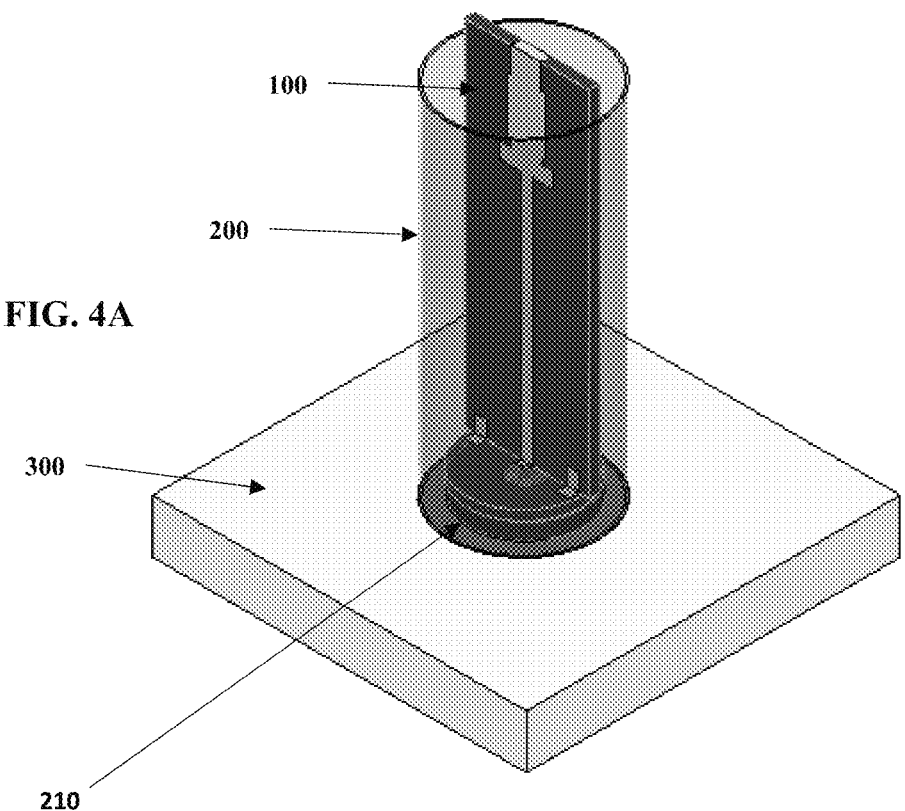
FIG. 4A is a perspective view of the Lesion-Optimized Sensor on top of a skin sample within an electromagnetics simulator.
Figure 4B:
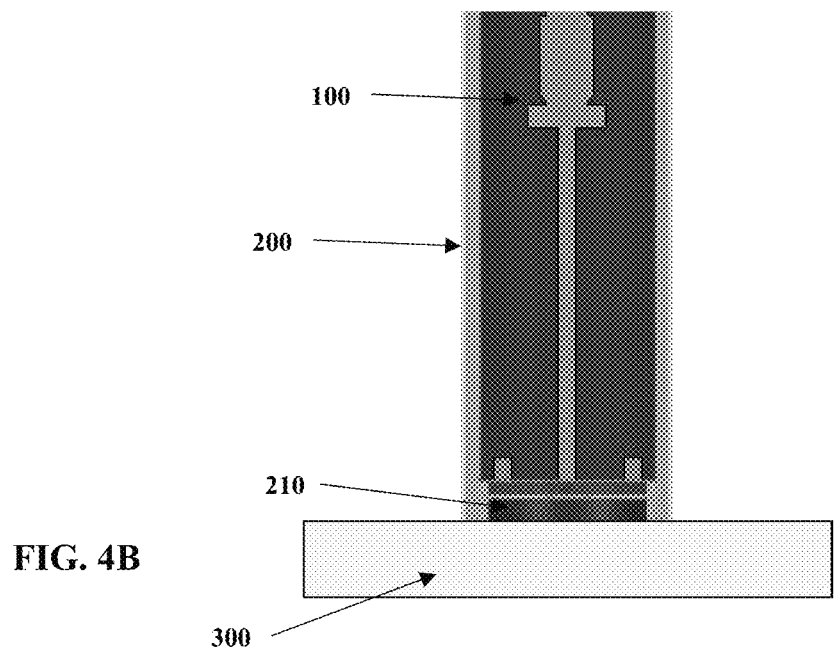
FIG. 4B is a side view of the Sensor on top of a skin sample within an electromagnetics simulator.

The optimized sensing tip is characterized by a concentrated field density at the hemispherical sensing tip 120 and this enables a practical stand-off distance D1 from the specimen under test allowing placement of a foam separator 210 between the sensor 100 and specimen 300, as shown FIGS. 4A-4B. The foam separator 210 guarantees that the sensor 100 is operating in the near field without attenuating the signal. The foam-loaded enclosure 200 maintains skin flatness and a practical stand-off. In this embodiment, skin flatness highlights that there is no bending of the skin. The enhanced standoff distance enables minimizing signal penetration into layers beneath the targeted lesion and hence focuses signal solely on the specimen under test, as shown in FIG. 5. The focused EM field is focused along the longitudinal axis 104 of the EM sensor 100 and is between about 1.2354E+03 V/m and about 1.0708E+03 V/m.

The EM sensor 100 is shielded with an enclosure 200 that provides immunity to ambient RF noise, FIGS. 1A-1C. The EM sensor in is shielded with an enclosure 200 that provides immunity to sensing from unintended locations on the sensor such as response from handling the sensor. The geometrical shape of the enclosure 200 allows for practical standoff distance in conjunction with the enclosure 200 enables a practical, adjustable, and modifiable form factor that preserves flatness of specimen under test without bending or sinking. The geometrical shape of the enclosure 200 further minimizes interference from underlying layers especially when specimen under test is thin and flexible.

Figure 7:
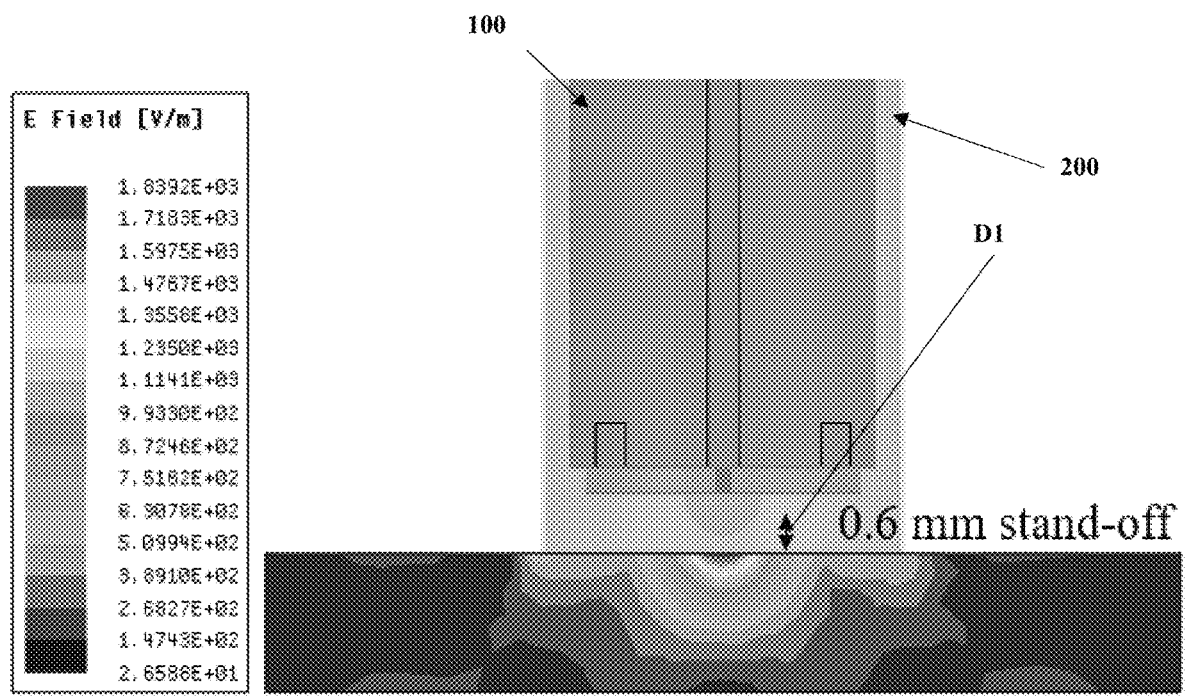
FIG. 7 is the higher E-Field intensity within a skin sample at an adjusted stand-off distance of 0.6 mm.

The characteristics of the enclosure 200 enable an adjustable separation distance D1 between the foam separator 210 and the specimen under test allowing targeting different skin anatomies, as shown in FIG. 6 and FIG. 7. In one embodiment, the separation distance D1 is between about 0.20 mm and about 1.80 mm, alternatively, between about 0.40 mm and about 1.40 mm, alternatively, between about 0.60 mm and about 1.20 mm. In one particular embodiment the distance can be modified by at least about 0.59 mm to target the temple as opposed to the cheek. In another embodiment, the distance D1 can be adjusted in order to optimize the depth of penetration at the area of coverage, FIG. 6 and FIG. 7. The depth of penetration is between about 0.01 mm and about 4.0 mm, alternatively, between about 0.10 mm and about 3.0 mm.

Figure 8:
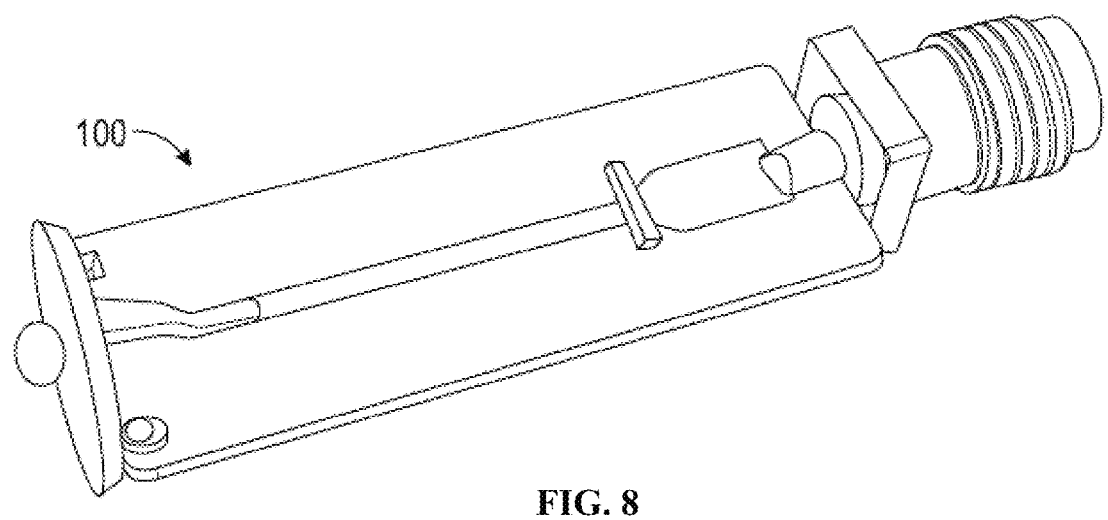
FIG. 8 is a photograph of the fabricated embodiment of the EM sensor, according to one embodiment.
Figure 9:
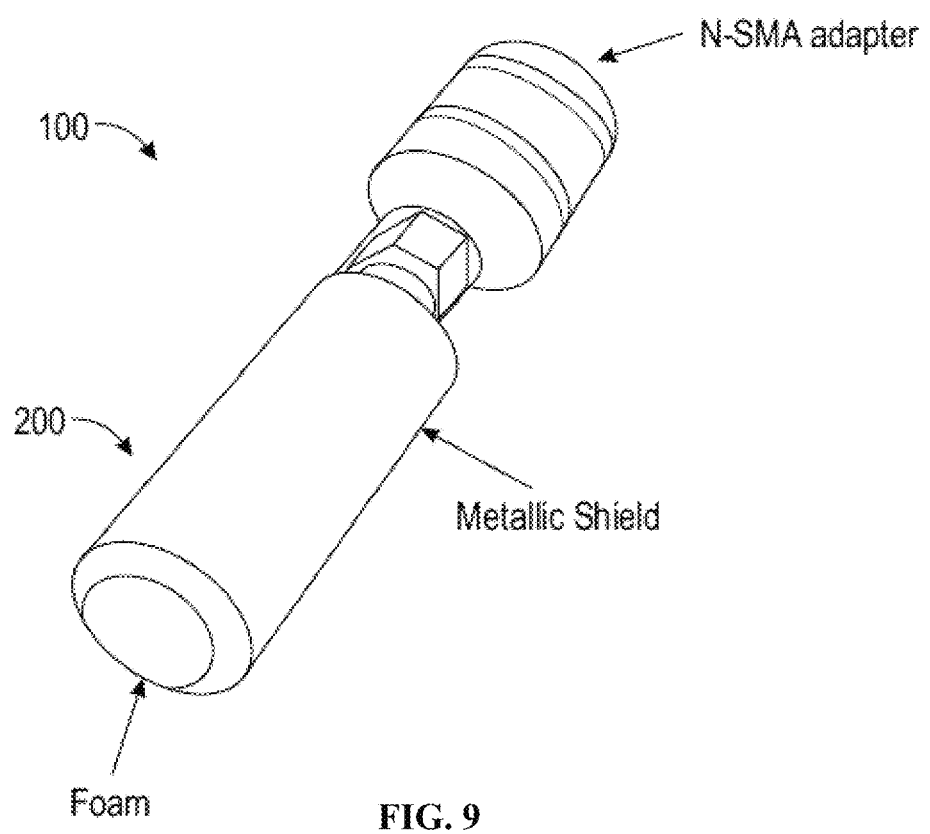
FIG. 9 is a photograph of the fabricated embodiment of the EM sensor of FIG. 8 within a metallic enclosure.
Figure 10:
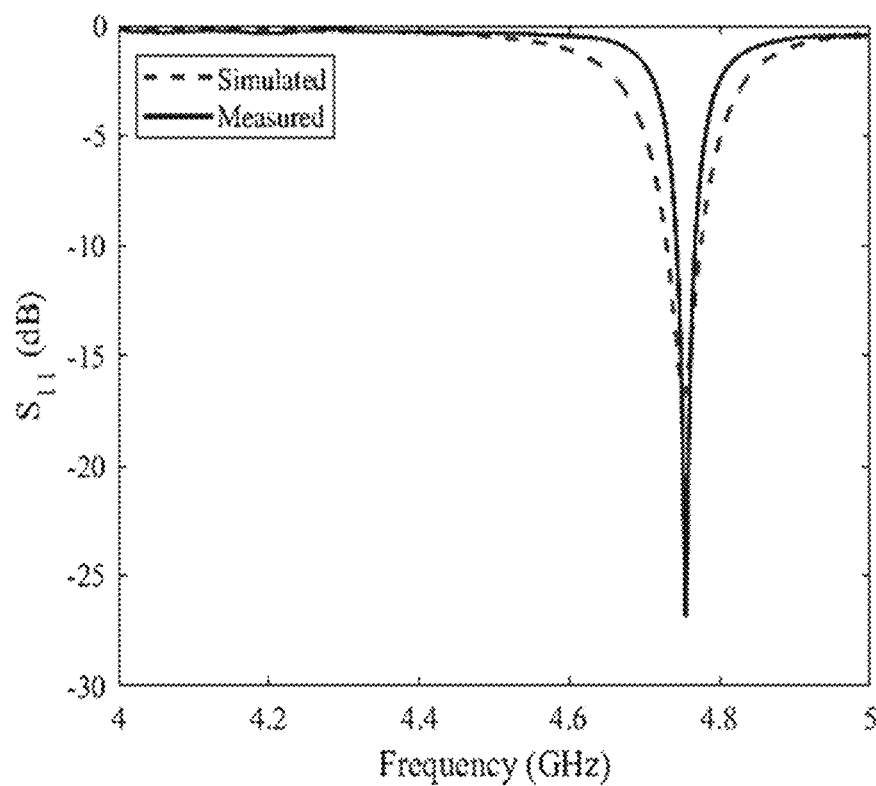
FIG. 10 is a graph of the reflection coefficient response of a sensor as shown in FIGS. 8-9.

As shown in FIG. 8, the EM sensor 100 is fabricated on a substrate and fitted within a metallic enclosure 200, as shown in FIG. 9. The EM sensor 100 in this embodiment operates within the microwave region at about 4.75 GHz. The measured and simulated $S_{11}$ response of the sensor are shown in FIG. 10.

Figure 11A:
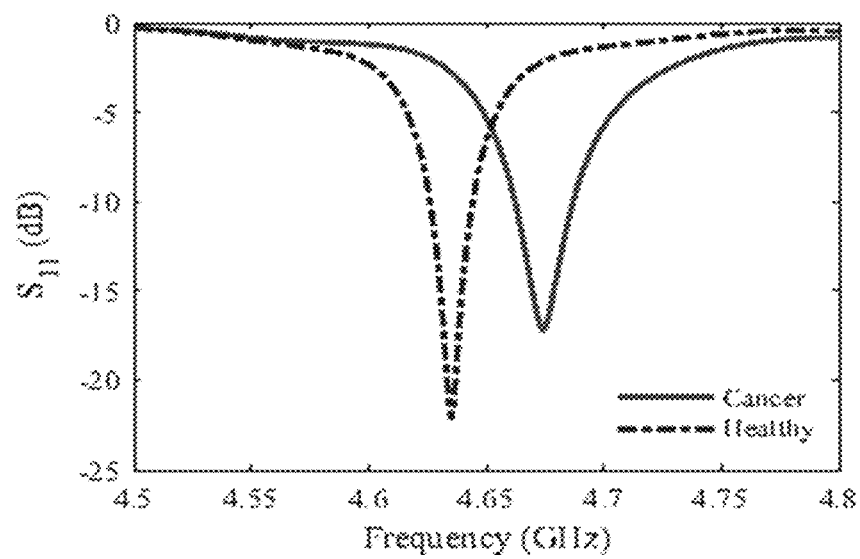
FIGS. 11A-11L are graphs of the EM system's S-parameter response (magnitude and phase) to patients and healthy volunteers.
Figure 11B:
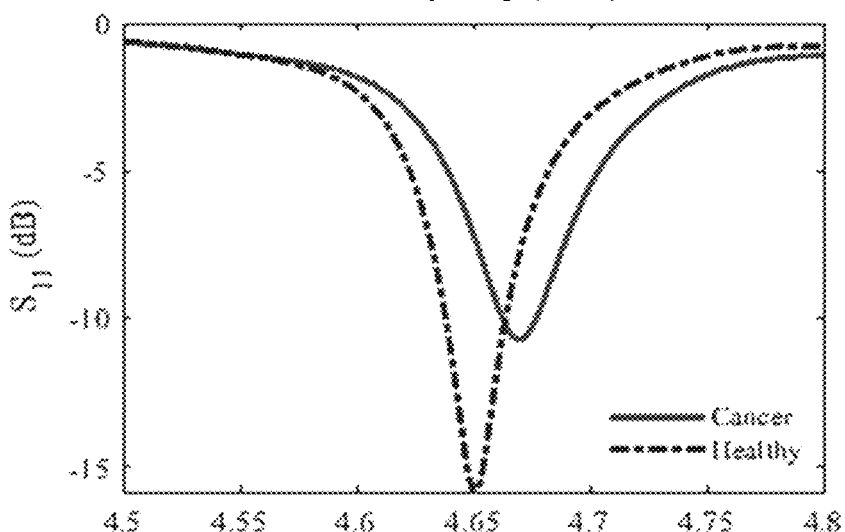
Figure 11C:
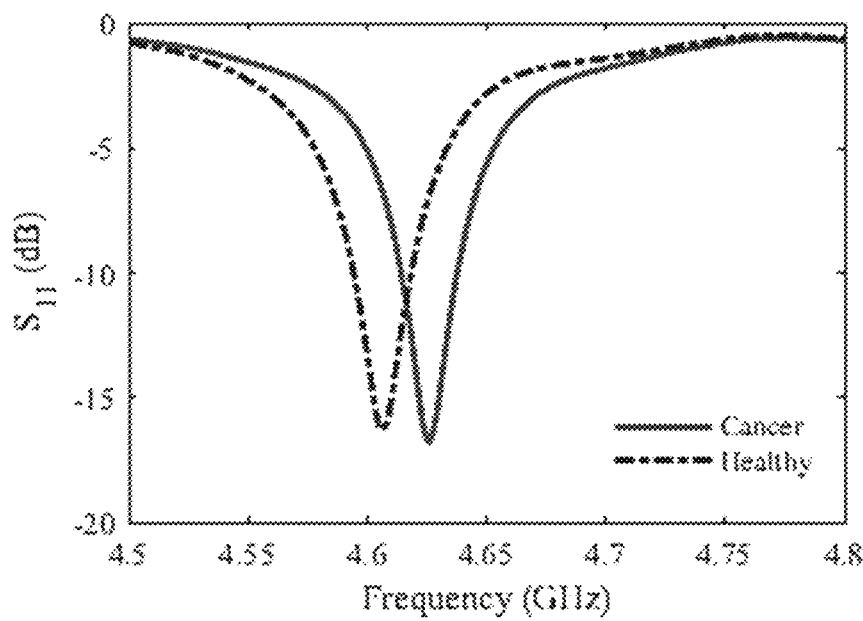
Figure 11D:
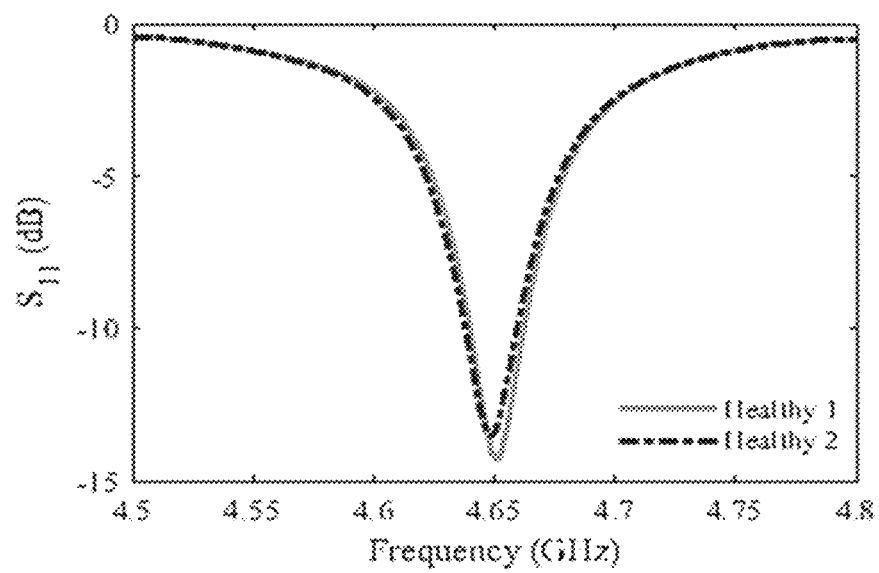
Figure 11E:
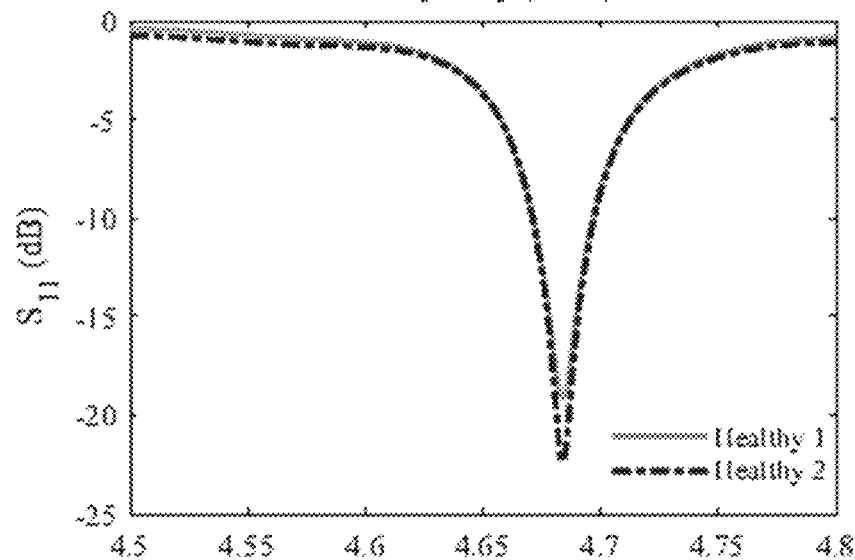
Figure 11F:
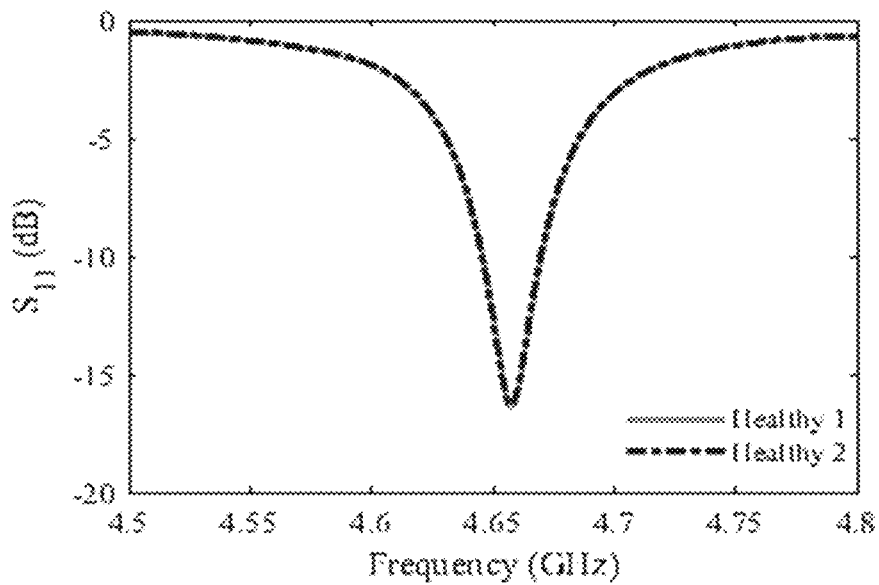
Figure 11G:
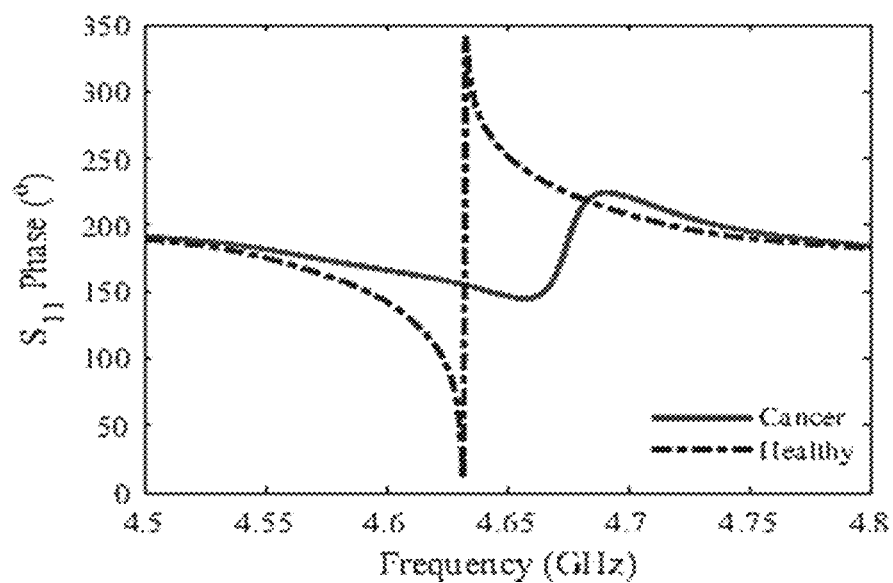
Figure 11H:
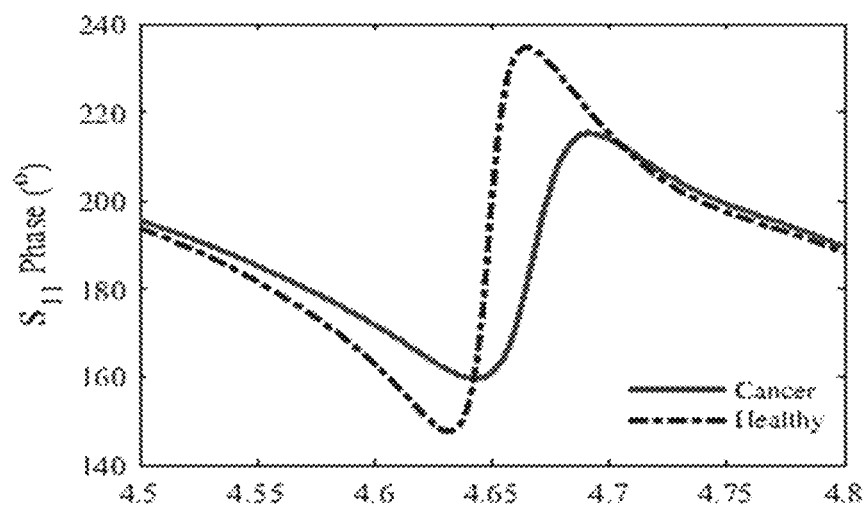
Figure 11I:
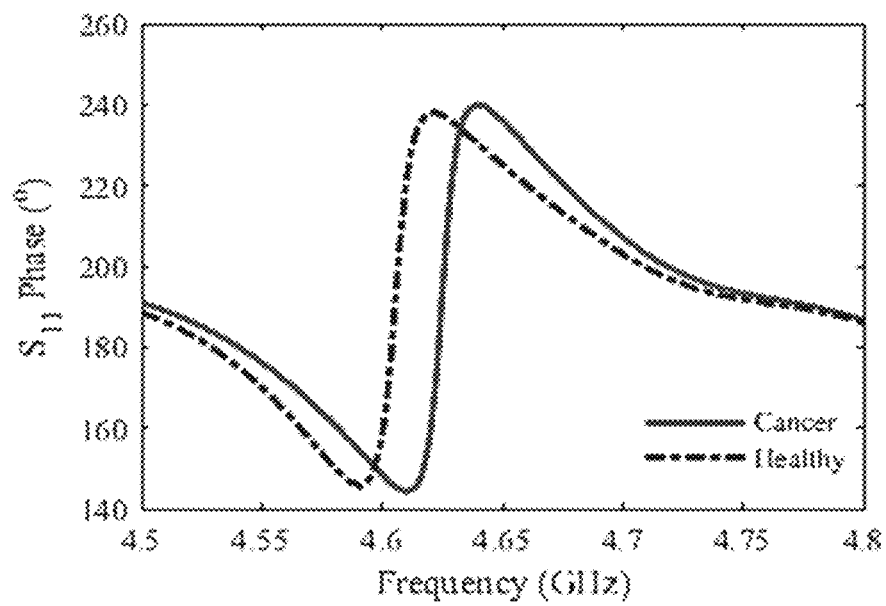

The variation in the $S_{11}$ response of the sensor shown in FIGS. 8-9 upon loading with healthy and cancerous lesions from patients as well as healthy skin from different locations on healthy individuals is shown in FIGS. 11A-11L. FIGS. 11A-11C corresponds to the $S_{11}$ magnitude and frequency variation within a patient, for 3 different patients. These changing magnitude and phase values, whether for cancer patients or healthy individuals, are analyzed at every frequency in order to develop the classification model. To illustrate these changes, one point (the trough of each curve) is highlighted. The entire range is taken and the algorithm is applied on it to take into consideration every single point within the range. A shift in the operational frequency, and a shift in the $S_{11}$ magnitude as well as a shift in the $S_{11}$ phase is used. For example, FIG. 11a shows the $S_{11}$ magnitude response of the sensor at the trough, being about −15 dB and a frequency at about 4.7 GHz compared to the shifts from the healthy skin measurements with an $S_{11}$ magnitude of about −23 dB and a frequency measurement of about 4.64 GHz. Similarly, FIG. 11b shows the skin cancer $S_{11}$ magnitude measurement at about −10 dB and a frequency of about 4.68 GHz compared to healthy skin measurement having a magnitude of about −15 dB and a frequency of about 4.65 GHz. Also, FIG. 11c shows the skin cancer patient measurement with an $S_{11}$ magnitude at about −16 dB and a frequency shift to about 4.63 GHz compared to healthy skin with a $S_{11}$ magnitude of about-15 dB and a frequency measurement of about 4.60 GHz. FIGS. 11D-11F correspond to the $S_{11}$ magnitude and frequency variation within a healthy individual, for 3 different individuals. FIGS. 11g-11i corresponds to the $S_{11}$ phase and frequency variation within a patient, for 3 different patients. FIG. 11g shows the skin cancer patient included a $S_{11}$ phase shift between about 150 to about 240(°) and a frequency shift between about 4.66 GHz to about 4.69 GHz compared to healthy skin with a $S_{11}$ phase between about 15 and about 350(°) with a frequency measurement between about 4.63 and about 4.64 GHz. FIG.

Figure 11J:
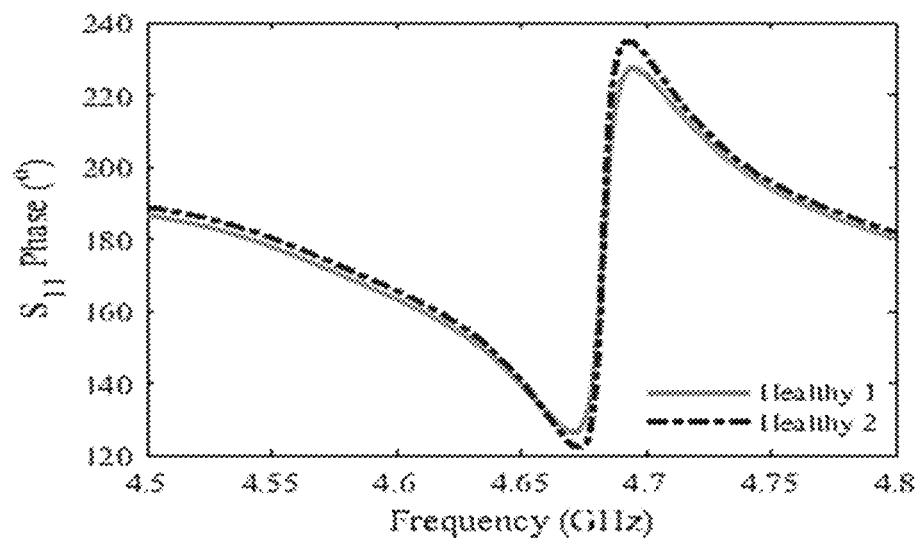
Figure 11K:
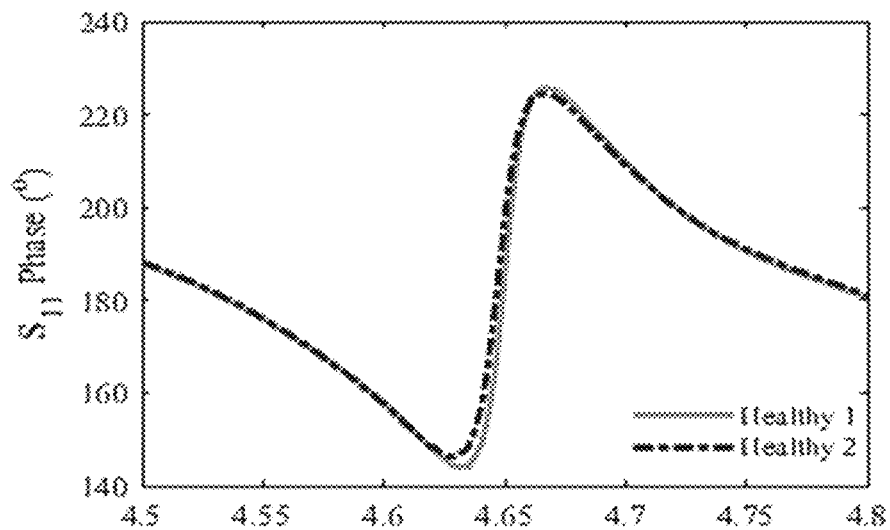
Figure 11L:
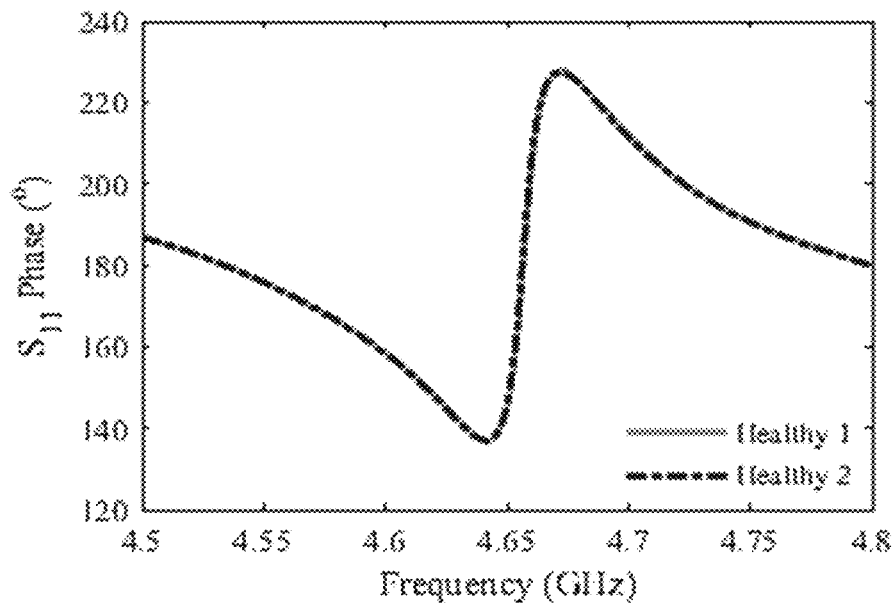

11h shows the skin cancer patient included a $S_{11}$ phase shift between about 160 to about 215(°) and a frequency shift between about 4.65 and about 4.70 GHz compared to healthy skin with a $S_{11}$ phase between about 150 and about 335(°) with a frequency measurement between about 4.63 and about 4.68 GHz. FIG. 11i shows the skin cancer patient included a $S_{11}$ phase shift between about 140 to about 240(°) and a frequency shift between about 4.61 and about 4.65 GHz compared to healthy skin with a $S_{11}$ phase between about 140 and about 240(°) with a frequency measurement between about 4.59 and about 4.62 GHz. FIGS. 11J-11L corresponds to the $S_{11}$ phase and frequency variation within a healthy individual, for 3 different health individuals.

The wave analyzer system receives the signal from the EM sensor and can operate in the Microwave frequency range and in the millimeter-wave frequency range. The wave analyzer system comprises a vector network analyzer subsystem, power sensors, time domain analyzers, spectrum analyzers or reflectometers. The wave analyzer includes multiple passive and active RF components to facilitate signal manipulation, including, but not limited to: filters, amplifiers, and attenuators. The wave analyzer utilizes analog and digital filtering techniques to improve the measurement quality. The wave analyzer comprises a plurality of calibration processes, such as open-short-load, or single full reflection loads such as open or short circuits to improve measurement performance and cancel or diminish system errors and losses. The wave analyzer system measures the power of incident or reflected signals as well as the complex reflection and transmission coefficients. The wave analyzer includes an on-board control unit that can be composed of a microcontroller, a microprocessor, a field programmable gate array (FPGA). The wave analyzer can interface with external computational systems including, but not limited personal computers, mobile phones, and tablets. The wave analyzer supports wired and wireless internet connectivity. The wave analyzer supports sharing measurements and processed data with web-based cloud services. The wave analyzer collects and generates data based on patient profiles, and sensor measurements, comprises customizable algorithms that interact with the cloud and the database, can predict the properties of the lesion for a specific category of lesion and patient and/or forward the data to web-based cloud systems for general data modelling enhancement procedures and model updates. The wave analyzer interrogates the sensor, which in turn examines the skin. This wave analyzer generates the stimulus signals sent to the sensor at the front-end, analyzes the reflected signals in the sensing procedure, extracts the Si' magnitude and phase, as well as performs the required input and output (TO) operations to record and process the obtained data. After the skin sensing is complete, the wave analyzer determines whether or not the skin lesion is malignant.

In one embodiment, the wave analyzer system operates from about 2.3 GHz to about 6 GHz. The wave analyzer system measures the sensor's reflection coefficient ($S_{11}$) and executes tailored learning algorithms on the obtained measurements for skin lesion characterization. The signal in the wave analyzer system is initiated by a Source known as the frequency synthesizer. This source is programmed to sweep and output a specific range of frequencies encompassing a sensor's frequency of operation. The output of the source is connected to two devices known as directional couplers whose purpose is to couple portions of the incident and reflected signals propagating towards and from the sensor, respectively. These two coupled signals are of high frequency content and must be down-converted to enable more convenient processing. Consequently, two devices, known as mixers, down-convert the reflected and incident waves simultaneously to a lower intermediate frequency (IF). For these mixers to operate, another source, labeled as the Local Oscillator (LO) must be used to drive their operation. As a result, two IFs of about 40 MHz are obtained at the output of the two mixers, which are then filtered by low-pass filters to block unwanted harmonics and intermodulation products from propagating into the detectors. Finally, the specialized signal detectors output the magnitude and phase of the difference of these signals and feed them into a microcontroller that performs the needed digital processing and executes the relevant learning algorithms and prediction procedures. Component microwave structure definitions, functionality, and other details are detailed below.

Figure 12A:
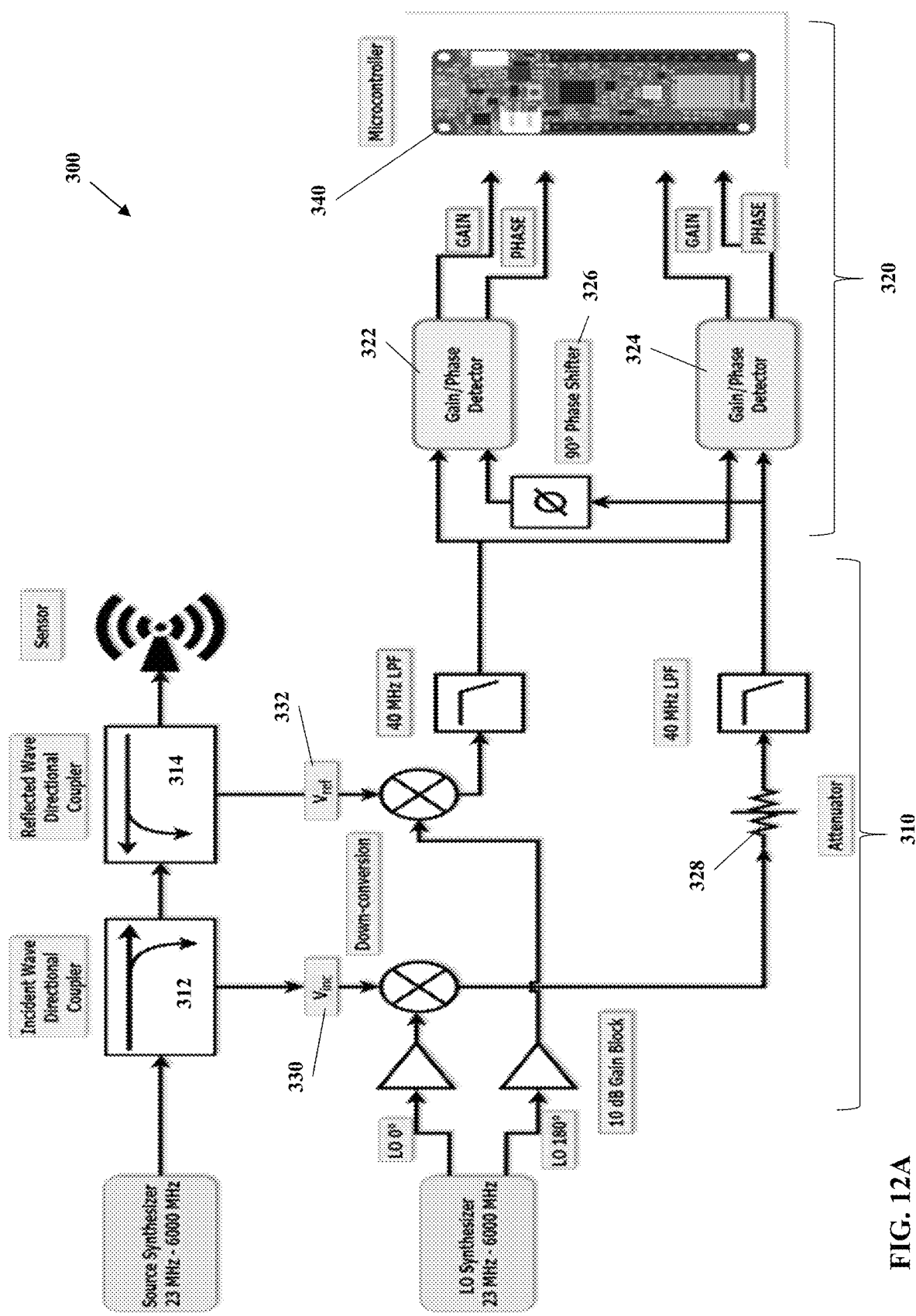
FIG. 12A is a schematic of the Wave Analyzer System architecture, an embodiment of the wave analyzer system, according to one embodiment.

The functional diagram of the wave analyzer system is shown in FIG. 12A. Additionally, the receiver module and the transmitter module acts as the source frequency generator.

Microwave Structures

Directional Coupler

Figure 12B:
FIG. 12B is a schematic of the Directional Coupler.

A directional coupler is a 4-port RF device, illustrated in FIG. 12B, that is essential for the task of sampling (coupling) a specific portion of an incident signal or a reflected one, depending on the configuration. Within the context of measuring the reflection coefficient of the sensor, the directional coupler constitutes the heart of the designed analyzer system. The operation of the directional coupler is as follows: A stimulus signal is provided to port 1, which passes the signal onwards to port 2, which is connected to the sensor. Port 4, known as the isolated port, is typically terminated with a 50-ohm resistor, whereas port 3, defined as the coupled port, outputs a fixed portion of the signal entering port 1. For example, if the input power supplied to port 1 is ~0 dBm, and the coupling factor of the DC is ~10 dB, then the output of port 4 is −10 dBm (~10 dB lower than 0 dBm). Consequently, if two directional couplers are connected in reverse, one would be able to couple portions of the incident signal as well as the reflected signal from the sensor, enabling the sensor to process both simultaneously and extract the desired information. In one architecture, two units of the directional coupler from mini-circuits (ZHDC-10-63+) are used due to the coupler's wideband frequency of operation (~2 GHz-6 GHz) as well as its high directivity (~33 dB).

RF Amplifier

RF amplifiers are electronic circuits used to increase the power of a signal by a factor known as the gain. In the context of the analyzer circuit, the RF amplifier increases the power of the LO signals before feeding the mixer, since particular mixers require a high LO power.

Mixer

The RF mixer is a 3-port device that performs fundamental tasks in the realm of electronics and communication applications, specifically within radio transmitters and receivers. Mixers are typically used to change the frequency of an input signal into either a lower one or a higher one, also known as down-conversion and up-conversion respectively. Within transmitters, mixers transform the low-frequency input into a higher one within the RF range that is suitable for the desired type of communication, such as WiFi for example. On the other hand, in receivers, such as in this embodiment, the mixer transforms the high frequency that is reflected from the sensor into a lower frequency that can be easily processed by the consequent digital circuitry. The mixers utilized in the system are two SIM-762H+ units from mini-circuits. These mixers are characterized by a wideband operation (2.3 GHz-6 GHz) and they allow the system to down-convert the high frequencies incoming from the directional couplers to the 40 MHz intermediate frequency.

Filters

Figure 12C:
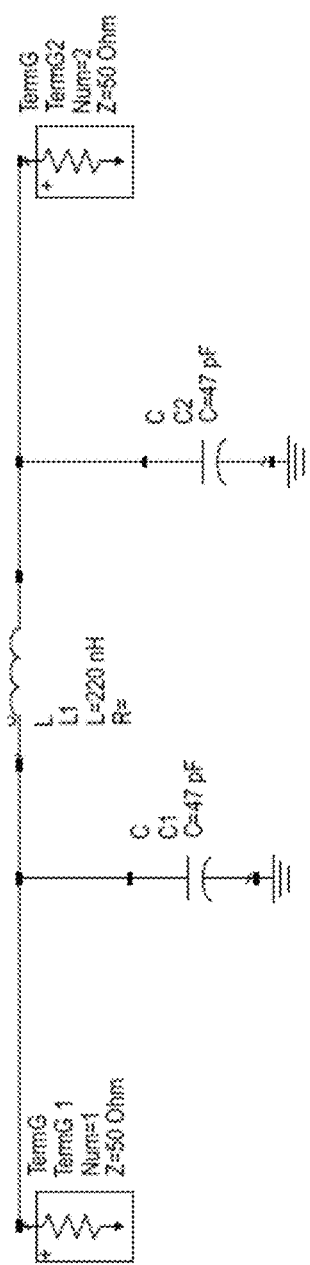
FIG. 12C is an ADS schematic of the 40 MHz LPF.
Figure 12C:
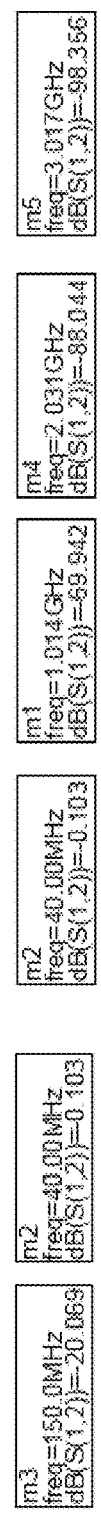
Figure 12D:
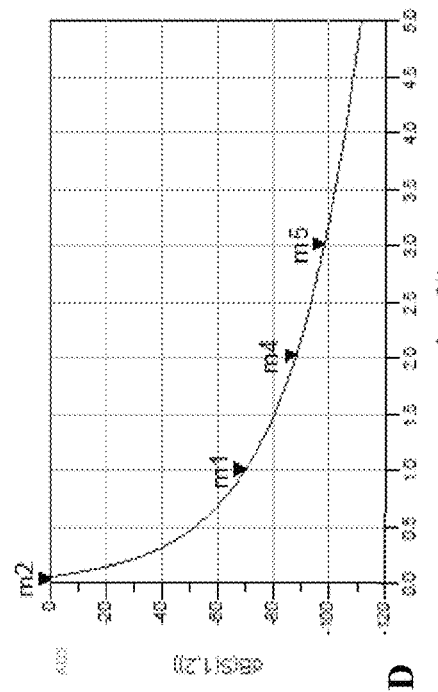
FIG. 12D are graphs of the Simulated results of the LPF at (a) small bandwidth, and (b) large bandwidth.
Figure 12D:
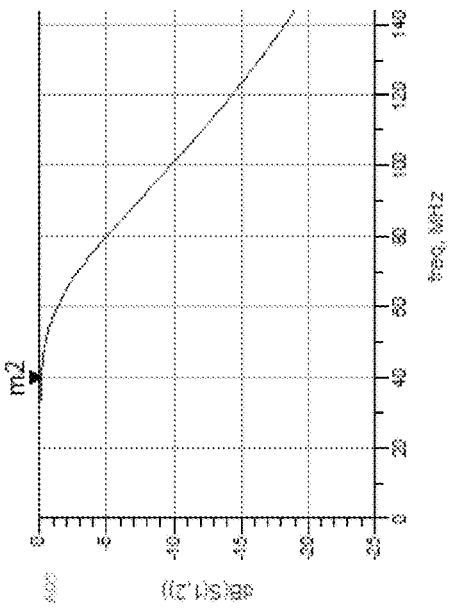

Non-linear components, such as the PLL, Mixer, and Amplifier, introduce new and undesired frequencies into the system, which can compromise the functionality and degrade performance. As a solution to this problem, filters, which are passive RF devices, are used to select the frequencies that are allowed to propagate within the system and the ones to block. Many types of filters exist, primarily, low-pass, high-pass, band-pass, and band-stop filters. The choice of filter is governed by the application at hand. Within the context of one embodiment, low-pass filters are utilized to suppress the harmonics and intermodulation products resulting from frequency synthesis and mixing. Non-linear components such as the synthesizers, mixers, and amplifiers generate additional undesired frequency components that are injected into the detectors. This would critically distort the desired signals and will lead to inaccurate measurements. For this reason, two 40 MHz low-pass filter (LPF) are developed that enable the desired frequencies to pass while preventing the undesired non-linear byproducts from continuing onto the detectors. The filters are designed using Advanced Design System (ADS) and they follow the Pi topology, which is composed of two 47 pF shunt capacitors and a 220 nH series inductor in between. FIG. 12C illustrates the ADS schematic of the filters, and FIG. 12D illustrates their transmission performance, represented as $S_{21}$.

Phase-Locked Loop (PLL) and Voltage-Controlled Oscillator (VCO)

Generating high-frequency signals is fundamental to the operation of the system. Such signals are the stimulus that energizes the sensor and creates the relevant electromagnetic field governing the sensing process. To generate such signals, a programmable PLL is used. Within the PLL, there are multiple VCOs and divider circuits as well as a phase detector, which enable the system to generate a wide range of frequencies while maintaining excellent phase stability. Two PLLs perform the task of generating the stimulus frequency that energizes the sensor and feeds the LO port of the mixer to perform down-conversion. The PLLs used are the MAX2871 from Maxim Integrated. This PLL is characterized by its wideband operation, covering about 23.5 MHz to about 6 GHz. Additionally, the MAX2871 is fully software programmable through a 4-wire SPI interface, which grants the system control over the entirety of the parameters and options dictating its functionality. Moreover, the MAX2871 operates in two modes, the Integer-N and the Fraction-N modes, which allows the system to generate almost any frequency within its range of operation. The full programming sequence can be understood from the datasheet, and an Arduino implementation of the code is applied in one embodiment.

Gain and Phase Detection

In one embodiment, two gain and phase detectors are utilized that will perform the crucial role of measuring the gain and phase difference between two inputs. These two inputs are the down-converted 40 MHz signals corresponding to the incident and reflected signals from the sensor. In other words, the gain and phase detectors will result in the desired parameter of interest, the $S_{11}$. The used detectors are AD8302 units from Analog Devices. The AD8302 operates from DC up to about 2.7 GHz, and it is capable of measuring signals with a power level as low as −60 dBm. Additionally, the AD8302 is capable of measuring a maximum gain and a loss of 30 dB, meaning that the maximum $S_{11}$ that could be measured is also 30 dB. On the other hand, the AD8302 is capable of measuring the 0-180° phase between the two inputs. To perform such measurements, the AD8302 outputs the gain and phase values as DC voltages across the gain and phase output pins. The AD8302 expresses the gain as ~30 mV/dB, and the phase as ~10 mV/°, both of which can be easily read by a microcontroller.

When the AD8302 is used in stand-alone mode, without having any signal conditioning circuitry before it, it can perform simple Voltage Standing Wave Ration (VSWR) measurements. However, one would be limited by the frequency range (DC-2.7 GHz) as well as the lack of a full phase range (~0-180° instead of ~0-360°) which severely limit its ability to be used as an $S_{11}$ measurement device. This down-conversion stages is implemented that lowered the high-frequency (~4.7 GHz) to a more acceptable and easily processed frequency of about 40 MHz. Additionally, the two AD8302s were implemented in a topology where one of the input terminals for one of the AD8302s is phase-shifted by ~90°. As such modification enables the system to measure the full phase range and resolve the sign ambiguity issues.

Figure 12E:
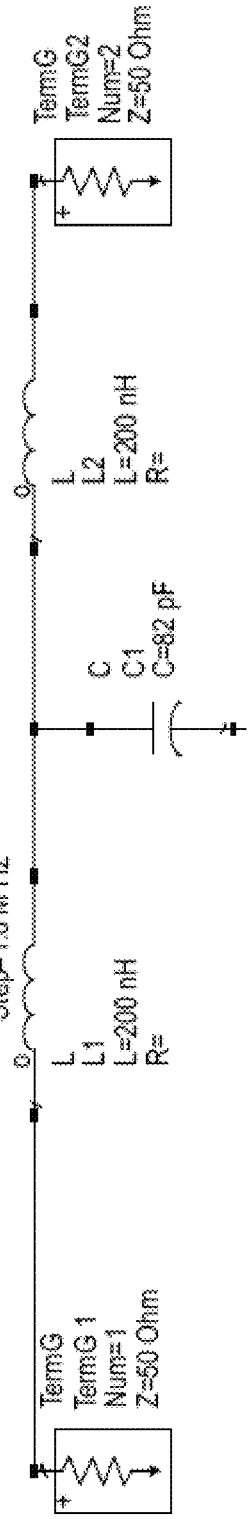
FIG. 12E is a schematic of the ADS schematic of the 90 degrees phase shifter.
Figure 12F:
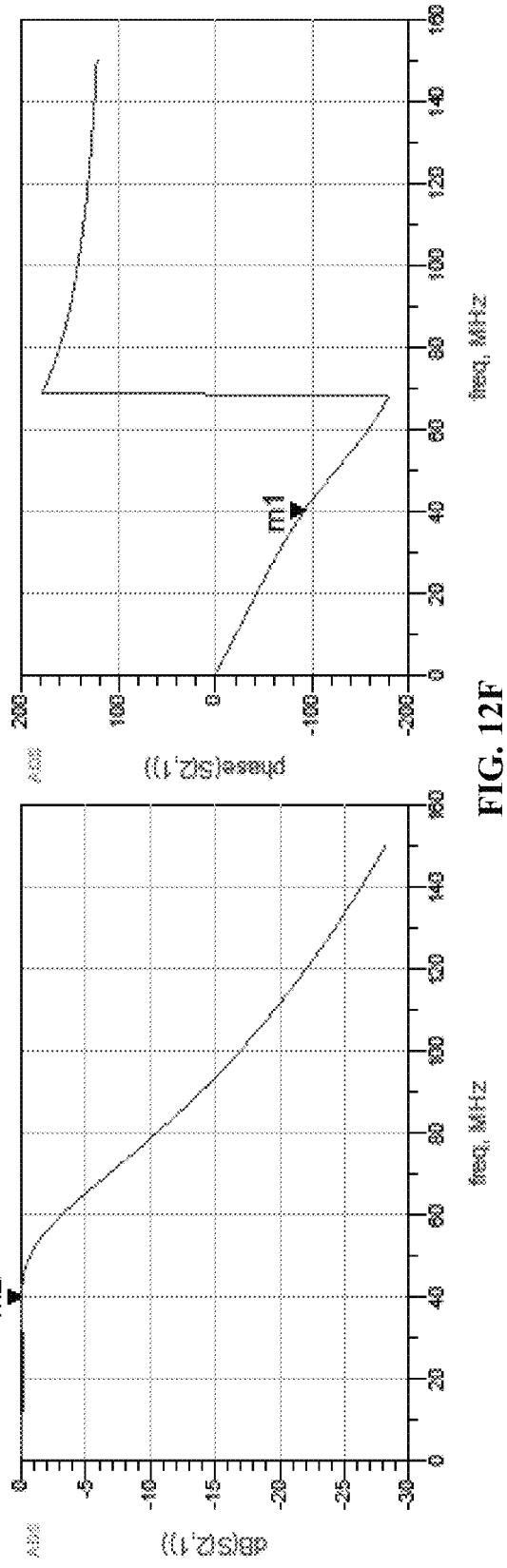
FIG. 12F is a graph of the Simulated performance of the phase shifter.

The said 90° phase shift is achieved by means of a T-type LPF filter at 40 MHz. This filter is designed in ADS, and its corresponding schematic can be seen in FIG. 12E. The resultant is a filter that creates a 90° phase shift at 40 MHz, while still attenuating undesired non-linear frequency inputs, as shown in FIG. 12F.

Microcontroller

In order to communicate with the different ICs, provide power, and perform signal read-out, an Arduino Nano 33 IoT microcontroller is used. This Arduino is characterized by its compactness, suitable performance, and its wireless connectivity. In addition, this particular model supports castellated mounting holes, which enable the solderability of the entire module onto the Wave Analyzer System PCB, hence achieving a higher overall compactness.

Figure 13:
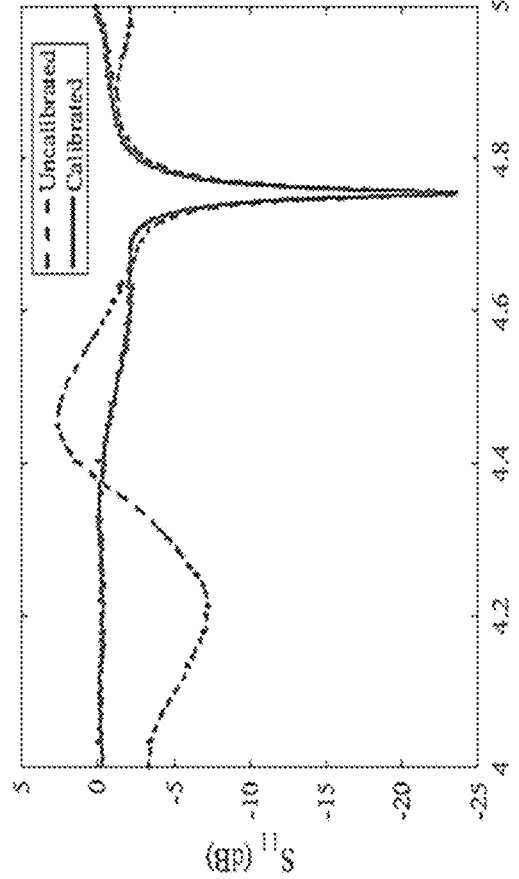
FIG. 13 is a graph of the calibrated wave analyzer's magnitude response.

In one embodiment, shown in FIG. 12A, the EM system 300 comprises frequency generation circuits to synthesize required high frequency signals, where the frequency generation circuits include at least one Voltage Controlled Oscillator 310 or at least one Phase-locked loop 320. A plurality of directional couplers 312, 314 are used as the main wave coupling structure. A first gain and phase detector 322 and a second gain and phase detector 324 are used to extract the reflection coefficient magnitude from an incident wave 330 and a reflected wave 332. A phase shifter 326 at one input of the detectors is utilized to enable full 0-360 degrees phase measurements. An attenuator 328 is used in the coupled incident wave path to balance its magnitude level with that of the coupled reflected wave. The wave analyzer 300 utilizes WiFi and USB-enabled Arduino microcontrollers 340. In one embodiment, a short-circuit load is used to perform magnitude calibration, which is shown in FIG. 13.

In one embodiment, the magnitude and phase of an EM sensor are measured, demonstrating the variation in the response due to a loaded state, such as with a skin sample at one location on the face, and an unloaded state, such as a free-space measurement, as shown in FIGS. 14A-14B, and FIGS. 15A-15B.

In one embodiment, as shown in FIGS. 16A-16E, the wave analyzer's printed circuit board 400 is composed of 4 layers, where each layer corresponds to a copper layer undertaking a specific role, such as a grounding layer 410, a signal routing and component assembly layer 420, and a power plane management layer 430. The printed circuit board 400 enables higher isolation between signal lines due to the multi-layer topology including the grounding vias and ground pours within. The multi-layer printed circuit board 400 achieves more compactness due to the ability to route signal and power lines (between the various components) conveniently on more than one layer. The printed circuit board 400 ensures tight impedance control due to a continuous ground plane beneath the RF signal layer.

The wave analyzer collects and generates data based on patient profiles, and sensor measurements, comprises customizable algorithms that interact with the cloud and the database, can predict the properties of the lesion for a specific category of lesion and patient and/or forward the data to web-based cloud systems for general data modelling enhancement procedures and model updates. The algorithms and predictive models aim to transform magnitude, phase, and frequency measurements of the reflection and transmission coefficients to specimen characteristics predictions. The algorithms and predictive models may utilize correlation-based classifiers that relates the S-parameter response across the frequency spectrum or may utilize best feature selection algorithms to identify representative S-parameter response at specific frequencies that can best predict the nature and condition of a suspected specimen. The algorithms and predictive models may utilize synthetic oversampling techniques, such as Synthetic Minority Oversampling Technique (SMOTE), ADASYN, or data augmentation, to balance imbalanced datasets. The adaptive synthetic sampling approach, or ADASYN algorithm, builds on the methodology of SMOTE, by shifting the importance of the classification boundary to those minority classes which are difficult.

SMOTE is an oversampling technique where the synthetic samples are generated for the minority class. This algorithm helps to overcome the overfitting problem posed by random oversampling. It focuses on the feature space to generate new instances with the help of interpolation between the positive instances that lie together. ADASYN uses a weighted distribution for different minority class examples according to their level of difficulty in learning, where more synthetic data is generated for minority class examples that are harder to learn. Data augmentation in data analysis are techniques used to increase the amount of data by adding slightly modified copies of already existing data or newly created synthetic data from existing data. It acts as a regularizer and helps reduce overfitting when training a machine learning model.

Figure 17:
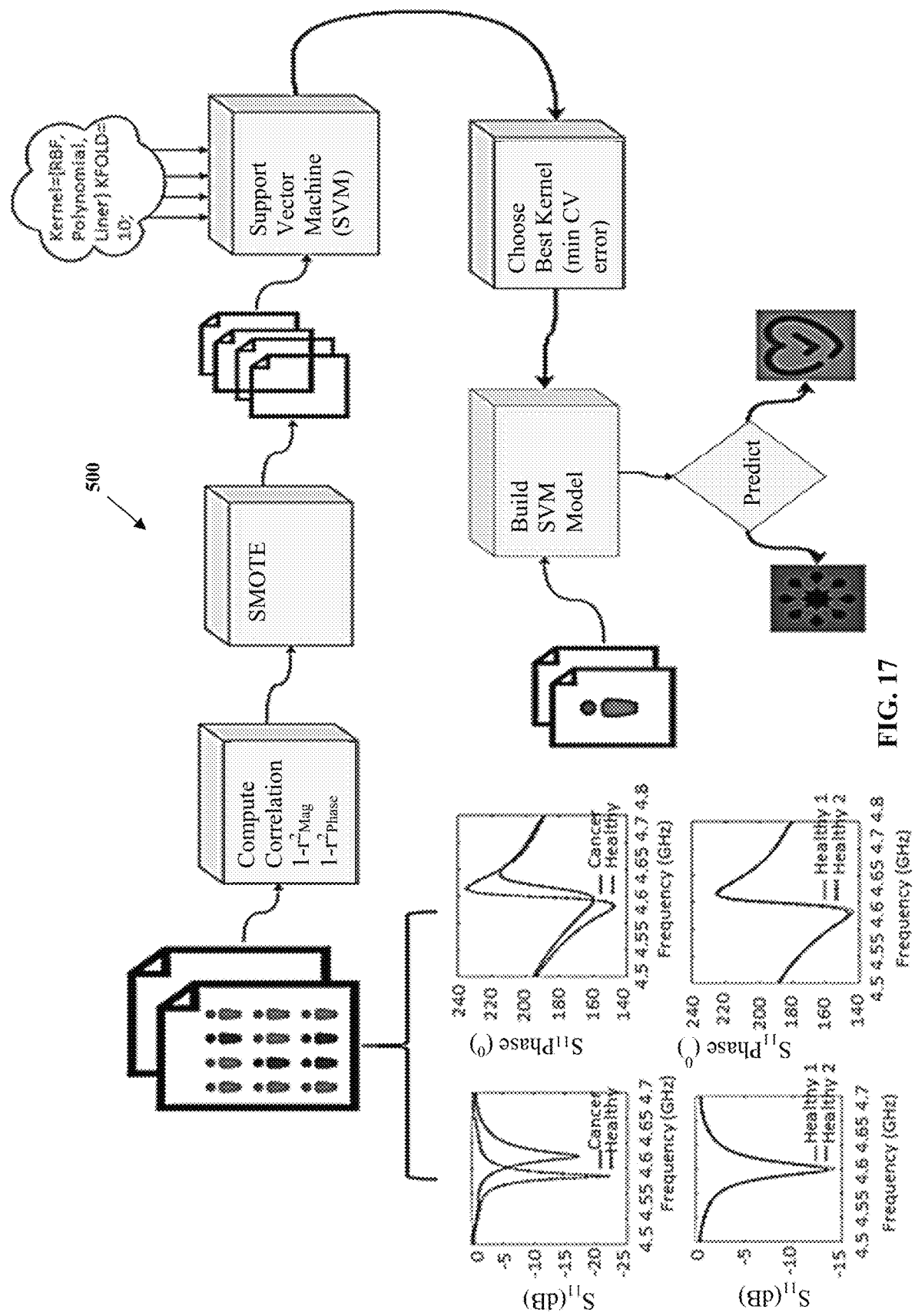
FIG. 17 is a schematic flow chart showing a correlation-based classification flow embodying one data modeling technique corresponding to the algorithms and models, according to one embodiment.

In one embodiment, as shown in FIG. 17, a correlation-based classifier 500 uses the correlation values between healthy and anomalous skin lesions within a patient in terms of magnitude and phase to build a classifier able to predict whether a skin lesion is cancerous, benign and/or healthy.

Figure 18:
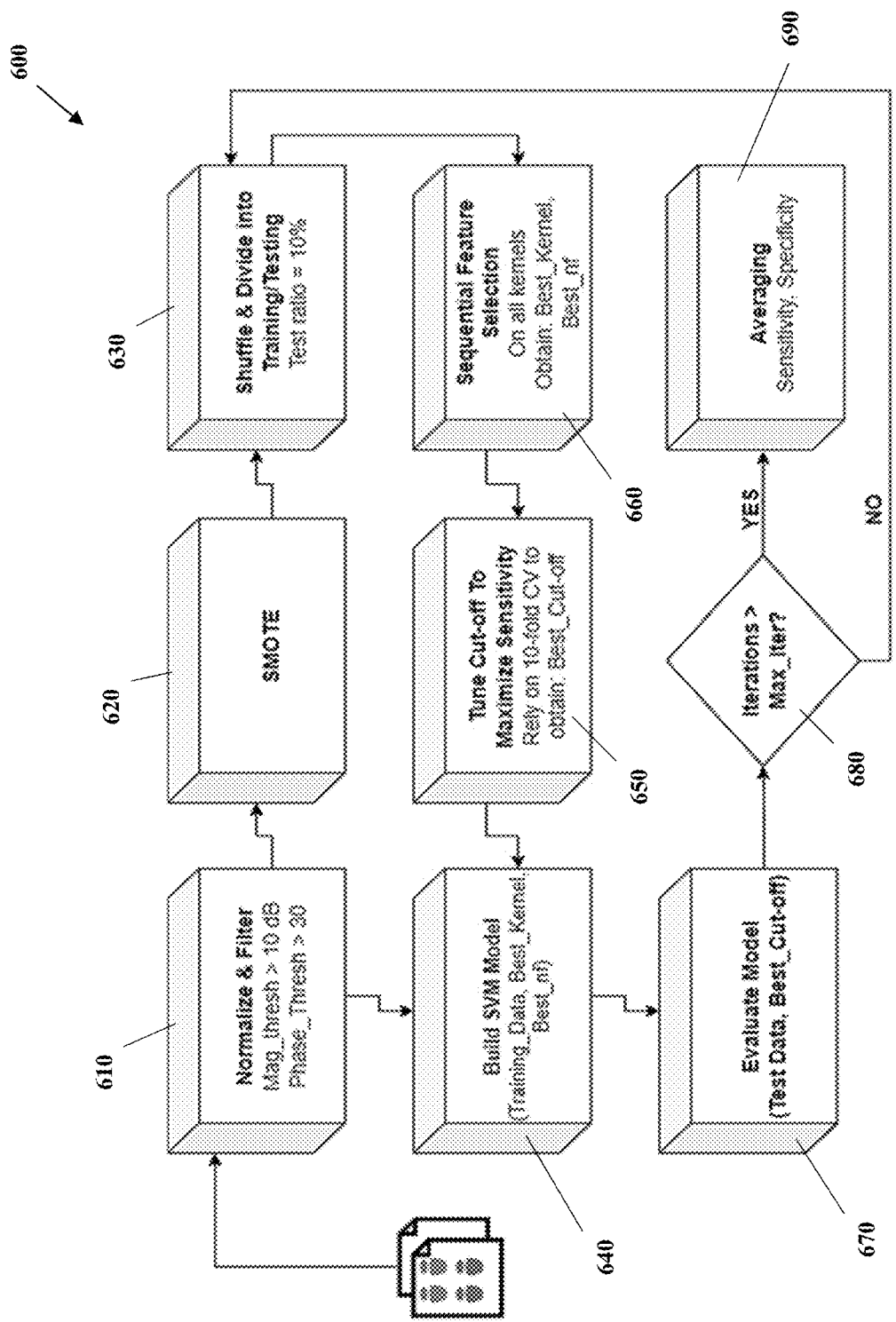
FIG. 18 is a schematic flow chart showing a feature selection-based classification flow embodying one data modeling technique corresponding to the algorithms and models, according to one embodiment.

In another embodiment, as shown in FIG. 18, a best feature selector 600 is used to extract the set of magnitudes and phases of the reflection coefficient at multiple frequencies can be best used predict whether a skin lesion is cancerous, benign and/or healthy. The best feature selector 600 includes a normalize and filter module 610, a SMOTE module 620, a Shuffle and Divide into Training/Testing module 630, a Build SVM model 640, a Tune Cut off to Maximize sensitivity module 650, a sequential feature selection module 660, an Evaluate Model 670, an Iterations decision 680, an Averaging module 690.

The normalize and filter module 610 sets a Magnitude Threshold less than about 10 dB and a Phase Threshold less than about 30 and proceeds to the SMOTE module 620 or the Build SVM model 640. The SMOTE module 620 proceeds to the Shuffle and Divide into Training/Testing Module 630. The Shuffle and Divide into Training/Testing Module 630 includes a test ratio equal to about 10%. The Shuffle and Divide into Training/Testing Module 630 proceeds to the sequential feature selection module 660. The sequential feature selection module 660 includes On all kernels and obtain the Best Kernal and the Best number of features. The sequential feature selection module 660 proceeds back to the Shuffle and Divide into Training/Testing Module 630 if the Best Kernal or the Best number of features are not obtained. If the normalize and filter module 610 obtains a Magnitude Threshold less than about 10 dB and a Phase Threshold less than about 30, then it proceeds to the Build SVM model 640. The Build SVM model 640 includes the training data, Best Kernel, and the Best number of features. The Build SVM model 640 proceeds to the Evaluate Model 670 where the test data and the Best Cut-off are determined. If the Iterations decision 680 obtains a Max Iterations, then it proceeds to the Averaging module 690. If the Iterations decision 680 does not obtain a Max Iterations, then it proceeds to the Shuffle and Divide into Training/Testing Module 630 to then proceed to the sequential feature selection module 660. The Averaging module 690 obtains the average sensitivity and specificity.

The correlation-based classifier and the best feature selector both make use of classification algorithms such as the support vector machine (SVM) among others detailed below.

EXAMPLES

The examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A Differential Measurement Approach

Clinical trials are performed on a population composed of patients with pre-diagnosed skin cancer, healthy individuals, patients with benign nevi, and a selection of patients with arbitrary diseases. Nevus or nevi is a benign (not cancer) growth on the skin that is formed by a cluster of melanocytes (cells that make a substance called melanin, which gives color to skin and eyes). A nevus is usually dark and may be raised from the skin, also called mole. These trials aim to evaluate the proposed device in a clinical setting. The focus of the work is on distinguishing between cancerous and non-cancerous skin lesions, and it is imperative to reiterate that the scope of this work does not include identifying diseases other than skin cancer. Notably, the diversified population aims to introduce variability to the sensor and technique to better evaluate their performance. These trials are approved by the Institutional Review Board (IRB) committee at the American University of Beirut [39]. Accordingly, 46 individuals are recruited to participate in the measurements, including 18 patients with pre-diagnosed skin cancer, 11 healthy volunteers, 10 volunteers with benign nevi, and 7 volunteers with arbitrary diseases. In what follows, the measurement procedure on each sub-group ultimately leading to the performance evaluation and statistical significance.

Measurements on Skin Cancer Patients

The patient population primarily consists of 17 BCC cases and 1 SCC case, corresponding to 50% male and 50% female participants whose ages fall between 32 and 87 years. All patients had lesions greater than 1.5 mm×1.5 mm and smaller than 10 mm×10 mm in size. These patients were set for Moh's surgery for the removal of their cancer and have signed the pertinent consent forms. The proposed measurement procedure consists of placing the sensor on the skin (in-vivo) and recording its resultant response afterwards in real-time. It is necessary to emphasize that during such measurements, the awareness of the effects of multiple internal and external factors on the measured properties is vital to the preservation of the quality of the measurements. These factors include body temperature, hydration, dryness, room temperature, and the introduction of any solutions to the skin. As presented within the literature, such factors are known to distort the measurements that reveal the specimen's true properties [19],[21], and [40]-[42]. Consequently, ensuring the fidelity of the measurements has been a priority throughout the study is by introducing and adopting several protocols within the measurement process to factor-in the internal and external variables. Of said protocols, dual in-vivo measurements for the differential approach are performed, since in-vivo measurements preserve the fidelity and quality of the lesion undergoing examination when compared to ex-vivo measurements. Particularly, it has been revealed that the dielectric properties of ex-vivo biological specimens may differ from the specimen within its natural medium, e.g., on-body skin. These differences are especially present if the environmental and physiological conditions of the measured specimen are not properly maintained [43]-[45]. Furthermore, the adopted dual measurement mode comprises measurements on the cancerous lesion and its adjacent healthy tissues. Hence, for each patient, a healthy baseline is established that the associated cancer measurement is compared to. This results in eliminating the effects of the internal and external factors common to both measured samples. These measurements are executed as follows: First, the sensor is positioned directly on top of the cancerous lesion, and 10 $S_{11}$ measurements are recorded. Next, the sensor is positioned on the healthy skin adjacent to the cancerous lesions, and 10 $S_{11}$ measurements are also recorded. During these measurements, a 1 mm-thick foam cylinder is loaded into the sensor's foam compartment to maintain a fixed stand-off distance from the specimen under test. Such stand-off distance and the underlying contact-less sensing are considered crucial elements in combatting the effects of different lesion topologies as well as undesired lesion fluids that may otherwise distort contact-based sensors. These measurements are then loaded into the data analysis algorithms to study the specimen's properties. The tested skin cancers included in the trial are located on the nose, cheeks, temples, forehead, and the scalp.

Measurements on Healthy Skin, Benign Nevi, and Arbitrary Diseases

Initially, the dual measurements on healthy individuals was executed to establish a baseline reference of healthy measurements for comparison with cancer measurements. Such a reference reveals the properties of healthy skin and enables the system to predict how the sensor's response during healthy skin measurements is expected to appear. Accordingly, the executed dual measurements are performed over multiple locations of the skin for 11 healthy individuals comprising 5 males and 6 females. Notably, the skin of the patients and healthy participants corresponds to type III skin on the Fitzpatrick scale [46].

In addition to establishing a profile of healthy reference measurements, the test specimens were increased to include dual measurements on patients with benign moles and arbitrary diseases. Accordingly, measurements on 10 patients were conducted with benign nevi, where the response of the sensor was recorded when loaded with the nevi, as well as on the adjacent healthy skin, and consequently compared both. The nevi are primarily located on the face and arms of the participants, and they were generally less than 5 mm in width. Similarly, the sensor was tested on 7 patients with arbitrary diseases, including Pemphigus Vulgaris, Accessory Tragus, Pyogenic Granuloma, Warts, and Leukemia Cutis. The response was differentially measured between the diseased lesions and their adjacent healthy counterparts. These experiments showed the difference between healthy skin and cancer within a patient, multiple healthy skin regions within a healthy individual, the difference between benign nevi and arbitrary diseases as well as their adjacent healthy skin, and finally, the variation between all of the difference sets. This data is then used to train and test the machine learning and classification models.

The Distinct Response to Healthy Skin and Cancerous Lesions

The objective herein is to capture the response of the sensor to cancerous and non-cancerous specimen, and to validate the existence of features that indicate their fundamental differences, which will ultimately develop learning models capable of diagnosis. For patients, measurements are performed on the cancerous lesions and their corresponding adjacent healthy skin, forming the differential pair. This differential pair consists of magnitude and phase values of the $S_{11}$ within a range of frequencies. Similarly, the $S_{11}$ measurements of healthy individuals are recorded from various locations around the face. FIG. 11A and FIG. 11B present the $S_{11}$ measurements on the cancerous lesion and its adjacent healthy skin from 3 patients in terms of magnitude and phase, respectively. In contrast, FIG. 11C and FIG. 11D present the dual measurements from two different locations (e.g., two sides of the temples, two sides of the nose, among others) on healthy volunteers. By comparing these measurements from the patient and healthy populations, the response of the sensor, and equivalently, the nature of the specimen under test, is manifested as (i) shifts in the resonance frequency of the sensor, and (ii) changes in the magnitude and phase of the sensor's measured $S_{11}$.

Hence, the key variables indicative of differences within measured specimen (frequency, magnitude of $S_{11}$, and phase of $S_{11}$) were identified, but the existence of distinctive response differences between cancer and healthy skin measurements based on those variables were displayed. Such unique differences, their levels, and their associated trends form the basis of the analysis in this method and system.

Skin Cancer Diagnosis

The skin cancer diagnosis in the current system and method generates an accurate model capable of predicting the malignancy of a suspected lesion based on the collected measurement data. The obtained $S_{11}$ measurements from the clinical trials are passed onto several data processing stages to prepare them for use within the classification model. The multi-feature nature of the input data is used ($S_{11}$ measurements obtained at different frequencies) to build the model.

In the classification approach, the Support Vector Machine (SVM) learning algorithm is used. Essentially, an SVM classification model is capable of predicting an outcome based on previously labeled training data, which in the context of the system and method, can be translated as predicting whether a measured specimen is cancerous or not based on training the model with previously collected data from healthy and diseased specimen. The SVM classifier performs the said prediction by attempting to generate a boundary, known as the hyperplane, that separates the clusters of data to be classified, e.g. cancerous vs non-cancerous measurements[21]. Notably, the SVM is often employed in medical binary classification applications, such as cancer detection due to its powerful classification ability[22-25]. Since the objective of the SVM is to construct an optimal separating hyperplane between the two classes, often SVMs rely on kernel functions to handle nonlinear problems by mapping the original input vectors to a higher dimensional space when the datasets cannot be linearly separated. The choice of the optimum kernel function is made upon computing a metric known as the k-fold cross validation loss (cv loss), where a lower value implies better model performance and equivalently better prediction capability. For a specified kernel function, the SVM model is thus trained and validated using a portion of the original data, dubbed as training data, which is typically 90% of the entire set. The training data is divided into k folds (k subsets). In an iterative manner, one of the k folds (~10 folds) is used for validation while the remaining 9 folds are used for training. This process is repeated k times (10 times in this case), and the validation error is recorded at every iteration. The average loss across these iterations is then used to determine the best kernel to build the model. Finally, the resulting model is evaluated on the remaining 10% of the dataset, which is reserved as testing data to evaluate the classifier performance. An iterative technique known as the Wrapper Method is employed along with cross-validation in order to determine the best kernel and optimal number of features for the SVM classifier model. The Wrapper Method will be discussed in the following sections.

Figure 19:
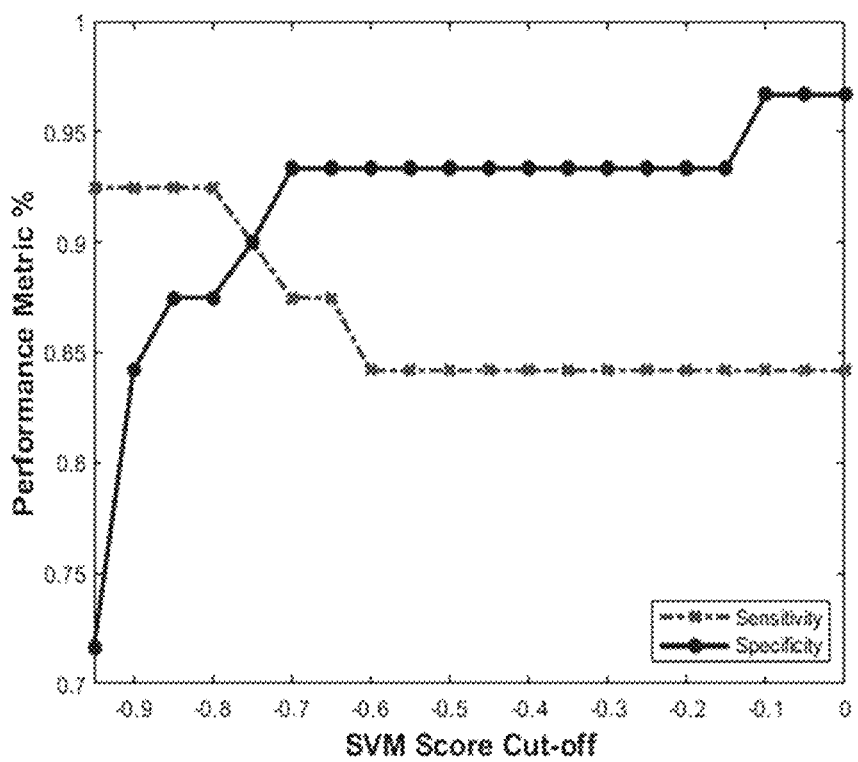
FIG. 19 shows the performance metrics variation as a function of SVM score cut-offs.

The wrapper method is a technique described in the Methods section, to identify the best kernels and select the best feature set, i.e., a combination of $S_{11}$ magnitudes and phases at specific frequencies which are deemed capable of accurately classifying the measured lesion based on their cross-validation (CV) score. These "best features" and "best kernel type" are used to build a classifier capable of identifying whether a measured specimen is cancerous or healthy. Particularly, once the best feature set is chosen based on the lowest Cross-Validation (CV) error, the SVM model is built and evaluated using the training and testing data. This evaluation comprises the computation of the most common classification performance metrics, the model sensitivity and specificity. The system and model development is thoroughly detailed below The statistical significance of the method is studied by developing and evaluating three test scenarios. These scenarios comprise evaluating three data groups that combine different samples from the general population in a primary effort to investigate the system and method's ability to distinguish between the cancer group and non-cancer groups. The test scenarios are as follows: Scenario 1—'skin cancer' vs. 'healthy skin+benign nevi' (abbrev. 'SC' vs. 'H+BN'); Scenario 2—'skin cancer' vs. 'benign nevi+arbitrary diseases' (abbrev. 'SC' vs. 'BN+AD'); Scenario 3—'skin cancer' vs. 'healthy skin+benign nevi+arbitrary diseases' (abbrev. 'SC' vs. 'H+BN+AD'). In this approach, the sensitivity metric is favored rather than the specificity. This is because sensitivity indicates the probability that a diagnosed cancer lesion is truly cancerous, and the specificity indicates the probability that a non-cancerous lesion is truly non-cancerous. Hence, a low sensitivity would have dangerous consequences on the patient due to the misdiagnosis of a cancerous lesion as a benign one. For this reason, the method maximizes the sensitivity, without sacrificing the specificity, as it would in fact be safer for the patient to misdiagnose a healthy lesion as cancerous rather than a cancerous lesion as healthy. As such, CV is used to tune the SVM score cut-off limits, as discussed in the Methods section, for which samples are considered benign or cancerous. In FIG. 19, the inverse relationship between sensitivity and specificity versus the SVM score cut-off for one CV training data iteration is displayed. Table. 1 summarizes the corresponding performance metrics on the test data of the built classifiers for the three scenarios.

TABLE 1

| Sensitivity Enhancement. | | | | | |
|---|---|---|---|---|---|
| 'SC' vs. 'H + BN' | | 'SC' vs. 'BN + AD' | | 'SC' vs. 'H + BN + AD' | |
| Sensitivity | Specificity | Sensitivity | Specificity | Sensitivity | Specificity |
| ~91.69% | ~84.62% | ~90.34% | ~77.69% | ~92.14% | ~82.31% |

This table shows the corresponding sensitivity and specificity for each test scenario. SC represents Skin Cancer; H represents Healthy Skin; BN represents Benign Nevi; AD represents Arbitrary Diseases. The analysis shows that the cancerous from non-cancerous groups is distinguished with a sensitivity up to about 92% and specificity up to about 84.6%. The obtained results effectively validate the ability of the proposed system to distinguish between cancerous and non-cancerous lesions.

Discussion

The presented system establishes a unique and innovative platform that successfully integrates EM-based sensing for dermatology diagnostics. The combination of several sensor design decisions tailored for malignant lesion detection enhanced the sensitivity within the microwave frequency range. The findings herein, through robust statistical modeling, attest to the system's ability to electromagnetically interrogate suspected skin lesions non-invasively. In fact, the system and method is also particularly useful where on-field medical services are required, like refugee camps, as well as during events that disrupt medical services, such as the case of pandemics. For example, the recent, and still on-going COVID-19 pandemic, has resulted in a substantial decrease in cancer diagnosis, screenings, and referral procedures, which is equivalent to delays in the timely identification of the disease. This decrease is a result of multiple factors such as the quarantine orders, the disruption of medical care services, and the patients rescheduling their clinical visits during the critical months of the pandemic due to fear of COVID-19 exposure within medical facilities 43-47. These observations profoundly highlight the need for a quick point-of-care device capable of diagnosing skin cancer. This need is further amplified by the fact that delays in skin cancer screening cause the disease to evolve, potentially spreading into other tissues and resulting in dangerous health complications. Accordingly, the proposed portable solution herein is characterized by several features that underline its optimality for adoption in skin cancer diagnosis within clinical settings, households, and on-field sites.

Additionally, aside from enabling the detection of miniature skin cancers, the sensing tip is particularly useful for surgeons removing cancerous skin lesions. In the traditional wide-margin excision method, "normal skin" surgical margins need to be drawn around the skin cancer and removed. They vary in size from 3 mm to 20 mm beyond the visible tumor size. This is done to make sure all the cancer is removed as cancer cells often extend beyond what the physician clinically sees. Due to its fine sensing tip, the proposed "pen-like" device can accurately determine small and large tumors' malignancy, effectively identifying the boundaries of the cancer both qualitatively and quantitatively, as proven by these clinical trials.

This would also confer a massive advantage to patients undergoing Moh's Micrographic Surgery, where successive excisions from the suspected lesions are often required to ensure the complete removal of the cancer. In fact, the sensor can detect the actual limit of the tumor much more accurately when compared to the conventional methods of skin cancer assessment discussed in 4-7. Hence, the number of stages (or re-excisions) needed can be minimized, therefore allowing the surgeon to draw the cancer limit more precisely from the beginning. Such an advantage reduces the duration of the procedure as well as the risk for potential disfigurement in sensitive regions and the risk of tumor recurrence. In addition, the frequency of operation, being within the microwave range, results in a significantly reduced design cost of the RF components required for the wave analyzer system when compared to the design cost of components that operate at mm-wave frequencies and beyond. Moreover, the proposed device, which is portable, non-constraining, and highly sensitive, presents superior features in comparison with existing commercial solutions.

It is necessary to note that the enhanced sensitivity of the sensor, and specifically the multi-feature statistical analysis methods adopted by the approach reveal deep insights into the nature of the skin lesion under test and highlight the importance of analyzing the data at multiple frequencies. The results shows that the skin cancer prediction models exhibit high performance, paving the way for the development of a commercial solution that can be integrated into clinical settings.

Support Vector Machines (SVM)

In applications that require regression analysis or classification between different classes, the SVM has proved itself to be one of the most powerful and frequently utilized machine learning models under the category of supervised learning. Essentially, an SVM classification model is capable of predicting an outcome based on previously given labeled training data, which in the context of this embodiment can be translated as predicting whether a measured specimen is cancerous or not based on training the model with previously collected data from healthy and diseased specimen. The SVM classifier performs the said prediction by attempting to generate a boundary, known as the hyperplane, which separates the clusters of data to be classified, e.g. cancerous vs non-cancerous measurements. Notably, the SVM is often employed in medical binary classification applications, such as cancer detection due to its powerful classification ability.

Figure 23:
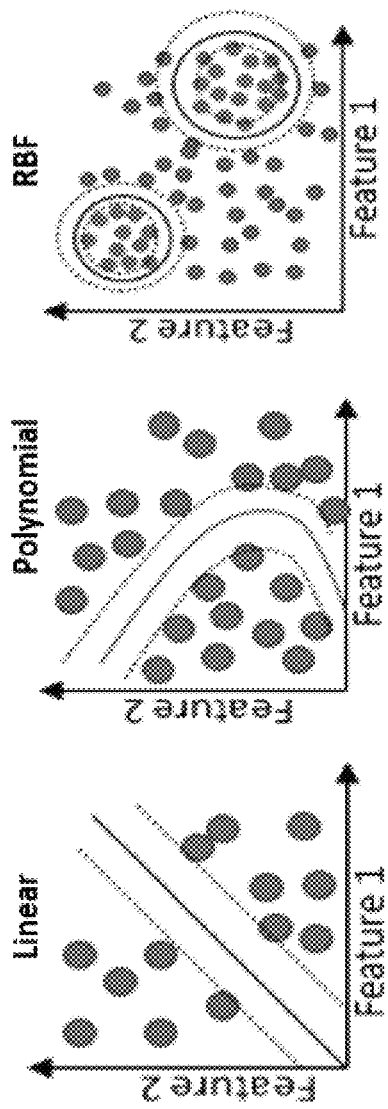
FIG. 23 are graphs of the Typical SVM hyperplanes.

The SVM uses functions known as kernels in order to guide the hyperplane creation process in terms of its geometry, since datasets cannot always be separated linearly. To illustrate, FIG. 23 shows some of the most common kernel functions, such as the polynomial, radial basis, and linear functions that are each employed where they are capable of accurately separating the different classes. The choice of the optimum kernel function is made upon computing a metric known as the K-fold cross validation loss, where the lower value implies better model performance and equivalently better prediction capability. Upon choosing the best kernel function, the SVM model is trained using a portion of the original data, dubbed as training data, which is typically 90% of the entire set. Then, after building the model, the remaining 10% of the dataset is used as testing data to validate the performance of the obtained classifier. Throughout this embodiment, the SVM as the classification model, although other classification models may be used.

The performance of the resultant classifier is assessed based on the typical metrics that are derived from the confusion matrix parameters, such as the True Positive (TP), True Negative (TN), False Positive (FP), and the False Negative (FN). The utilized metrics are the Sensitivity and the Specificity. In the context of this embodiment, the Sensitivity is defined as the classifier's ability to correctly identify whether a specimen is cancerous, and the Specificity is the ability to identify a healthy specimen. The formulae of these metrics are given as follows:

$$\text{Sensitivity} = \frac{TP}{(TP + FN)} * 100 \quad (8)$$

$$\text{Specificity} = \frac{TN}{(TN + FP)} * 100 \quad (9)$$

Imbalanced to Balanced Data: Synthetic Minority Oversampling Technique (SMOTE)

In medical diagnostics applications, the primary data classes of interest are the disease group and the healthy unaffected control group. However, the amount of collected data points highly depends on the availability of the patients with a particular disease as well as the number of healthy volunteers. Common to medical applications, the data available for the disease class is often less than its control class counterpart, a scenario that leads to data imbalance, and the dominance of the control class over the data, which ultimately affects the results of the forthcoming analysis and leads to misclassification. The underlying cause of such misclassification is that the data models being developed will become more trained on the prevalent control class as opposed to the disease class. In such cases of class imbalance, the overall performance of the predictive model will suffer from low diagnostic accuracy, particularly because the verdict being sought, being the existence of cancer for instance, is extracted from the minority class. Notably, it has been shown that the performance of such models can be greatly enhanced by employing class balancing techniques, such as the Synthetic Minority Oversampling Technique (SMOTE). SMOTE is an algorithm that aims to balance the different classes by intelligently synthesizing new data points based on information from the pre-existing data points of the minority class. Such oversampling enables higher accuracy and a more realistic scenario when compared to merely oversampling the pre-existing data. Essentially, the SMOTE algorithm, computes the distance between several predetermined points (neighbors) to synthesize a new one by means of interpolation. In this embodiment, SMOTE is used to increase the minority class observations, i.e.: skin cancer observations, to a number equivalent to that of the control class.

The Wrapper Method

Since the dataset is composed of a plethora of features pertaining to magnitude and phase measurements at different frequencies, finding the optimal subset of features will greatly enhance the prediction capability of the classifier system. For this reason, the wrapper method is used to iteratively execute sequential feature selection to identify the critical features that, based on certain performance metrics, can best predict the outcome. In the system, forward feature selection is used to identify up to a maximum of 20 critical features for a given kernel function of the SVM classification algorithm. Hence, the wrapper algorithm sequentially identifies the next best feature for a given kernel function, such as the Linear, RBF, and the Polynomial kernels. Concurrently, the CV-loss is computed for each model with a newly added critical feature relevant to the specific kernel function. The method identifies the best kernel along with its critical feature set that results in the lowest cv loss. In the case of identical cv loss for multiple kernels, the kernel with the lowest number features achieving said error is chosen, because it is less computationally expensive and delivers the same performance. These algorithms have been developed and tested in Matlab. To compensate for the small size of datasets, this process is repeated 10 times by randomly shuffling and dividing the data into training and testing sets. Thus, for each round, the data is randomly shuffled and divided into ~90% training data and ~10% testing data, and the resultant SVM model performance is evaluated using the metrics introduced in the following section.

The system generates an accurate model capable of predicting the malignancy of a suspected lesion based on the collected measurement data. The classification leverages the multi-feature nature of the input data ($S_{11}$ measurements). In the system, the best feature set capable of accurately classifying the measured lesion is identified and selected. Both models are evaluated according to common classification performance metrics, such as sensitivity, and specificity.

For the first correlation-based method, the designed classifier achieves ~97.85% sensitivity and ~95.4% specificity. As for the second method, the classifier also exhibits high performance, exhibiting a sensitivity that exceeds ~90% and a specificity up to ~84.6%. The obtained results demonstrate the strength of utilizing an EM-based non-invasive lesion-optimized sensor in diagnosing skin cancer based off on the collected clinical trial measurements.

Discussion

The presented system establishes a unique and innovative platform that successfully integrates EM-based sensing for dermatology diagnostics. The combination of several sensor design decisions tailored for malignant lesion detection enhanced the sensitivity in the microwave frequency range. The findings, through robust statistical modeling, attest to the system's ability to electromagnetically interrogate suspected skin lesions non-invasively. The enhanced sensitivity of the sensor, and specifically the multi-feature statistical analysis methods adopted by this method and system unlock deep insights into the nature of the skin lesion under test and highlight the importance of analyzing the data at multiple frequencies. The results show that the skin cancer prediction models exhibit high levels of sensitivity, accuracy, and specificity, paving the way for the development of a commercial solution that can be potentially integrated into clinical settings.

Methods

EM Sensor Simulation and Fabrication.

The developed sensor is designed on a RT Duroid 5880 substrate [47] having a thickness of 0.79 mm and a dielectric constant of 2.2, and a loss tangent of 0.0009. Prior to its fabrication, it is designed, validated, and optimized using the Ansys Electronics Desktop electromagnetics simulator [48]. The sensor is composed of two sections, a resonant element and an impedance matching network. The resonant element is a narrow 1 mm microstrip line with a corresponding characteristic impedance of 85 ohms. Its length spans 19.825 millimeters in length, which corresponds to the optimized half wavelength at 4.75 GHz. The sensor is designed with an optimized matching network that takes into consideration the effect of the shielding enclosure. Consequently, an impedance matching network matches the sensor's impedance to the standard feeding impedance of 50 ohms. The matching network comprises a 4.5 mm-long microstrip line with a 40-ohm characteristic impedance, along with a 1.2 mm-long open shunt stub section having a characteristic impedance of 35 ohms. Furthermore, the 40-ohm microstrip line is tapered to further optimize the impedance matching, as shown in FIG. 1A. The aforementioned procedure results in a well-impedance-matched sensor that is fabricated and assembled as shown in FIG. 1C and FIG. 1D. The sensor is then tested using a Vector Network Analyzer from Keysight [49]. The simulated and measured $S_{11}$ are plotted in FIG. 10, where excellent agreement is observed between both. The overall dimensions of the assembled sensor within its enclosure are 31 mm×11.8 mm×6 mm.

Wave Analyzer System Fabrication

Figure 20A:
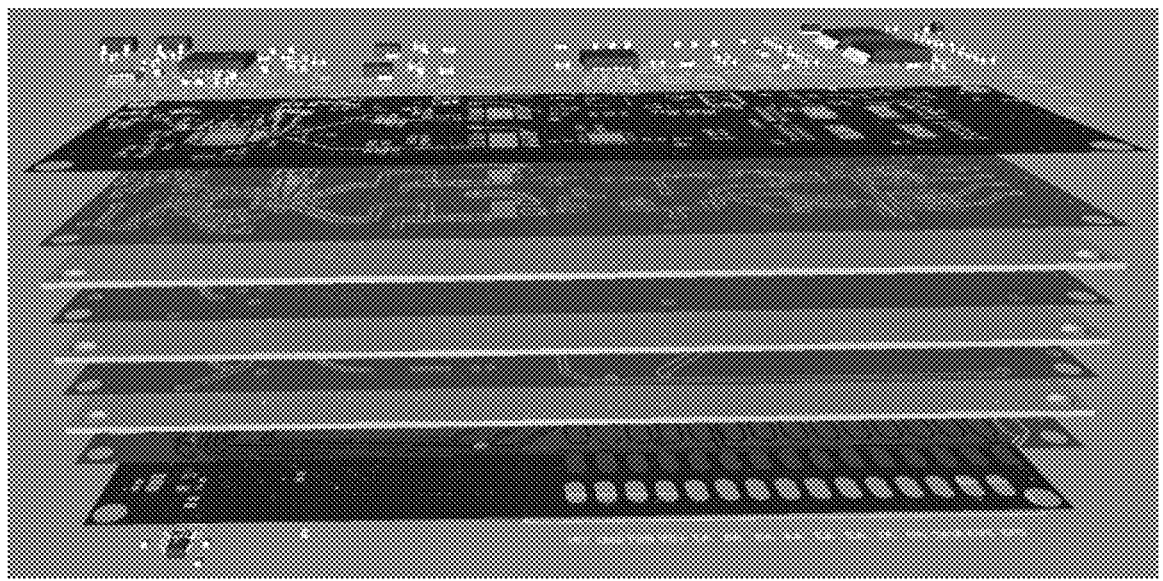
FIG. 20A is an exploded view of all PCB layers of the wave analyzer system, where the blue layers are solder mask, gold layers are copper, and white layers are the dielectric material.
Figure 20B:
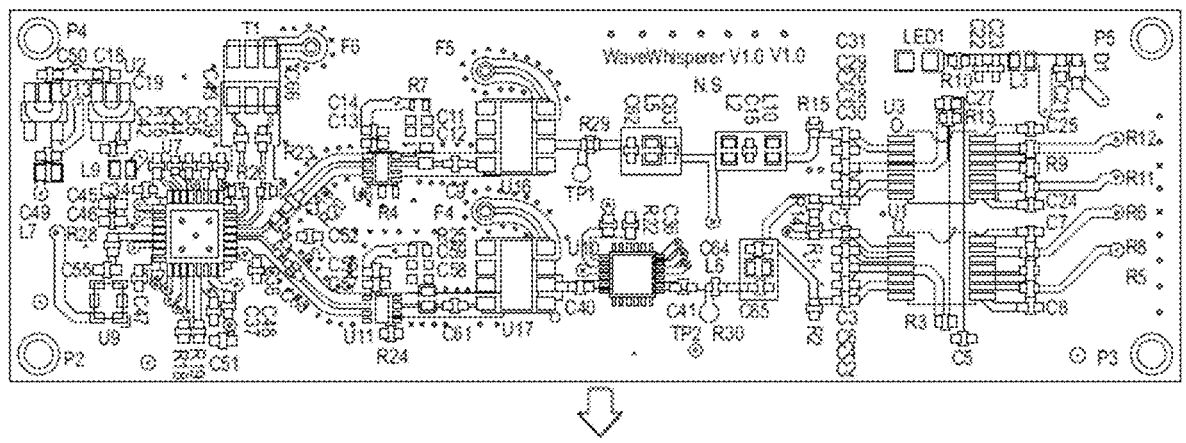
FIG. 20B is the wave analyzer system after fabrication of the PCB.
Figure 20B:
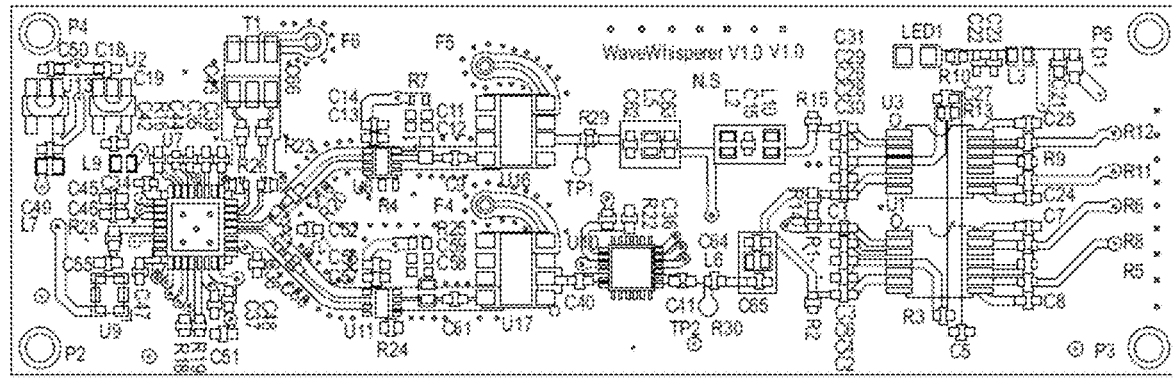

Typically, high-performance RF boards utilize multi-layer PCBs such as 4 or more layers. This allows for better isolation between the different planes and ensures the presence of a continuous ground plane beneath transmission lines. It also allows to accommodate for the very narrow 50-ohm routing lines needed for impedance matching of RF integrated circuits (ICs). The PCB of the analyzer circuit adopts a 4-layer stack-up. Each layer serves a designated role as follows: Layer 1 corresponds to a routing and component assembly layer; Layer 2 corresponds to a continuous ground plane; Layer 3 corresponds to a power plane containing 3.3V and 5V voltages which are required to power on the different components; Layer 4 is another routing and component assembly layer. These layers can be seen in the exploded view in FIG. 20A, and the fabricated model is shown in FIG. 20B. Details regarding the function and fabrication of these layers can be found below.

The Wave Analyzer System PCB

The 4 Layer PCB

Layer 1—RF Transmission Lines and High-Speed Signals: Layer 1 represents the top-most layer where component placement and the corresponding signal routing take place. These signal lines represent the RF transmission lines with controlled characteristic impedance as well as the high-speed intermediate frequency (IF) signals. Layer 1 is shown in FIG. 16B.

Layer 2—Continuous Ground Plane: As a common practice, a continuous ground plane is typically placed beneath the signal layer to reduce noise, signal crosstalk, and interference. Hence, layer 2, being just below layer 1, is designated as a continuous ground plane. Additionally, this continuous ground plane is necessary to maintain the 50-ohm controlled impedance of the RF transmission lines on layer 1. Layer 2 is shown in FIG. 16D.

Layer 3—Power plane: The active components within this architecture, such as the detectors, amplifiers, synthesizers, and the attenuator, all require biasing by means of a power supply. As a result, layer 3 of the stack-up is designated as a power plane that includes several sub-planes with specific voltages, such as 3.3V and 5V, that the relevant components can connect to by means of a via to this layer. Layer 3 is shown in FIG. 16C.

Layer 4—Signal and Ground: Similar to the top layer, the bottom layer also includes signal lines, components, and a ground plane. This layer enables the system to miniaturize the entire PCB, since it acts as a bridge that allows routing signal lines from the top layer, down to the bottom layer, and then to the top layer again to avoid signal line cluttering and unnecessarily lengthy signal lines. The latter also allows for added compactness by enabling RF components to be closely placed without worrying about a densely packed top layer. Layer 4 is shown in FIG. 16E.

Commercial PCB Stack-Up and RF Transmission Lines

This PCB is fabricated at the JLC PCB fabrication house. The chosen stack-up is a 4-layer one known as the JLC7628. The essential parameters are the dielectric constant of the substrate material as well as its thickness, since this will dictate the width required for a 50-ohm impedance-controlled RF transmission line. The dielectric constant of the substrate layer is about 4.6 and its thickness is about 0.2 mm. Such properties result in a about 50-ohm line width of about 0.31 mm, which greatly facilitates the interconnection between multiple RF ICs while minimizing coupling and noise.

Frequency Synthesizer Testing

Initially, the synthesizer functionality of the Wave Analyzer System is tested to validate proper communication and operation. As a result, the Wave Analyzer System is connected through a USB connection from a PC and utilize the Arduino IDE software to program accordingly. Then, the frequency diagnostics port (port A) of the Wave Analyzer System is connected to a spectrum analyzer in order to observe the output. Accordingly, the Wave Analyzer System is programmed to synthesize the frequencies 1 GHz, 2 GHz, 3 GHz, and 6 GHz. The photos in FIGS. 22A-22D verify the successful frequency synthesis operations and validate the desired overall functionality.

Results: Raw Measurement Data, Noise, and Filtering

Next, the correct operation of the various blocks within the Wave Analyzer System is verified by performing $S_{11}$ measurements when connected to the EM sensor. As such, the transmitter and receiver modules of the Wave Analyzer System are connected as shown in FIG. 12A, and they are powered by means of a USB connection to a PC. Afterwards, the transmitter module's frequency output port is connected to the input of the directional coupler, which is then connected to the EM sensor. Then, the coupling ports of the directional coupler are connected to the two signal inputs within the receiver module of the Wave Analyzer System. The Wave Analyzer System is then programmed to sweep the 4 GHz-5 GHz frequency range which encompasses the sensor's frequency of operation (4.75 GHz).

Initially and before calibration, the $S_{11}$ magnitude of the EM sensor is measured and plotted in FIG. 13. At frequencies that are non-operational, an $S_{11}$ of 0 dB should be obtained. However, a deviation in the non-resonant regions of the sensor is observed. Such deviation is expected due to the inherent losses and imbalances within the non-ideal components corresponding to the incident and reflected signal paths within the Wave Analyzer System. To remedy this imbalance, a calibration procedure is executed. Calibration generally refers to accounting for the deviations in measurements by teaching the system how an ideal response should look like. Hence, the short-circuit calibration technique is applied in which the Wave Analyzer System is loaded with a short-circuit load as its DUT, which causes the waves to completely reflect, and should therefore reach a 0 dB level across all frequencies. The deviations from this 0 dB level are then used to teach the Wave Analyzer System where to add or subtract magnitude levels in order to achieve a balanced output. As shown in FIG. 13, the calibrated output closely resembles that of a high-end VNA measurement.

Figure 14B:
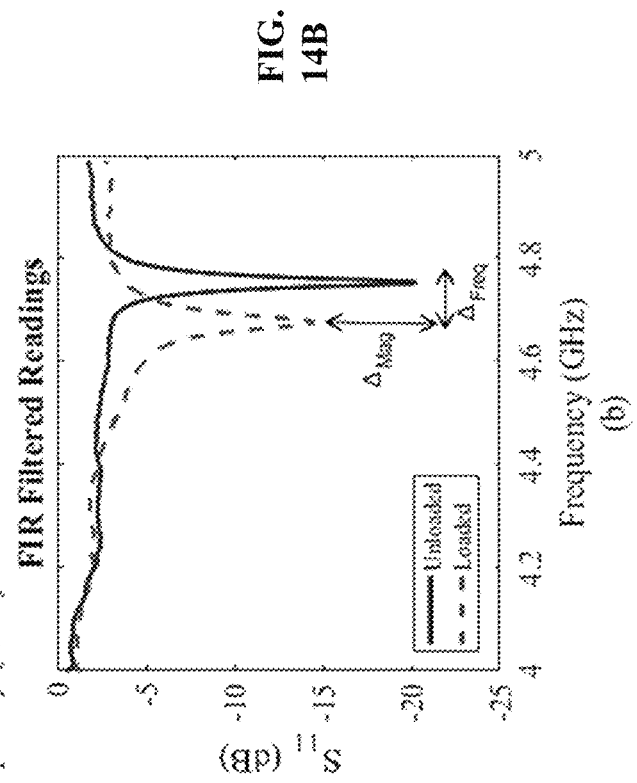
FIG. 14B is graph of the same response while being filtered using a FIR filter.
Figure 14A:
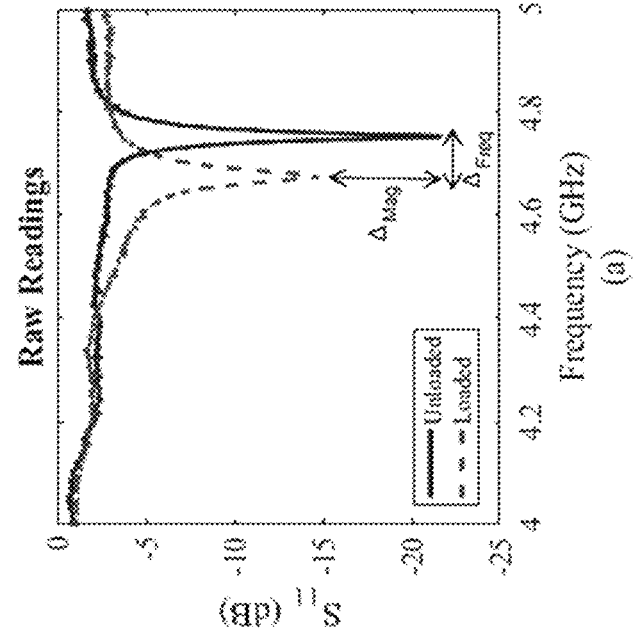
FIG. 14A is a graph showing the wave analyzer's magnitude response to an EM sensor in a loaded and unloaded states.
Figures 15A, 15B:
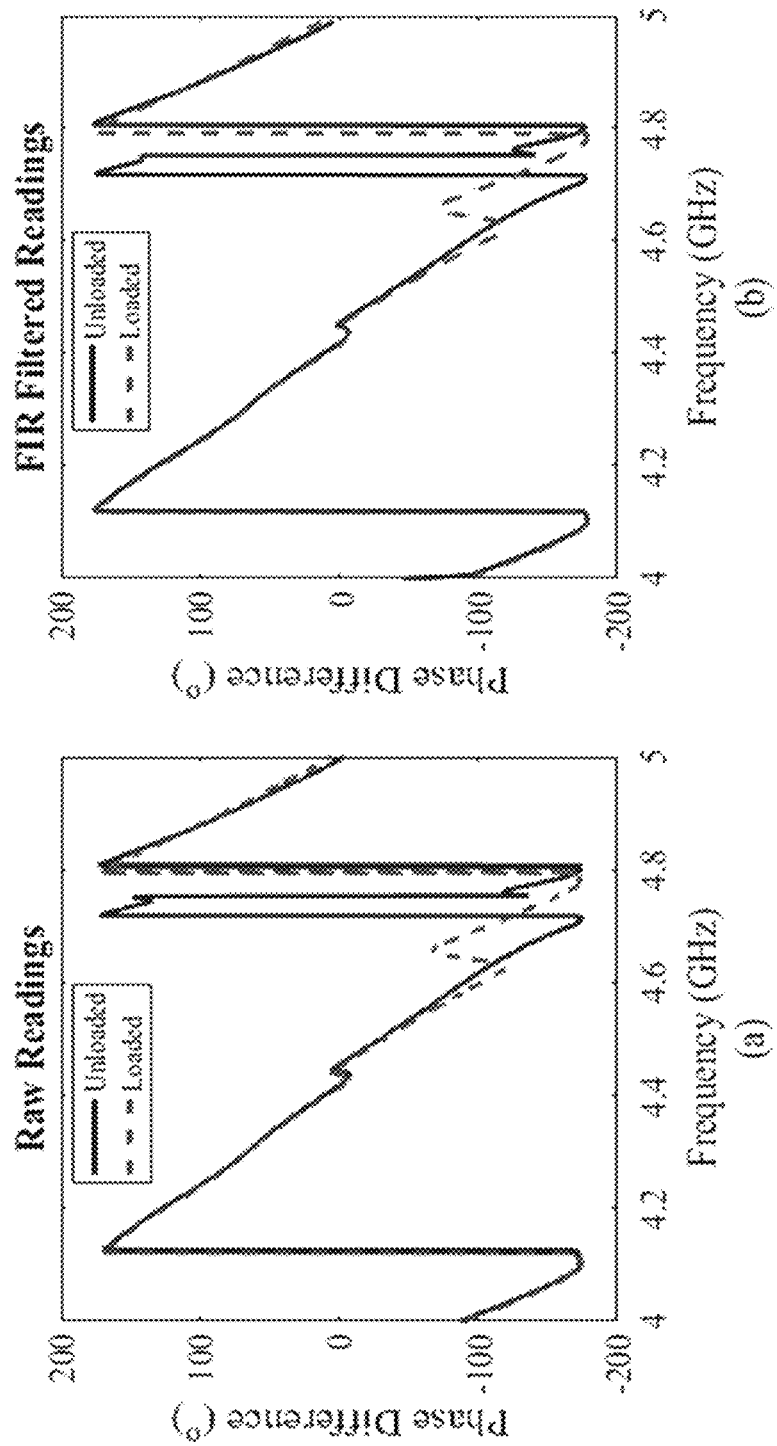
FIG. 15A is a graph of the wave analyzer's 0-360 degrees phase response to an EM sensor in a loaded and unloaded states.
FIG. 15B is a graph of the same response while being filtered using a FIR filter.

Furthermore, the Wave Analyzer System is then used to perform a clinical test measurement using the proposed EM sensor. Initially, the sensor's $S_{11}$ is measured in free-space (without being loaded with skin) and the response is recorded from both detectors within the Wave Analyzer System, as shown in FIG. 14A-14B. Then, another measurement is performed whilst loading the EM sensor with a volunteer's skin. The frequency of operation as well as the magnitude of the reflected waves have been altered, as expected. The initial response was slightly noisy, which is due to the high-frequency noise leaking into the system as well as inaccuracies of the microcontroller's ADC. To lessen the noise, a digital filter known as the Finite Impulse Response (FIR) filter is designed in code and applied. The filter produced great results when the passband frequency and stopband frequency parameters were set to about 150 Hz and about 1000 Hz, respectively. The resultant waveform is shown in FIG. 14B, where it is smoother and less noisy. In addition, the phase measurement capability of the Wave Analyzer System is tested. Similar to the case of the magnitude measurement, the EM sensor is first measured at an unloaded state, followed by a loaded one. FIG. 15A presents the full 0-360° phase output in both states, where a clear and expected phase shift is observed. Additionally, the developed FIR filter is also applied to the noisy phase reading, resulting in a cleaner waveform as shown in FIG. 15B.

Finally, due to the successful magnitude and phase measurements, the Wave Analyzer System is a reliable alternative to the traditional VNA.

Data Collection

The proposed EM sensor is used to examine skin lesions on patients and healthy volunteers. These measurements are performed by placing the sensor on the skin lesion and ensuring light contact with the lesion. These measurements comprise the collection of $S_{11}$ (magnitude and phase) data that are key to understanding the nature of the specimen under test, especially that the different composition of a specimen (skin sample) dictates its complex permittivity, which in turn determines the unique variation in the sensor's $S_{11}$. The measurements are conducted using the proposed EM sensor along with a VNA [49]. For each specimen, whether healthy or cancerous, 1001 points corresponding to the frequencies from 4 GHz to 5 GHz, are swept and recorded 10 times. This frequency range encompasses the sensor's frequency of operation. Additionally, the redundant measurements, which are averaged later on, contribute in reducing random errors, ensuring repeatability, and improving the overall fidelity of the measurements. Once the data from the designated locations is obtained, it is then categorized and labeled based on its nature, dimensions, and location, resulting in a set of $S_{11}$ magnitude and phase measurements for each measurement class (healthy, cancerous). Eventually, by applying the proper statistical classification algorithms to this data, as introduced in the following sections, the specimen under test can be distinguished as healthy or cancerous.

Figure 21A:
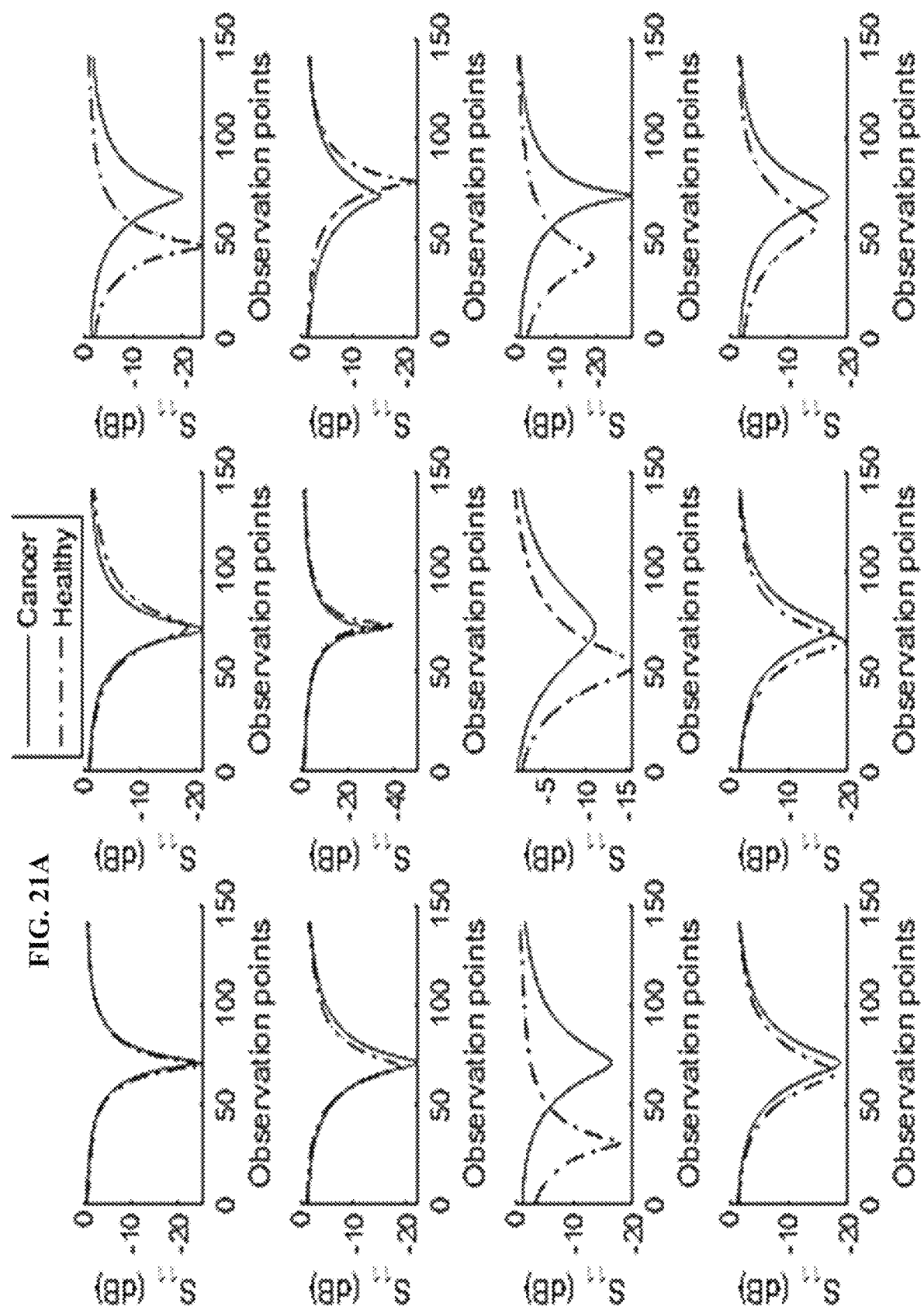
FIGS. 21A-21B are graphs of the recorded data for the $S_{11}$ magnitude and phase response within patients, respectively.
Figure 21B:
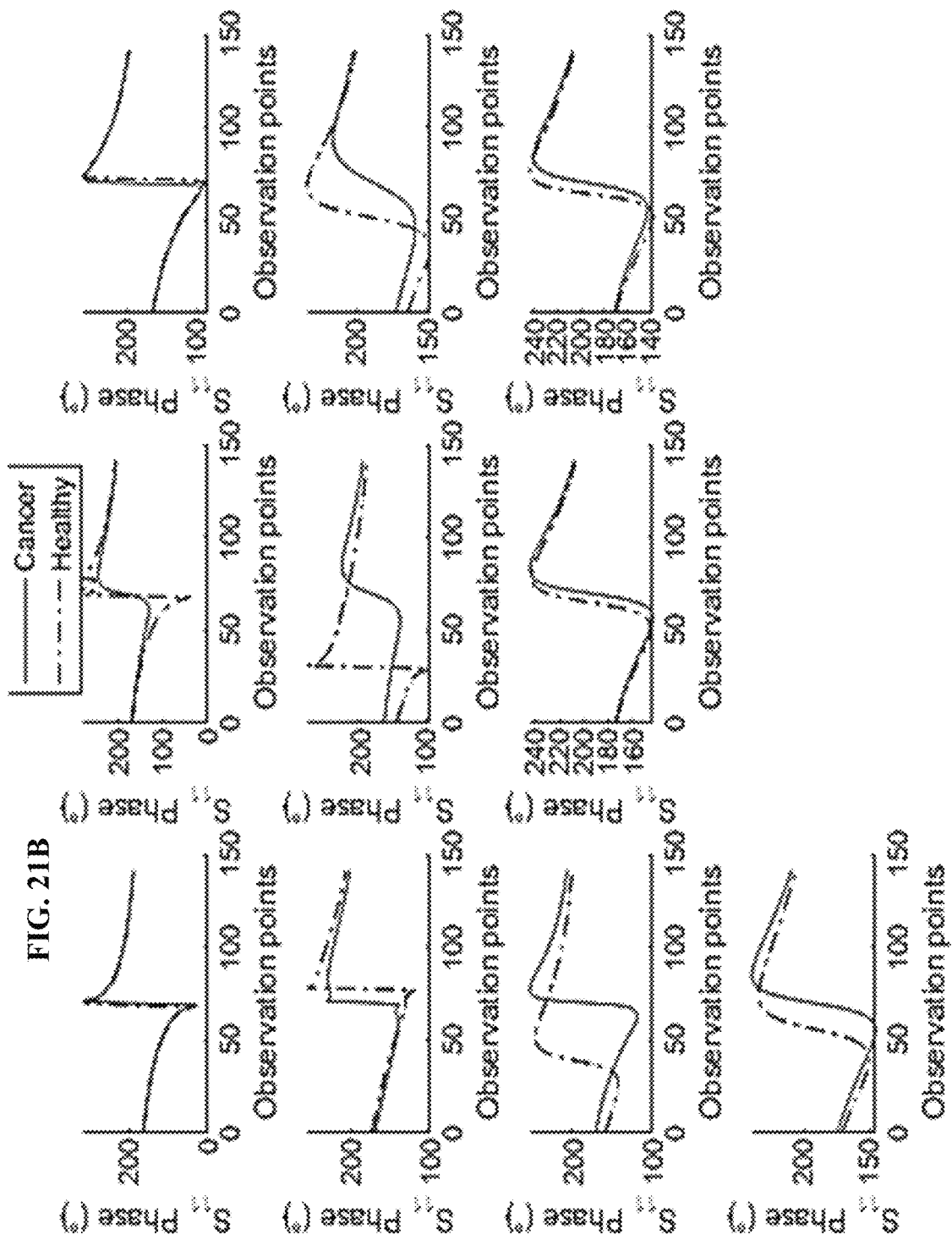
Figure 21C:
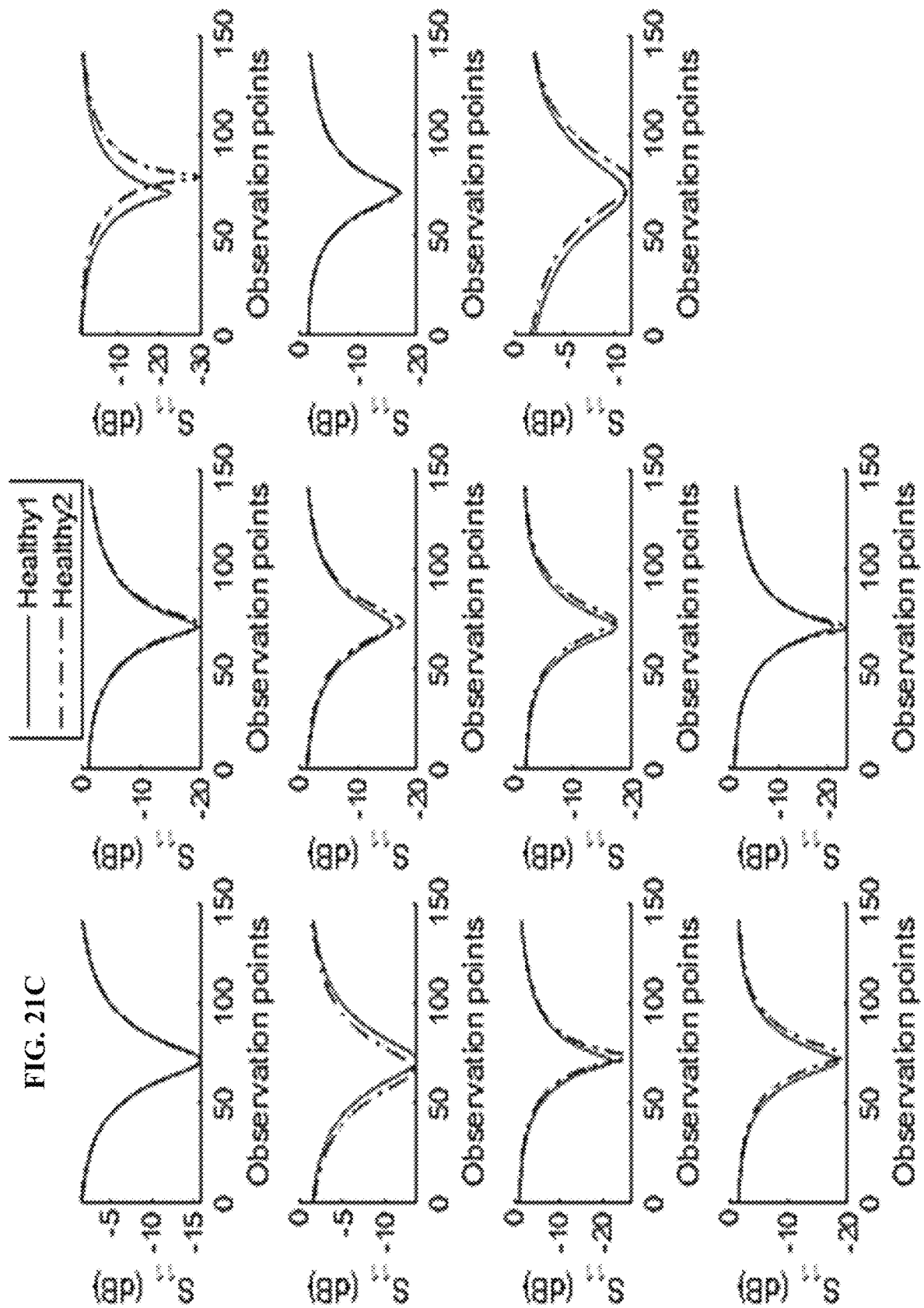
FIGS. 21C-21D are graphs of the recorded data of the $S_{11}$ magnitude and phase response within healthy individuals, respectively.
Figure 21D:
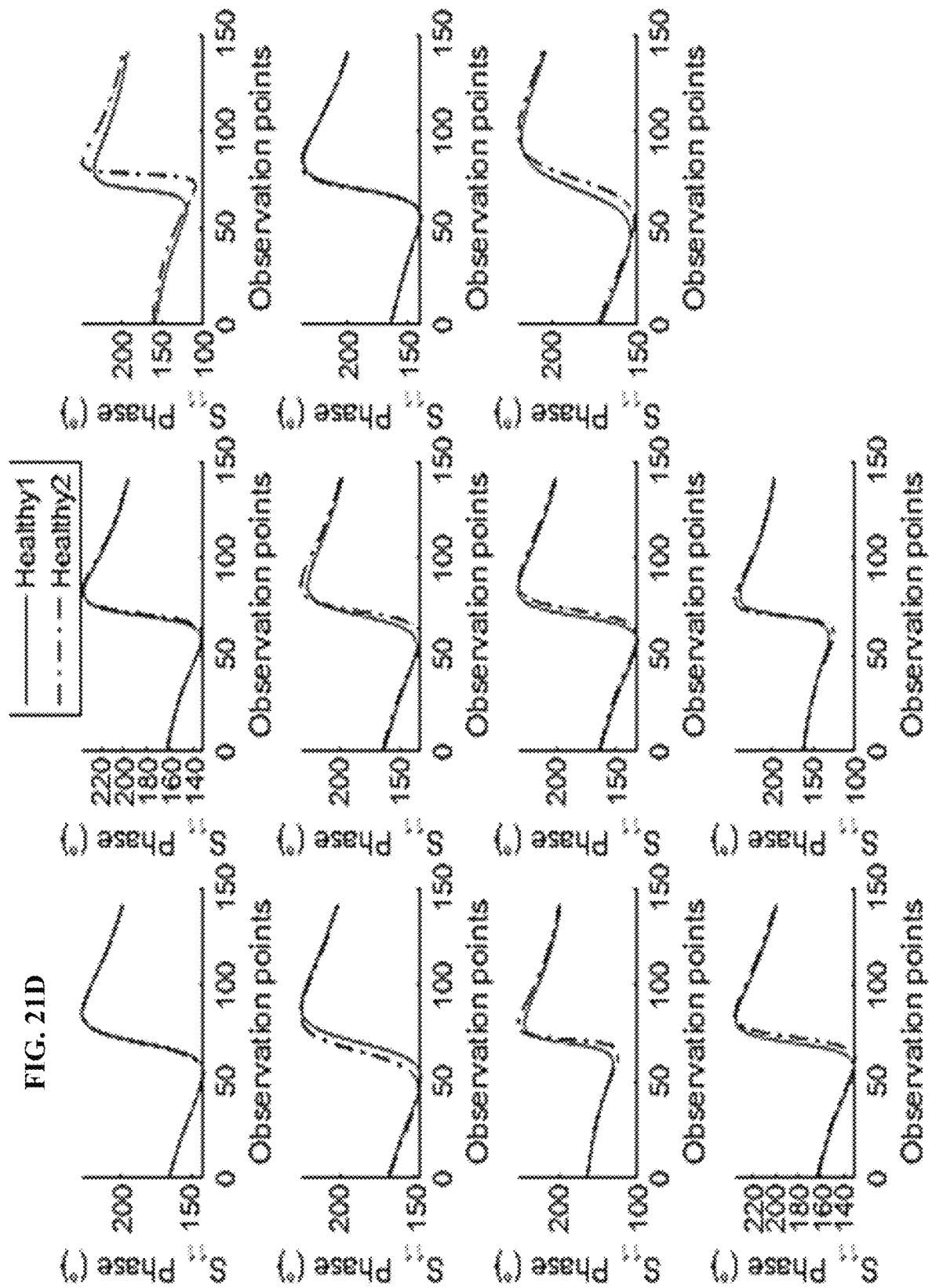
Figure 22B:
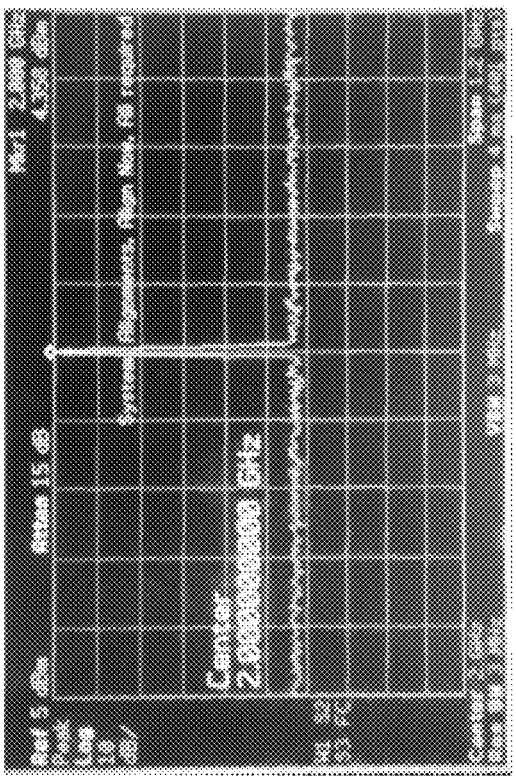
FIGS. 22A-22D are graphs from the spectrum analyzer, showing the synthesized frequencies: (22a) 1 GHz, (22b) 2 GHz, (22c) 3 GHz, and (22d) 6 GHz.
Figure 22D:
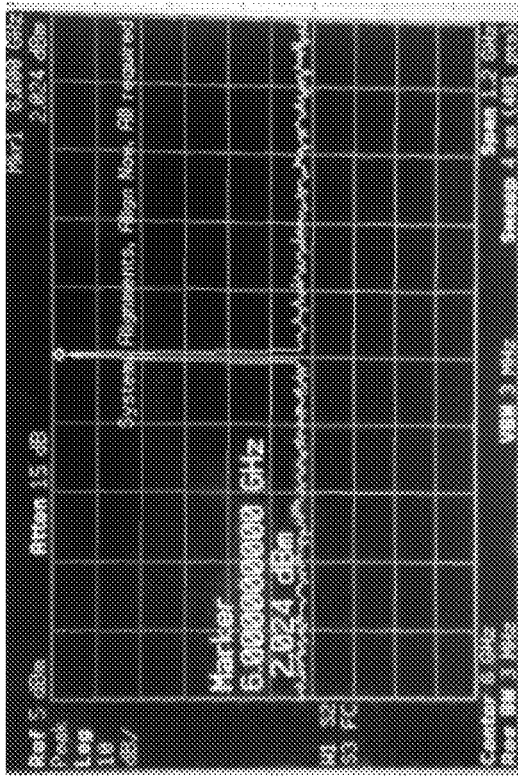
Figure 22A:
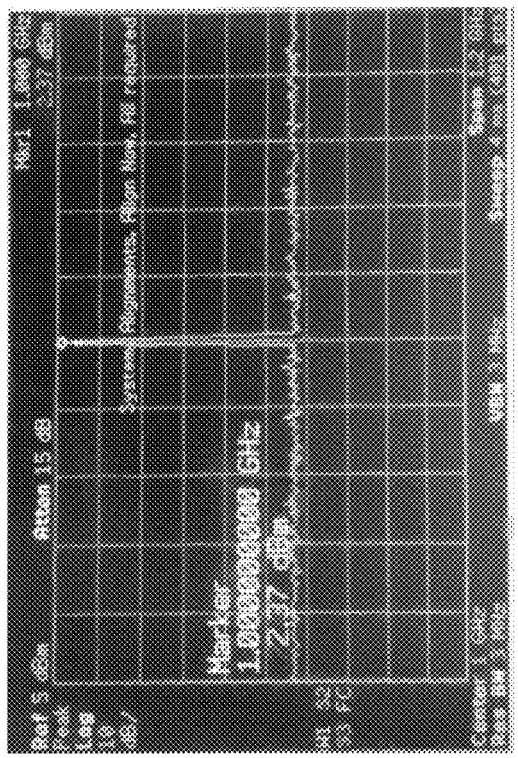
Figure 22C:
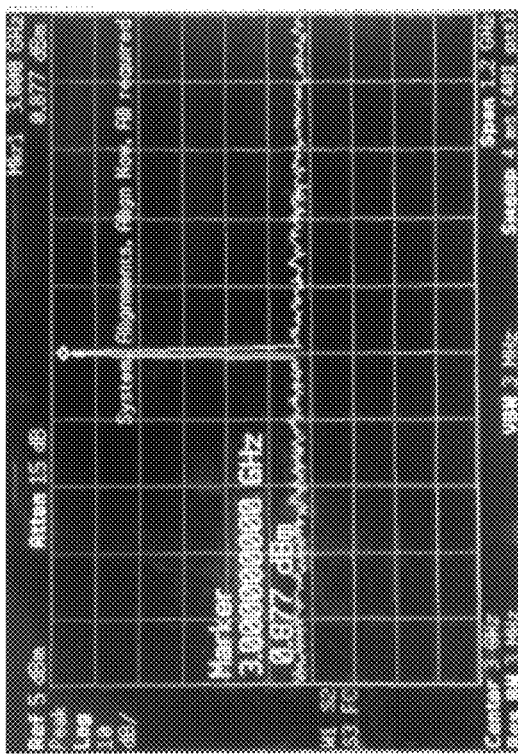

Classification: Multi-Feature Analysis of the Frequency, Magnitude, and Phase of the $S_{11}$ Correlation-Based Classification The collected data correspond to the $S_{11}$ measurements of the healthy and patient populations and the corresponding measurements within each group. By observing the data closely, it is concluded that only a specific range within the entire bandwidth, surrounding the resonance frequency of the sensor and comprising a significant change in the $S_{11}$, is significant for analysis, while the remaining portions are not. As a result, for accuracy, computation time, and visualization purposes, it was convenient to extract 141 points, corresponding to 141 MHz of bandwidth from the original bandwidth. The chosen 141 points are always centered at the resulting sensor's resonance frequency upon loading with a specimen. This procedure is repeated for both the patient's healthy and cancerous measurements while applying any necessary modifications for convenience. The resultant is a bandwidth containing valuable measurements that will be further analyzed. This procedure is then repeated for the healthy volunteers on pairs of data corresponding to adjacent healthy locations (e.g.: Temple1, Temple2, Forehead1, Forehead2). FIG. 21A and FIG. 21B represent the overlapped healthy and cancerous measurements for the patients (12 magnitude, 10 phase) within the selected bandwidth in terms of magnitude and phase respectively. Similarly, FIG. 21C and FIG. 21D represent the overlapped measurements of the healthy subjects in terms of magnitude and phase, respectively.

Simply observing the measurements of patients and healthy controls, whether in magnitude or phase, distinct differences in terms of the shift in frequency and the magnitude and phase of the $S_{11}$ are noticed while very high degrees of similarity are seen in the case of healthy subjects. Accordingly, the square correlation $r^2$ is measured first, also known as the coefficient of determination, of the measurements within each group of participants. In other words, for each patient, the $r_{HC}^2$ corresponding to the correlation between healthy and cancerous lesion multifrequency feature measurement vectors is measured. This correlation is obtained for both the magnitude and phase data ($r_{Phase}^2$ and $r_{Magntiude}^2$). Similarly for the control group, for every participant, the $r_{HH}^2$ corresponding to the correlation between both healthy skin samples is measured. Essentially, the correlation metric provides a measure of how similar two sets of data are across a continuous range of frequencies (within a chosen bandwidth). Since there's interest in quantifying the difference, rather than the similarity within the measured groups, it is more convenient to employ the $1-r^2$ as the measurement quantity. Ultimately, a pair of $1-r^2$ values (magnitude and phase) for each subject within the trial population (healthy and patient) is obtained.

To improve measurement accuracy in the forthcoming analysis, the Synthetic Minority Oversampling Technique (SMOTE) is employed to increase the number of patient measurements, as detailed in above. Consequently, the patient population measurements are increased to 44, matching the 44 healthy measurements, rendering the dataset as balanced. This balanced dataset is then used to build an SVM classification model. The objective of this model is to predict whether a skin lesion is cancerous or not, based on the phase and magnitude correlation values that pass. This data processing algorithm is illustrated by the flow diagram in FIG. 17.

Wrapper-Based Multi-Feature Analysis of the Frequency, Magnitude, and Phase of the $S_{11}$ The patients' dual $S_{11}$ measurements clearly display distinct differences in terms of the frequency shift, the magnitude, and the phase, as shown in FIG. 11. On the other hand, the $S_{11}$ measurement pair of healthy individuals shows a high degree of similarity between the individual elements, which indeed validates the basis of this study: cancerous lesions possess unique dielectric properties. In the data analytics method, these dual measurements corresponding to the populations of cancer, healthy individuals, benign nevi, and arbitrary diseases are used to extract a feature set ($S_{11}$ magnitudes and phases at specific frequencies) that will be used to develop a corresponding classification model. Common to all test scenarios, a two-class classification model is adopted. Since the learning model expects two classes, a cancer one and a non-cancer one, herein, class 1 is the skin cancer class, and class 2 changes depending on the specific scenario. Hence, for scenarios 1, 2, and 3, class 2 corresponds to 'H+BN', 'BN+AD', and 'H+BN+AD', respectively. For purposes of the method and system, the difference of the dual measurements of each individual is computed and use this difference, Δ, obtained at different frequencies as the input features to the model. For purposes of illustration, hereon, the difference obtained for class 1 individual patients is $\Delta_{HC}$. The data that is based on the difference of the dual measurements that comprise the non-cancer population is Δ_HH. The said differential data represent the difference in the $S_{11}$ magnitude (ΔMAG) and phase data (ΔP) for the different classes, e.g.: ($\Delta MAG_{HC}$), ($\Delta P_{HC}$), ($\Delta MAG_{HH}$), and ($\Delta P_{HH}$), as obtained from the dual measurements.

The data analytics method is as follows: First, the difference values for each concerned class is obtained, where for each individual a total of about 282 features is obtained (~141 points for ΔMAG and ~141 points for ΔP) centered around the resonant frequency due to the high quality factor of the sensor (narrow resonance bandwidth). Then, this data passes through a normalization and filtering stage which normalizes the magnitude and phase data and selectively omits dual measurement features (frequencies) that do not meet specific thresholds. Without loss of generality, noting the large observed variations, the thresholds are set to be ΔMAG>about 10 dB and ΔP>about 30°. To improve statistical performance in the forthcoming analysis, a Synthetic Minority Oversampling Technique (SMOTE) is employed to synthetically increase the number of patient measurements.

Figure 24:
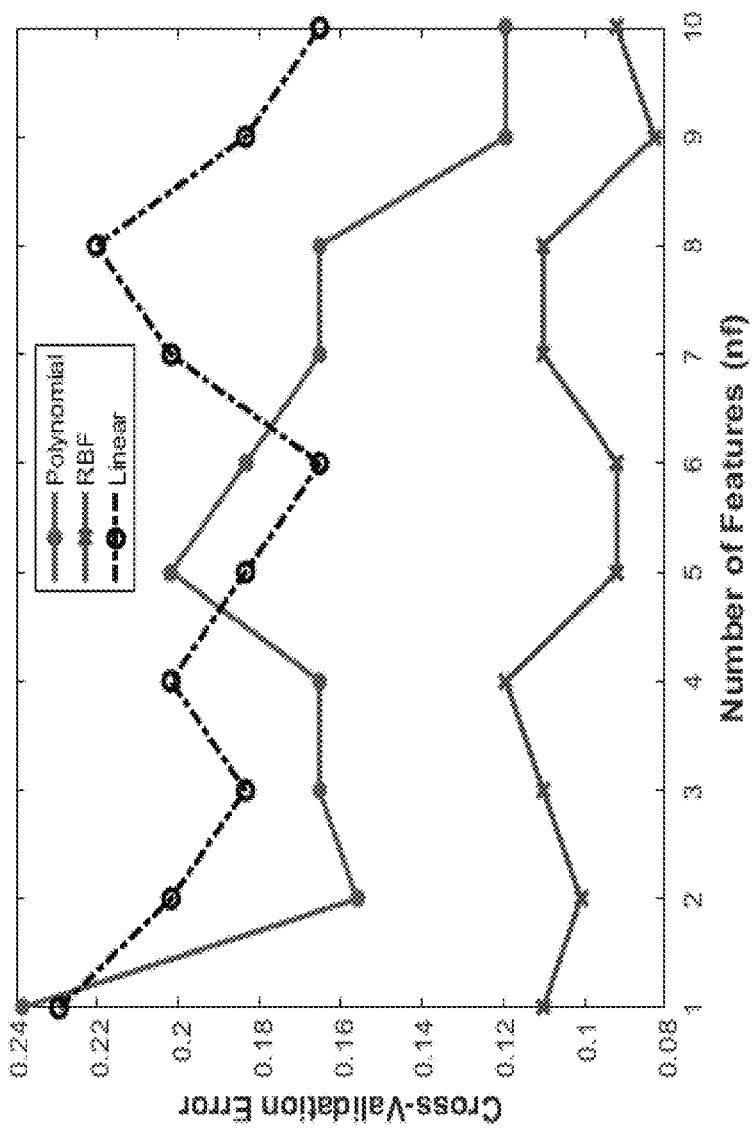
FIG. 24 is a graph of the Cross-Validation (CV) Loss as a function of the number of features for every kernel function.

For all the scenarios, the patient population (class 1) was synthetically increased to match the size of the largest class 2 sub-group. Since the sub-group containing the 'H+BN+AD' is the largest in size, being 61 samples, the cancer population (~18) is increased by 43 synthetic sample points to achieve balance. As for the remaining class 2 scenarios: for 'H+BN', the 'BN' samples are increased synthetically by 7 such that the size of 'H+BN' is 61, and for 'BN+AD' case (totaling 17), both are equally increased to achieve a total of 61 samples. These balanced datasets are then divided into 90% training and 10% testing data. Followingly, a Sequential Feature Selection is employed, which is an algorithm that aims to iteratively identify the feature set producing the highest accuracy based on the resulting CV error to extract the "best features" which will be identified based on the CV error they produce. This is embedded within a wrapper which is used to build multiple SVM classification models with different kernel functions (Polynomial, Radial basis function, and Linear). The resultant CV error of each model is then determined in an effort to identify the best feature set and best kernel function combination. FIG. 24 presents one iteration of such cross-validation error computation for all kernels in the 'SC' vs 'H+BN+AD' experiment. As can be seen in this example, the kernel producing the lowest cross-validation error, and therefore the most accurate model, is the RBF kernel at 9 features. Similarly, the RBF kernel resulted in the highest model accuracy for test scenarios 2 and 3.

Then, in order to maximize sensitivity while not sacrificing specificity, another round of 10-fold cross-validation on the model is invoked using the best kernel, best number of features (nf), and training data to tune the SVM score cut-off, i.e., classification threshold similar to the work in [15]. Typically, the classification relies on a cut-off limit that separates the scores of the two classes, where if the score output of a sample is greater than the cut-off the sample, it is labeled cancerous, and vice versa. As such, for each iteration of the cross-validation, the cut-off is swept and examine the desired performance metrics for the said validation fold. The cut-off that maximizes sensitivity without sacrificing specificity, based on the CV data, is labeled as the "best cut-off". Then, using the training data, the resultant best kernel, the best number of features, and tuned cut-off, an SVM model is built and test its performance based on the data reserved for testing. Details regarding the functionality and parameters of the wrapper method are discussed above. The algorithm is illustrated in FIG. 18. FIG. 18 is the Developed Classification Algorithm 600 and includes the multiple stages that the differential measurements pass through in order to produce a high-performance classifier. Mag_thresh, Phase_Thresh, Best_nf, and Max_Iter are variables that stand for Magnitude Threshold, Phase Threshold, Best Number of Features, and Max Iterations, respective.

System

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

REFERENCES

[1] K. Brind'Amour, "All About Common Skin Disorders," Accessed: Jan. 3, 2021. [Online]. Available: https://www.healthline.com/health/skin-disorders.

[2] "Skin Cancer (Non-Melanoma)—Introduction," *Cancer. Net*, Jun. 25, 2012. https://www.cancer.net/cancer-types/skin-cancer-non-melanoma/introduction (accessed Feb. 4, 2021).

[3] "Basal and Squamous Cell Skin Cancer Tests Skin Cancer Biopsy." https://www.cancer.org/cancer/basal-and-squamous-cell-skin-cancer/detection-diagnosis-staging/how-diagnosed.html (accessed Jan. 3, 2021).

[4] "Skin cancer—Symptoms and causes," *Mayo Clinic*. https://www.mayoclinic.org/diseases-conditions/skin-cancer/symptoms-causes/syc-20377605 (accessed Jan. 3, 2021).

[5] "Radiation: Ultraviolet (UV) radiation and skin cancer.," October 2017, Accessed: Jan. 3, 2021. [Online]. Available: https://www.who.int/news-room/q-a-detail/radiation-ultraviolet-(uv)-radiation-and-skin-cancer.

[6] "Early Detection," *The Skin Cancer Foundation*. https://www.skincancer.org/early-detection/(accessed Jan. 3, 2021).

[7] "Skin cancer—Diagnosis and treatment—Mayo Clinic." https://www.mayoclinic.org/diseases-conditions/skin-cancer/diagnosis-treatment/drc-20377608 (accessed Feb. 4, 2021).

[8] "Melanoma Warning Signs and Images," *The Skin Cancer Foundation*. https://www.skincancer.org/skin-cancer-information/melanoma/melanoma-warning-signs-and-images/(accessed Feb. 3, 2021).

[9] "Not My Face!," *The Skin Cancer Foundation*, Nov. 1, 2017. https://www.skincancer.org/blog/not-my-face/ (accessed Feb. 4, 2021).

[10] K. Abhishek and N. Khunger, "Complications of skin biopsy," *J. Cutan. Aesthetic Surg.*, vol. 8, no. 4, pp. 239-241, 2015, doi: 10.4103/0974-2077.172206.

[11] B. Lindelof and M. A. Hedblad, "Accuracy in the clinical diagnosis and pattern of malignant melanoma at a dermatological clinic," *J. Dermatol.*, vol. 21, no. 7, pp. 461-464, July 1994, doi: 10.1111/j.1346-8138.1994.tb01775.x.

[12] C. A. Morton and R. M. Mackie, "Clinical accuracy of the diagnosis of cutaneous malignant melanoma," *Br. J. Dermatol.*, vol. 138, no. 2, pp. 283-287, February 1998, doi: 10.1046/j.1365-2133.1998.02075.x.

[13] I. Korom, G. Gaszner, G. Haraszti, L. Szekeres, C. Bertényi, and A. Dobozy, "[Reliability of clinical diagnosis in malignant melanoma]," *Orv. Hetil.*, vol. 134, no. 24, pp. 1309-1311, June 1993.

[14] M. D. Corbo and J. Wismer, "Agreement between dermatologists and primary care practitioners in the diagnosis of malignant melanoma: review of the literature," *J. Cutan. Med. Surg.*, vol. 16, no. 5, pp. 306-310, October 2012, doi: 10.1177/120347541201600506.

[15] P. Aberg, I. Nicander, J. Hansson, P. Geladi, U. Holmgren, and S. Ollmar, "Skin cancer identification using multifrequency electrical impedance—a potential screening tool," *IEEE Trans. Biomed. Eng.*, vol. 51, no. 12, pp. 2097-2102, December 2004, doi: 10.1109/TBME.2004.836523.

[16] T. J. Brinker et al., "Skin Cancer Classification Using Convolutional Neural Networks: Systematic Review," *J. Med. Internet Res.*, vol. 20, no. 10, p. e11936, 2018, doi: 10.2196/11936.

[17] "Using Deep Learning to Inform Differential Diagnoses of Skin Diseases," *Google AI Blog*. http://ai.googleblog.com/2019/09/using-deep-learning-to-inform.html (accessed Feb. 4, 2021).

[18] F. Töpfer, S. Dudorov, and J. Oberhammer, "Millimeter-Wave Near-Field Probe Designed for High-Resolution Skin Cancer Diagnosis," *IEEE Trans. Microw. Theory Tech.*, vol. 63, no. 6, pp. 2050-2059, June 2015, doi: 10.1109/TMTT.2015.2428243.

[19] A. Taeb, S. Gigoyan, and S. Safavi-Naeini, "Millimetre-wave waveguide reflectometers for early detection of skin cancer," *IET Microw. Antennas Propag.*, vol. 7, no. 14, pp. 1182-1186, November 2013, doi: 10.1049/iet-map.2013.0189.

[20] A. Rahman, A. K. Rahman, and B. Rao, "Early detection of skin cancer via terahertz spectral profiling and 3D imaging," *Biosens. Bioelectron.*, vol. 82, pp. 64-70, August 2016, doi: 10.1016/j.bios.2016.03.051.

[21] J. L. Schepps and K. R. Foster, "The UHF and microwave dielectric properties of normal and tumour tissues: variation in dielectric properties with tissue water content," *Phys. Med. Biol.*, vol. 25, no. 6, pp. 1149-1159, November 1980, doi: 10.1088/0031-9155/25/6/012.

[22] M. Lazebnik et al., "A large-scale study of the ultra-wideband microwave dielectric properties of normal, benign and malignant breast tissues obtained from cancer surgeries," *Phys. Med. Biol.*, vol. 52, no. 20, pp. 6093-6115, October 2007, doi: 10.1088/0031-9155/52/20/002.

[23] A. Mirbeik-Sabzevari, R. Ashinoff, and N. Tavassolian, "Ultra-wideband millimeter-wave dielectric characteristics of freshly excised normal and malignant human skin tissues," *IEEE Trans. Biomed. Eng.*, vol. 65, no. 6, pp. 1320-1329, June 2018, doi: 10.1109/TBME.2017.2749371.

[24] A. Zamani, S. A. Rezaeieh, and A. M. Abbosh, "Lung cancer detection using frequency-domain microwave imaging," *Electron. Lett.*, vol. 51, no. 10, pp. 740-741, April 2015, doi: 10.1049/el.2015.0230.

[25] S. I. Alekseev, I. Szabo, and M. C. Ziskin, "Millimeter wave reflectivity used for measurement of skin hydration with different moisturizers," *Skin Res. Technol. Off. J. Int. Soc. Bioeng. Skin ISBS Int. Soc. Digit. Imaging Skin ISDIS Int. Soc. Skin Imaging ISSI*, vol. 14, no. 4, pp. 390-396, November 2008, doi: 10.1111/j.1600-0846.2008.00319.x.

[26] "Noninvasive, wearable, and tunable electromagnetic multisensing system for continuous glucose monitoring, mimicking vasculature anatomy|Science Advances." https://advances.sciencemag.org/content/6/24/eaba5320/tab-figures-data (accessed Feb. 5, 2021).

[27] D. Patt et al., "Impact of COVID-19 on Cancer Care: How the Pandemic Is Delaying Cancer Diagnosis and Treatment for American Seniors," *JCO Clin. Cancer Inform.*, November 2020, doi: 10.1200/CCI.20.00134.

[28] S. N. S. Gorin, M. Jimbo, R. Heizelman, K. M. Harmes, and D. M. Harper, "The future of cancer screening after COVID-19 may be at home," *Cancer*, vol. 127, no. 4, pp. 498-503, 2021, doi: https://doi.org/10.1002/cncr.33274.

[29] C. H. Earnshaw, H. J. A. Hunter, E. McMullen, C. E. M. Griffiths, and R. B. Warren, "Reduction in skin cancer diagnosis, and overall cancer referrals, during the COVID-19 pandemic," *Br. J. Dermatol.*, vol. 183, no. 4, pp. 792-794, October 2020, doi: 10.1111/bjd.19267.

[30] T. W. Andrew, M. Alrawi, and P. Lovat, "Reduction in skin cancer diagnoses in the UK during the COVID-19 pandemic," *Clin. Exp. Dermatol.*, vol. 46, no. 1, pp. 145-146, 2021, doi: https://doi.org/10.1111/ced.14411.

[31] "Doctors Warn of Skin Cancer Screening Crisis," *Medscape*. http://www.medscape.com/viewarticle/944885 (accessed Feb. 4, 2021).

[32] F. Kazemi, F. Mohanna, and J. Ahmadi-Shokouh, "Detection of biological abnormalities using a near-field microwave microscope," *Int. J. Microw. Wirel. Technol.*, vol. 10, no. 8, pp. 933-941, October 2018, doi: 10.1017/S1759078718000752.

[33] L. F. Chen, C. K. Ong, C. P. Neo, V. V. Varadan, and V. K. Varadan, *Microwave electronics: Measurement and materials characterization*. Wiley, 2004.

[34] M. Tabib-Azar, J. L. Katz, and LeClair, "Evanescent microwaves: a novel super-resolution noncontact nondestructive imaging technique for biological applications," *IEEE Trans. Instrum. Meas.*, vol. 48, no. 6, pp. 1111-1116, December 1999, doi: 10.1109/19.816123.

[35] F. Kazemi, F. Mohanna, and J. Ahmadi-Shokouh, "Nondestructive high-resolution microwave imaging of biomaterials and biological tissues," *AEU—Int. J. Electron. Commun.*, vol. 84, pp. 177-185, 2018, doi: https://doi.org/10.1016/j.aeue.2017.10.031.

[36] D. Pozar, *Microwave engineering*. Hoboken, NJ: Wiley, 2012.
[37] "Radiofrequency (RF) Radiation." https://www.cancer.org/cancer/cancer-causes/radiation-exposure/radiofrequency-radiation.html (accessed Feb. 5, 2021).
[38] "Radio Frequency Safety," *Federal Communications Commission*, Mar. 2, 2011. https://www.fcc.gov/general/radio-frequency-safety-0 (accessed Jan. 8, 2021).
[39] "Federalwide Assurance." https://www.aub.edu.lb/irb/Pages/federalwideassurance.aspx (accessed Feb. 5, 2021).
[40] S. Gabriel, R. W. Lau, and C. Gabriel, "The dielectric properties of biological tissues: II. Measurements in the frequency range 10 Hz to 20 GHz," *Phys. Med. Biol.*, vol. 41, no. 11, pp. 2251-2269, November 1996, doi: 10.1088/0031-9155/41/11/002.
[41] D. Huber, M. Talary, F. Dewarrat, and A. Caduff, "The compensation of perturbing temperature fluctuation in glucose monitoring technologies based on impedance spectroscopy," *Med. Biol. Eng. Comput.*, vol. 45, no. 9, pp. 863-876, September 2007, doi: 10.1007/s11517-007-0229-3.
[42] D. A. Pollacco, L. Farina, P. S. Wismayer, L. Farrugia, and C. V. Sammut, "Characterization of the dielectric properties of biological tissues and their correlation to tissue hydration," *IEEE Trans. Dielectr. Electr. Insul.*, vol. 25, no. 6, pp. 2191-2197, December 2018, doi: 10.1109/TDEI.2018.007346.
[43] R. J. Halter et al., "The correlation of in vivo and ex vivo tissue dielectric properties to validate electromagnetic breast imaging: initial clinical experience," *Physiol. Meas.*, vol. 30, no. 6, pp. S121-S136, June 2009, doi: 10.1088/0967-3334/30/6/S08.
[44] L. Farrugia, P. S. Wismayer, L. Z. Mangion, and C. V. Sammut, "Accurate in vivo dielectric properties of liver from 500 MHz to 40 GHz and their correlation to ex vivo measurements," *Electromagn. Biol. Med.*, vol. 35, no. 4, pp. 365-373, October 2016, doi: 10.3109/15368378.2015.1120221.
[45] S. Salahuddin, A. L. Gioia, M. A. Elahi, E. Porter, M. O'Halloran, and A. Shahzad, "Comparison of in-vivo and ex-vivo dielectric properties of biological tissues," in 2017 *International Conference on Electromagnetics in Advanced Applications (ICEAA)*, September 2017, pp. 582-585, doi: 10.1109/ICEAA.2017.8065312.
[46] "Considering Laser Hair Removal? Get To Know Your Fitzpatrick Skin Type—Barris Laser & Skin Care—Boulder, CO" https://barrislaser.com/considering-laser-hair-removal-get-to-know-your-fitzpatrick-skin-type/(accessed Jan. 10, 2021).
[47] "RT/Duroid® 5880 Laminates—Rogers Corporation." https://rogerscorp.com/advanced-connectivity-solutions/rt-duroid-laminates/rt-duroid-5880-laminates (accessed Feb. 15, 2021).
[48] "ANSYS HFSS: High Frequency Electromagnetic Field Simulation Software." https://www.ansys.com/products/electronics/ansys-hfss (accessed Jan. 3, 2021).
[49] "N9923A FieldFox Handheld RF Vector Network Analyzer, 4 GHz and 6 GHz Keysight." https://www.keysight.com/en/pdx-x201782-pn-N9923A/fieldfox-handheld-rf-vector-network-analyzer-4-ghz-and-6-ghz?cc=LB&lc=eng (accessed Jan. 3, 2021).

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A novel electromagnetic (EM)-based diagnostics and monitoring system for the non-Invasive diagnosis and monitoring of in-vivo and ex-vivo Skin Anomalies, comprising: an EM sensor including a plurality of components operating within the radio-frequency portion of the spectrum from 30 MHz-300 GHz, wherein the plurality of components include an integrated circuit operably coupled to a printed circuit board; wherein the plurality of components include an EM sensor that interacts with a specimen under test, the EM sensor synthesizes a radio-frequency signal, and the specimen under test energizes the EM sensor; the EM sensor captures incident and reflected waves from the specimen under test, and the EM sensor performs signal processing operations at RF and low frequencies including filtering, coupling, amplification, attenuation, and down-conversion, processes, and collects the obtained data; and the EM sensor applies a plurality of algorithms to extract the constituency, characteristics, and properties of the specimen under test; wherein the specimen under test is an in-vivo or ex-vivo skin anomaly including skin cancer, benign tumors, or other skin diseases; and the plurality of algorithms provide diagnostic decisions based on the collected response through the EM sensor by a measured incident, reflected and transmitted wave properties including an S-parameter response.

2. The system in claim 1, further comprising measuring the magnitude and phase of the S-parameters at multiple frequencies.

3. The system in claim 2, further comprising a wave analyzer device, a centralized database, and a data processing, and a machine learning algorithm operably coupled to the EMS sensor.

4. The system in claim 3, wherein the EM sensor comprises an electromagnetic structure including an antenna, a resonator, a filter, a passive or an active RF devices to emanate, transmit or manipulate electromagnetic waves.

5. The system in claim 4, wherein the EM sensor senses electromagnetic differences in in-vivo and ex-vivo skin conditions in the specimen under test.

6. The system in claim 5, wherein the EM sensor comprises one-port or multiple ports; the EM sensor is a microstrip including a length that designates operation within the microwave frequency range; the EM sensor comprises one or more matching sections that enable impedance matching between the source impedance and the sensor's input impedance.

7. The system of claim 6, wherein the EM sensor comprises substrates or dielectric materials with varying dielectric properties; and wherein the EM sensor includes a lesion-optimized sensing tip or a lesion optimized topology.

8. The system of claim 7, wherein the lesion-optimized sensing tip includes a geometrical shape that heightens sensitivity to small lesions and minimizes interactions with undesired regions surrounding the lesion; and the lesion-optimized sensing tip includes a hemisphere.

9. The system of claim 8, wherein the hemisphere improves the overall sensitivity by enhancing the sensor's interaction with the specimen under test in terms of sensing field concentration and density, and minimizing the interaction with undesired regions surrounding the lesion due the geometrical shape, which enables the detection of the tumor's boundary.

10. The system of claim 9, wherein the lesion-optimized sensing tip is characterized by a concentrated field density at the hemispherical sensing tip and this enables a practical stand-off distance from the specimen under test allowing placement of a foam separator between the sensor and specimen.

11. The system of claim 10, wherein the EM sensor is shielded with an enclosure that provides immunity to ambient RF noise.

12. The system of claim 11, wherein the wave analyzer system operates in the Microwave frequency range and in the millimeter-wave frequency range; the wave analyzer system includes a vector network analyzer subsystem, a power sensor, a time domain analyzer, a spectrum analyzer or a reflectometer; the wave analyzer includes multiple passive and active RF components to facilitate signal manipulation including a filters, an amplifier, and an attenuator; the wave analyzer utilizes analog and digital filtering techniques to improve the measurement quality; the wave analyzer comprises a plurality of calibration techniques, including an open-short-load, or a single full reflection loads such as open or short circuits to improve measurement performance and cancel or diminish system errors and losses; the wave analyzer system measures the power of incident or reflected signals as well as the complex reflection and transmission coefficients; the wave analyzer includes an on-board control unit that includes a microcontroller, a microprocessor, a field programmable gate array.

13. The system of claim 12, wherein the wave analyzer interfaces with external computational systems including personal computers, mobile phones, and tablets; the wave analyzer collects and generates data based on patient profiles, and sensor measurements, comprises a plurality of algorithms that interact with the cloud and the database to predict the properties of the lesion for a specific category of lesion and patient, and the plurality of algorithm forward the data to a web-based cloud system for data modelling enhancement procedures and model updates.

14. The system of claim 13, further comprising a frequency generation circuit to synthesize required high frequency signals, where the frequency generation circuit include at least one Voltage Controlled Oscillator or at least one Phase-locked loop; the frequency generation circuit further comprises a plurality of directional couplers as the main wave coupling structure; the frequency generation circuit further comprises two gain and phase detectors to extract a reflection coefficient magnitude from an incident and a reflected wave; the frequency generation circuit further comprises phase shifting at one input of the detectors to enable a full 0-360 degrees phase measurement; the frequency generation circuit further comprises an attenuator in the coupled incident wave path to balance its magnitude level with that of the coupled reflected wave.

15. The system of claim 14, wherein the wave analyzer utilizes WiFi and USB-enabled Arduino microcontrollers.

16. The system of claim 15, wherein a short-circuit load is used to perform magnitude calibration; the magnitude and phase of an EM sensor are measured in a loaded state with a skin sample at one location selected from the group consisting of: the face, arms, and other locations on the body, and an unloaded state as a free-space measurement.

17. The system of claim 16, wherein the wave analyzer's printed circuit board is composed of 4 layers, where each layer corresponds to a copper layer such as a grounding layer, a signal routing and component assembly layer, and a power plane management layer; the 4 layers enables higher isolation between signal lines due to the multi-layer topology including the grounding vias and ground pours within; the 4 layers achieves more compactness due to the ability to route signal and power lines on more than one layer; the 4 layers ensures tight impedance control due to a continuous ground plane beneath the RF signal layer.

18. The system of claim 17, further comprising algorithm modules and predictive models to transform magnitude, phase, and frequency measurements of the reflection and transmission coefficients to specimen characteristics predictions.

19. The system of claim 18, wherein the algorithm modules and predictive models utilize correlation-based classifiers that relates the S-parameter response across the frequency spectrum or utilizes best feature selection algorithms to identify representative S-parameter response at specific frequencies that best predicts the nature and condition of a specimen under test; and the algorithm modules and predictive models utilize SMOTE to balance imbalanced datasets.

20. The system of claim 19, further comprising a correlation-based classifier uses the correlation values between healthy and anomalous skin lesions within a patient in of magnitude and phase to build a classifier able to predict whether a skin lesion is cancerous, benign, and/or healthy; a best feature selector is used to extract the set of magnitudes and phases of the reflection coefficient at multiple frequencies to predict whether a skin lesion is cancerous, benign, and/or healthy; and a classification algorithm including a support vector machine (SVM).

* * * * *